(12) United States Patent
Walker et al.

(10) Patent No.: US 8,633,153 B2
(45) Date of Patent: Jan. 21, 2014

(54) TRANSTHYRETIN VARIANTS

(75) Inventors: Kenneth William Walker, Newbury Park, CA (US); **Fei

TRANSTHYRETIN VARIANTS

CROSS-REFERENCE TO RELATED APPLICATIONS

This application is a Continuation of U.S. application Ser. No. 10/407,078, filed Apr. 3, 2003, now abandoned. which is a Continuation-in-part of U.S. application Ser. No. 10/117, 109, filed Apr. 4, 2002, now abandoned, which are hereby incorporated by reference.

BACKGROUND OF THE INVENTION

Proteins, peptides and other drug molecules for therapeutic use are currently available in suitable forms in adequate quantities largely as a result of the advances in recombinant DNA technologies. The availability of such peptides and proteins has engendered advances in protein formulation and chemical modification. Chemical modification of biologically active peptides, proteins, oligonucleotides and other drugs for purposes of extending the serum half-life of such bioactive agents has been extensively studied. The ability to extend the serum half-life of such agents allows for the therapeutic potential of the agent to be realized without the need for high dosages and frequent administration.

Chemical modification used to extend the half-lives of proteins in vivo includes the chemical conjugation of a water soluble polymer, such as polyethylene glycol (PEG), to the protein of interest. A variety of approaches have been used to attach the polyethylene glycol molecules to the protein (PEGylation). For example, Royer (U.S. Pat. No. 4,002,531) states that reductive alkylation was used for attachment of polyethylene glycol molecules to an enzyme. Davis et al. (U.S. Pat. No. 4,179,337) disclose PEG:protein conjugates involving, for example, enzymes and insulin. Shaw (U.S. Pat. No. 4,904,584) disclose the modification of the number of lysine residues in proteins for the attachment of polyethylene glycol molecules via reactive amine groups. Hakimi et al. (U.S. Pat. No. 5,834,594) disclose substantially non-immunogenic water soluble PEG:protein conjugates, involving for example, the proteins IL-2, interferon alpha, and IL-1ra. The methods of Hakimi et al. involve the utilization of unique linkers to connect the various free amino groups in the protein to PEG. Kinstler et al. (U.S. Pat. Nos. 5,824,784 and 5,985, 265) teach methods allowing for selectively N-terminally chemically modified proteins and analogs thereof, including G-CSF and consensus interferon.

Other approaches designed to extend the serum half-life of bioactive agents include: conjugation of the peptides to a large, stable protein which is too large to be filtered through the kidneys (e.g., serum albumin); G. D. Mao et al., *Biomat., Art. Cells, Art. Org.* 17:229-244 (1989); use of low- and high-density lipoproteins as transport vehicles and to increase serum half-life; P. Chris de Smidt et al., *Nuc. Acids. Res.,* 19(17):4695-4700 (1991); the use of the Fc region of immunoglobulins to produce Fc-protein fusions; PCT WO 98/28427 (Mann et al, and references cited therein); and the use of the Fc domain to increase in vivo half-life of one or more biologically active peptides; PCT WO 00/24782 (Feige et al, and references cited therein).

Transthyretin (TTR) (formerly called prealbumin) is a 56 kDa tetrameric serum protein that plays important physiological roles as a transporter of thyroxine and retinol-binding protein; Hamilton and Benson, *Cell. Mol. Life Sci.,* 58:1491-1521 (2001), and references cited therein. Blaney et al., in U.S. Pat. No. 5,714,142, describe the exploitation of TTR by endowing the drug to be administered with functionality that allows it to bind specifically to the protein. Specifically, Blaney et al. demonstrate that covalent attachment of a peptide, protein, nucleotide, oligonucleotide, oligosaccharide or other drug to a transthyretin-selective ligand will reversibly bind the drug to TTR and thereby increase the serum half-life of the agent based on the affinity of the ligand for TTR. It is stated that the intrinsic activity of the drug is not adversely affected and the resulting drug-TTR ligand conjugate will still be small enough to be orally absorbed.

SUMMARY OF THE INVENTION

It has been found, surprisingly and importantly, that TTR (or a TTR variant), and in particular, a TTR or TTR variant which has been chemically modified via conjugation to a water soluble polymer, e.g., can be used as a fusion partner with a biologically active agent to increase the serum half-life of the biologically active agent. Accordingly, the present invention provides a means for increasing the serum half-life of a selected biologically active agent.

The present invention thus relates to substantially homogenous preparations of TTR (or a TTR variant)-biologically active agent fusions and PEG-TTR (PEG-TTR variant)-biologically active agent fusions. As compared to the biologically active agent alone, the TTR-biologically active agent fusion and/or PEG-TTR-biologically active agent fusion has substantially increased serum half-life.

The present invention further relates to TTR-biologically active agent fusions and PEG-TTR-biologically active agent fusions, in a pharmaceutically acceptable carrier, to provide a pharmacologically active compound.

The present invention further relates to the preparation of TTR variants. Specifically, TTR proteins are modified such that cysteine residue(s) are engineered into the TTR protein sequence. The TTR variants are recoverable in high yield and are then chemically modified via conjugation of a water soluble polymer at the cysteine residue to provide a chemically modified TTR variant which can then be fused to a selected biologically active agent.

The present invention further relates to processes for preparing pharmacologically active compounds. For example, the principal embodiment of the method for making the substantially homogenous preparation of a PEG-TTR-peptide fusion comprises: (a) engineering a cysteine residue into a specific amino acid position within the amino acid sequence of said TTR to provide a variant of said TTR; (b) conjugating a polyethylene glycol to said TTR variant at said cysteine residue to provide a PEG-TTR; (c) fusing said PEG-TTR to a peptide of interest to provide a PEG-TTR-peptide fusion; and (d) isolating said PEG-TTR-peptide fusion.

The present invention also relates to methods of treatment of individuals using the pharmacologically active compounds as above.

DETAILED DESCRIPTION OF THE INVENTION

Figure 1:
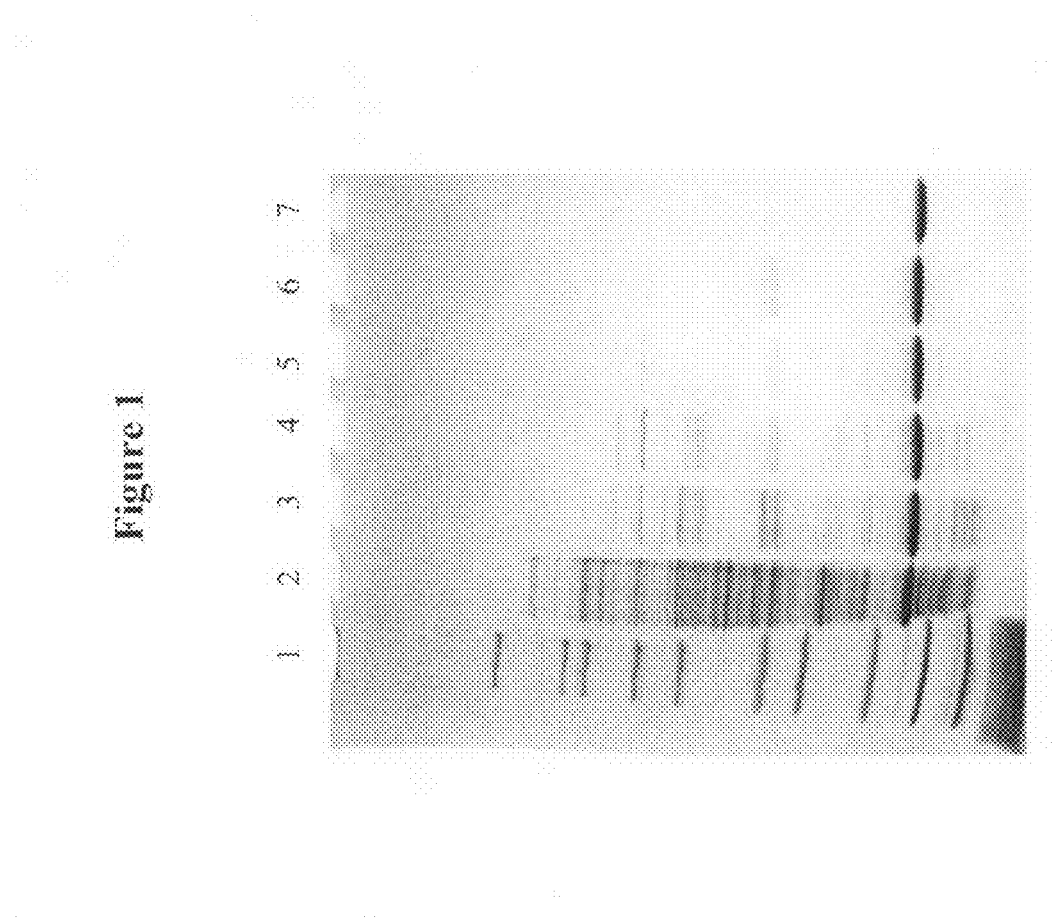
FIG. 1 is an SDS gel that depicts the purification of an *E. coli* expressed, recombinant human transthyretin (TTR) variant (C10A/G83C) with a Bradykinin peptide fused to the C-terminus of TTR. Lane 1 contains NOVEX® 12 molecular weight standards, and lanes 2-7 contain the following respectively: cell lysate, post-heating supernatant, pool from Q-sepharose chromatography step, pool from phenyl sepharose chromatography step, pool from hydroxyapatite chromatography step, and pool from source Q chromatography step.

For purposes of describing the present invention, the following terms are defined as set forth below.

The term "biologically active agent" refers to any chemical material or compound useful for prophylactic, therapeutic or diagnostic application. The term "pharmacologically active compound" refers to a compound suitable for administration to a mammalian, preferably a human individual, which induces a desired local or systemic effect.

The terms "peptide", "polypeptide" and "protein" describe a type of biologically active agents, and the terms are used interchangeably herein to refer to a naturally occurring, recombinantly produced or chemically synthesized polymer of amino acids. The terms are intended to include peptide molecules containing as few as 2 amino acids, chemically modified polypeptides, consensus molecules, analogs, derivatives or combinations thereof.

Any number of peptides may be used in conjunction with the present invention. Of particular interest are peptides that mimic the activity of erythropoietin (EPO), thrombopoietin (TPO), Glucagon-like Peptide 1 (GLP-1), parathyroid hormone (PTH), granulocyte-colony stimulating factor (G-CSF), granulocyte macrophage-colony stimulating factor (GM-CSF), interleukin-1 receptor antagonist (IL-1ra), leptin, cytotoxic T-lymphocyte antigen 4 (CTLA4), TNF-related apoptosis-inducing ligand (TRAIL), tumor growth factor-alpha and beta (TGF-α and TGF-β, respectively), and growth hormones. The terms "-mimetic peptide" and "-agonist peptide" refer to a peptide having biological activity comparable to a protein (e.g., GLP-1, PTH, EPO, TPO, G-CSF, etc.) that interacts with a protein of interest. These terms further include peptides that indirectly mimic the activity of a protein of interest, such as by potentiating the effects of the natural ligand of the protein of interest. Thus, the term "EPO-mimetic peptide" comprises any peptides that can be identified or derived as having EPO-mimetic subject matter; see, for example, Wrighton et al., *Science*, 273:458-63 (1996); and Naranda et al., *Proc. Natl. Acad. Sci. USA* 96:7569-74 (1999). Those of ordinary skill in the art appreciate that each of these references enables one to select different peptides than actually disclosed therein by following the disclosed procedures with different peptide libraries.

The term "TPO-mimetic peptide" (TMP) comprises peptides that can be identified or derived as having TPO-mimetic subject matter; see, for example, Cwirla et al., *Science*, 276: 1696-9 (1997); U.S. Pat. Nos. 5,869,451 and 5,932,946; and PCT WO 00/24782 (Liu et al, and references cited therein), hereby incorporated by reference in its entirety. Those of ordinary skill in the art appreciate that each of these references enables one to select different peptides than actually disclosed therein by following the disclosed procedures with different peptide libraries.

The term "G-CSF-mimetic peptide" comprises any peptides that can be identified as having G-CSF-mimetic subject matter; see, for example, Paukovits et al., *Hoppe-Seylers Z. Physiol. Chem.* 365:303-11 (1984). Those of ordinary skill in the art appreciate that each of these references enables one to select different peptides than actually disclosed therein by following the disclosed procedures with different peptide libraries.

The term "CTLA4-mimetic peptide" comprises any peptides that can be identified or derived as described in Fukumoto et al., *Nature Biotech.* 16:267-70 (1998). Those of ordinary skill in the art appreciate that each of these references enables one to select different peptides than actually disclosed therein by following the disclosed procedures with different peptide libraries.

Peptide antagonists are also of interest, particularly those antagonistic to the activity of TNF, leptin, any of the interleukins, and proteins involved in complement activation (e.g., C3b). The term "-antagonist peptide" or "inhibitor peptide" refers to a peptide that blocks or in some way interferes with the biological activity of the associated protein of interest, or has biological activity comparable to a known antagonist or inhibitor of the associated protein of interest. Thus, the term "TNF-antagonist peptide" comprises peptides that can be identified or derived as having TNF-antagonistic subject matter; see, foe example, Takasaki et al., *Nature Biotech.*, 15:1266-70 (1997). Those of ordinary skill in the art appreciate that each of these references enables one to select different peptides than actually disclosed therein by following the disclosed procedures with different peptide libraries.

The terms "IL-1 antagonist" and "IL-1ra-mimetic peptide" comprises peptides that inhibit or down-regulate activation of the IL-1 receptor by IL-1. IL-1 receptor activation results from formation of a complex among IL-1, IL-1 receptor, and IL-1 receptor accessory protein. IL-1 antagonist or IL-1ra-mimetic peptides bind to IL-1, IL-1 receptor, or IL-1 receptor accessory protein and obstruct complex formation among any two or three components of the complex. Exemplary IL-1 antagonist or IL-1ra-mimetic peptides can be identified or derived as described in U.S. Pat. Nos. 5,608,035, 5,786,331, 5,880,096. Those of ordinary skill in the art appreciate that each of these references enables one to select different peptides than actually disclosed therein by following the disclosed procedures with different peptide libraries.

The term "VEGF-antagonist peptide" comprises peptides that can be identified or derived as having VEGF-antagonistic subject matter; see, for example, Fairbrother, *Biochem.*, 37:17754-64 (1998). Those of ordinary skill in the art appreciate that each of these references enables one to select different peptides than actually disclosed therein by following the disclosed procedures with different peptide libraries.

The term "MMP inhibitor peptide" comprises peptides that can be identified or derived as having MMP inhibitory subject matter; see, for example, Koivunen, *Nature Biotech.*, 17:768-74 (1999). Those of ordinary skill in the art appreciate that each of these references enables one to select different peptides than actually disclosed therein by following the disclosed procedures with different peptide libraries.

Targeting peptides are also of interest, including tumor-homing peptides, membrane-transporting peptides, and the like.

Exemplary peptides may be randomly generated by various techniques known in the art. For example, solid phase synthesis techniques are well known in the art, and include those described in Merrifield, *Chem. Polypeptides, pp.* 335-61 (Katsoyannis and Panayotis eds.)(1973); Merrifield, *J. Am. Chem. Soc.*, 85:2149 (1963); Davis et al., *Biochem. Intl.*, 10:394-414 (1985); Stewart and Young, *Solid Phase Peptide Synthesis* (1969); U.S. Pat. No. 3,941,763; Finn et al., *The Proteins*, 3rd ed., 2:105-253 (1976); and Erickson et al., *The Proteins*, 3rd ed., 2:257-527 (1976). Solid phase synthesis is the preferred technique of making individual peptides since it is the most cost-effective method of making small peptides.

Phage display is another useful method in generating peptides for use in the present invention. It has been stated that affinity selection from libraries of random peptides can be used to identify peptide ligands for any site of any gene product; Dedman et al., *J. Biol. Chem.*, 268:23025-30 (1993). Phage display is particularly well suited for identifying peptides that bind to such proteins of interest as cell surface receptors or any proteins having linear epitopes; Wilson et al., *Can. J. Microbiol.*, 44:313-29 (1998); Kay et al., *Drug Disc. Today*, 3:370-8 (1998). Such proteins are extensively reviewed in Herz et al., *J. Receptor & Signal Transduction Res.*, 17(5):671-776 (1997), which is hereby incorporated by reference.

The peptides may also be made in transformed host cells using recombinant DNA techniques. To do so, a recombinant DNA molecule coding for the peptide is prepared. Methods of preparing such DNA and/or RNA molecules are well known in the art. For instance, sequences coding for the peptides could be excised from DNA using suitable restriction enzymes. The relevant sequences can be created using the polymerase chain reaction (PCR) with the inclusion of useful restriction sites for subsequent cloning. Alternatively, the DNA/RNA molecule could be synthesized using chemical synthesis techniques, such as the phosphoramidite method. Also, a combination of these techniques could be used.

Additional biologically active agents contemplated for use include recombinant or naturally occurring proteins, whether human or animal, hormones, cytokines, hematopoietic factors, growth factors, antiobesity factors, trophic factors, antiinflammatory factors, and enzymes. Such proteins would include but are not limited to interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), granulocyte-colony stimulating factors (see, U.S. Pat. Nos. 4,810,643, 4,999,291, 5,581,476, 5,582,823, and PCT Publication No. 94/17185, hereby incorporated by reference including drawings), stem cell factor (PCT Publication Nos. 91/05795, 92/17505, and 95/17206, hereby incorporated by reference including drawings), novel erythropoietin stimulating protein (NESP) (PCT Publication No. US94/09257, hereby incorporated by reference including drawings), osteoprotegerin (PCT Publication No. 97/23614, hereby incorporated by reference including drawings), interleukin-1 receptor antagonist (IL-1ra)(PCT Publication Nos. 91/08285 and 92/16221) and leptin (OB protein) (PCT publication Nos. 96/40912, 96/05309, 97/00128, 97/01010 and 97/06816 hereby incorporated by reference including figures).

In addition, biologically active agents can also include but are not limited to insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factors such as osteoprotegerin (OPG), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenetic protein (BMP), superoxide dismutase (SOD), tissue plasminogen activator (TPA), urokinase, streptokinase and kallikrein.

Transthyretin (TTR) contemplated for use in the present invention will have the DNA and amino acid sequences of TTR as reported in Mita et al., *Biochem. Biophys. Res. Commun.*, 124(2):558-564 (1984). These sequences have been deposited in Genbank as accession number K02091. The 127 amino acid TTR sequence used herein does not include the signal sequence (amino acids 1-20) of the K02091 sequence and is depicted below as SEQ ID NO:1.

```
SEQ ID NO: 1
GPTGTGESKCPLMVKVLDAVRGSPAINVAVHVFRKAADDTWEPFASGKTS

ESGELHGLTTEEEFVEGIYKVEIDTKSYWKALGISPFHEHAEVVFTANDS

GPRRYTIAALLSPYSYSTTAVVTNPKE
```

The term "TTR variant" refers to a molecule or sequence that is a modified form of a native TTR. For example, a native TTR comprises sites that may be removed because they provide structural features or biological activity that are not required for the fusion molecules of the present invention. Thus, the term "TTR variant" comprises a molecule or sequence that lacks one or more native TTR sites or residues or that has had one or more native TTR sites or residues replaced with a different amino acid or that has had one or more residues added to the sequence. For purposes of an example, a TTR variant wherein the Alanine residue at amino acid sequence position 37 has been replaced with a Cysteine residue, will be designated TTR variant (A37C); and a TTR variant wherein both the Alanine residue at amino acid sequence position 37 and the Glycine residue at amino acid sequence position 83 have both been replaced with a Cysteine residue will be designated TTR variant (A37C/G83C).

In one embodiment, a TTR or TTR variant fused to a biologically active agent may be fused to a third protein or protein fragment that further stabilizes the TTR-biologically active agent fusion protein, and thereby increases the half-life of the resulting fusion in serum. Examples of such additional proteins or fragments thereof that can be used in such methods and compositions include the Fc domain or CH2 domain of an immunoglobulin, or any other protein domain that one of skill in the art would recognize as having properties that would increase protein stability (see, e.g., Example 29 below). Such protein groups can be fused to the carboxy or amino terminus of the TTR-biologically active agent fusion protein, or can be placed between the TTR and the biologically active agent. It is contemplated that linkers or spacers can be placed, as needed, between each of the domains of the fusion protein to facilitate their desired activity.

In another embodiment, the TTR or TTR variant of the invention can be chemically crosslinked to the biologically active agent. Cross-linking of proteins can be performed by using, for example, N-succinimidyl 3-(2-pyridyldithio) propionate (SPDP) according to established, published procedures. Additional cross-linking agents are readily available and can be identified by one of skill in the art. For details on the above procedure, see, e.g., Karpovsky et al, J. Exp. Med. 160, 1686-1701 (1984); Perez et al, Nature, 316, 354-356 (1985) or Titus et al, Journal of Immunology, 139, 3153-3158 (1987).

In another embodiment, a molecule can be covalently linked to the fusion protein such that stability and/or half-life in serum are increased. For example, a preferred TTR or TTR variant may be chemically modified using water soluble polymers such as polyethylene glycol (PEG). The PEG group may be of any convenient molecular weight and may be straight chain or branched. The average molecular weight of the PEG will preferably range from about 2 kDa to about 100 kDa, more preferably from about 5 kDa to about 50 kDa, most preferably about 20 kDa.

The PEG groups will generally be attached to the compounds of the invention via acylation, reductive alkylation, Michael addition, thiol alkylation or other chemoselective conjugation/ligation methods through a reactive group on the peg moiety (e.g., an aldehyde, amino, ester, thiol, -haloacetyl, maleimido or hydrazino group) to a reactive group on the target compound (e.g., an aldehyde, amino, ester, thiol, -haloacetyl, maleimido or hydrazino group).

Other water soluble polymers used include copolymers of ethylene glycol/propylene glycol, carboxymethylcellulose, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran.

A DNA molecule encoding the peptide of interest, protein of interest, TTR or TTR variant can be prepared using well known recombinant DNA technology methods such as those set forth in Sambrook et al. (*Molecular Cloning: A Labora-*

*tory Manual*, Cold Spring Harbor Laboratory Press, Cold Spring Harbor, N.Y. [1989]) and/or Ausubel et al., eds, *Current Protocols in Molecular Biology*, Green Publishers Inc. and Wiley and Sons, NY (1994). A gene or cDNA encoding the protein of interest or fragment thereof may be obtained for example by screening a genomic or cDNA library with a suitable probe. Suitable probes include, for example, oligonucleotides, cDNA fragments, or genomic DNA fragments, that are expected to have some homology to the gene encoding the protein of interest, such that the probe will hybridize with the gene encoding the protein of interest under selected hybridization conditions. An alternate means of screening a DNA library is by polymerase chain reaction "PCR" amplification of the gene encoding the protein of interest. PCR is typically accomplished using oligonucleotide "primers" which have a sequence that is believed to have sufficient homology to the gene to be amplified such that at least a sufficient portion of the primer will hybridize with the gene.

Alternatively, a gene encoding the peptide of interest or protein of interest may be prepared by chemical synthesis using methods well known to the skilled artisan such as those described by Engels et al., *Angew. Chem. Intl. Ed.*, 28:716-734 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the protein of interest will be several hundred nucleotides in length. Nucleic acids larger than about 100 nucleotides can be synthesized as several fragments using these methods. The fragments can then be ligated together to form a gene coding for the full length protein of interest. Usually, the DNA fragment encoding the amino terminus of the polypeptide will have an ATG, which encodes a methionine residue. This methionine may or may not be present on the mature form of the protein of interest. The methionine can be removed inside the cell or during the process of secretion. Preferred TTR polypeptides may include TTR with the nucleic acid sequence altered to optimize expression in *E. coli* and to introduce convenient restriction sites. A general discussion of codon optimization for expression in *E. coli* is described in Kane, *Curr. Opin. Biotechnol.*, 6:494-500 (1995).

Once the genes encoding the protein of interest and the TTR polypeptide have been obtained, they may be modified using standard methods to create restriction endonuclease sites at the 5' and/or 3' ends. Creation of the restriction sites permits the genes to be properly inserted into amplification and/or expression vectors. Addition of restriction sites is typically accomplished using PCR, where one primer of each PCR reaction typically contains, inter alia, the nucleotide sequence of the desired restriction site.

The gene or cDNA encoding the peptide of interest, or protein of interest can be inserted into an appropriate expression vector for expression in a host cell. The vector is selected to be functional in the particular host cell employed (i.e., the vector is compatible with the host cell machinery such that amplification and/or expression of the gene encoding the protein of interest can occur).

Typically, the vectors used in any of the host cells will contain a promoter (also referred to as a "5' flanking sequence") and other regulatory elements as well such as an enhancer(s), an origin of replication element, a transcriptional termination element, a ribosome binding site element, a polylinker region for inserting the nucleic acid encoding the polypeptide to be expressed, and a selectable marker element. Each of these elements is discussed below. Optionally, the vector may contain a "tag" DNA sequence, i.e., an oligonucleotide sequence located at either the 5' or 3' end of the fusion DNA construct. The tag DNA encodes a molecule such as hexaHis, c-myc, FLAG (Invitrogen, San Diego, Calif.) or another small immunogenic sequence. When placed in the proper reading frame, this tag will be expressed along with the fusion protein, and can serve as an affinity tag for purification of the fusion protein from the host cell. Optionally, the tag can subsequently be removed from the purified fusion protein by various means such as using a selected peptidase for example.

The promoter may be homologous (i.e., from the same species and/or strain as the host cell), heterologous (i.e., from a species other than the host cell species or strain), hybrid (i.e., a combination of promoters from more than one source), synthetic, or it may be the native protein of interest promoter. Further, the promoter may be a constitutive or an inducible promoter. As such, the source of the promoter may be any unicellular prokaryotic or eukaryotic organism, any vertebrate or invertebrate organism, or any plant, provided that the promoter is functional in, and can be activated by, the host cell machinery.

The promoters useful in the vectors of this invention may be obtained by any of several methods well known in the art. Typically, promoters useful herein will have been previously identified by mapping and/or by restriction endonuclease digestion and can thus be isolated from the proper tissue source using the appropriate restriction endonucleases. In some cases, the full nucleotide sequence of the promoter may be known. Here, the promoter may be synthesized using the methods described above for nucleic acid synthesis or cloning.

Where all or only a portion of the promoter sequence is known, the complete promoter may be obtained using PCR and/or by screening a genomic library with suitable oligonucleotide and/or 5' flanking sequence fragments from the same or another species.

Suitable promoters for practicing this invention are inducible promoters such as the lux promoter, the lac promoter, the arabinose promoter, the trp promoter, the tac promoter, the tna promoter, synthetic lambda promoters (from bacteriophage lambda), and the T5 or T7 promoters. Preferred promoters include the lux, and lac promoters.

The origin of replication element is typically a part of prokaryotic expression vectors whether purchased commercially or constructed by the user. In some cases, amplification of the vector to a certain copy number can be important for optimal expression of the protein or polypeptide of interest. In other cases, a constant copy number is preferred. In any case, a vector with an origin of replication that fulfills the requirements can be readily selected by the skilled artisan. If the vector of choice does not contain an origin of replication site, one may be chemically synthesized based on a known sequence, and ligated into the vector.

The transcription termination element is typically located 3' of the end of the fusion protein DNA construct, and serves to terminate transcription of the RNA message coding for the fusion polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

Expression vectors typically contain a gene coding for a selectable marker. This gene encodes a protein necessary for the survival and growth of a host cell grown in a selective culture medium. Typical selection marker genes encode proteins that (a) confer resistance to antibiotics or other toxins, e.g., ampicillin, tetracycline, chloramphenicol, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, the chloramphenicol resistance gene, and the tetracycline resistance gene.

The ribosome binding element, commonly called the Shine-Dalgarno sequence in prokaryotes, is necessary for the initiation of translation of mRNA. The element is typically located 3' to the promoter and 5' to the coding sequence of the fusion protein DNA construct. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

Each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting can be accomplished by first filling in "sticky ends" using an enzyme such as Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

Another method for constructing the vector is to conduct all ligations of the various elements simultaneously in one reaction mixture. Here, many nonsense or nonfunctional vectors may be generated due to improper ligation or insertion of the elements, however the functional vector may be identified by expression of the selectable marker. Proper sequence of the ligation product can be confirmed by digestion with restriction endonucleases or by DNA sequencing.

After the vector has been constructed and a fusion protein DNA construct has been inserted into the proper site of the vector, the completed vector may be inserted into a suitable host cell for fusion protein expression.

Host cells suitable for the present invention are bacterial cells. For example, the various strains of *E. coli* (e.g., HB101, JM109, DH5α, DH10, and MC1061) are well-known host cells for use in preparing recombinant polypeptides. The choice of bacterial strain is typically made so that the strain and the expression vector to be used are compatible. Various strains of *B. subtilis, Pseudomonas* spp., other *Bacillus* spp., *Streptomyces* spp., and the like may also be employed in practicing this invention in conjunction with appropriate expression vectors.

Insertion (also referred to as "transformation" or "transfection") of the vector into the selected host cell may be accomplished using such methods as calcium phosphate precipitation or electroporation. The method selected will in part be a function of the type of host cell to be used. These methods and other suitable methods are well known to the skilled artisan, and are set forth, for example, in Sambrook et al., supra.

The host cells containing the vector (i.e., transformed or transfected host cells) may be cultured using one or more standard media well known to the skilled artisan. The selected medium will typically contain all nutrients necessary for the growth and survival of the host cells. Suitable media for culturing *E. coli* cells, are, for example, Luria broth ("LB"), YT broth, SOB, SOC, and/or Terrific Broth ("TB").

There are several ways to prepare the DNA construct encoding the fusion protein which comprises the TTR gene, the gene encoding the peptide or protein of interest, and, optionally, a DNA molecule encoding a linker peptide which is located between the two genes.

In one procedure, the TTR gene and gene encoding the protein of interest (the "fusion partner genes") can be ligated together in either orientation (e.g., TTR gene at the 5' or 3' end of the construct). Where a linker DNA molecule is to be included, it can first be ligated to one of the fusion partner genes, and that construct can then be ligated to the other fusion partner gene. Ligations are typically accomplished using DNA ligase enzyme in accordance with the manufacturer's instructions.

A separate procedure provides for first ligating one fusion partner gene into the selected vector, after which the other fusion partner gene can be ligated into the vector in a position that is either 3' or 5' to the first fusion partner gene. Where a linker DNA molecule is to be included, the linker DNA molecule may be ligated to either fusion partner gene either before or after that gene has been ligated into the vector.

The TTR-TMPs of the present invention can be used to treat conditions generally known as those that involve an existing megakaryocyte/platelet deficiency or an expected megakaryocyte/platelet deficiency (e.g., because of planned surgery or platelet donation). Such conditions will usually be the result of a deficiency (temporary or permanent) of active Mpl ligand in vivo. The generic term for platelet deficiency is thrombocytopenia, and hence the methods and compositions of the present invention are generally available for treating thrombocytopenia in patients in need thereof. Thrombocytopenia (platelet deficiencies) may be present for various reasons, including chemotherapy and other therapy with a variety of drugs, radiation therapy, surgery, accidental blood loss, and other specific disease conditions.

Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, a compound of the present invention could be administered several days to several hours prior to the need for platelets. With regard to acute situations, e.g., accidental and massive blood loss, a compound of this invention could be administered along with blood or purified platelets.

The TMP compounds of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

The TMP compounds of this invention may be used in any situation in which production of platelets or platelet precursor cells is desired, or in which stimulation of the c-Mpl receptor is desired. Thus, for example, the compounds of this invention may be used to treat any condition in a mammal wherein there is a need of platelets, megakaryocytes, and the like. Such conditions are described in detail in the following exemplary sources: WO95/26746; WO95/21919; WO95/18858; WO95/21920 and are incorporated herein.

The TMP compounds of this invention may also be useful in maintaining the viability or storage life of platelets and/or megakaryocytes and related cells. Accordingly, it could be useful to include an effective amount of one or more such compounds in a composition containing such cells.

The therapeutic methods, compositions and compounds of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that the inventive compound will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), SCF, GM-CSF, granulocyte colony stimulating factor (G-CSF), EPO, interferon-alpha (IFN-alpha), consensus interferon, IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of an inventive compound (to enhance the number of mature megakaryocytes) followed by administration of the soluble Mpl receptor (to inactivate the ligand and allow the mature megakaryocytes to produce platelets) is expected to be a particularly effective means of stimulating platelet production. The appropriate dosage would be adjusted to compensate for such additional components in the therapeutic composition. Progress of the treated patient can be monitored by conventional methods.

In non-insulin dependent diabetes mellitus (NIDDM), also known as type 2 diabetic patients, the administration of glucagon-like peptide-1 (GLP-1) has antidiabetic properties. However, GLP-1 is rapidly degraded by dipeptidyl peptidase IV (DPPIV) after its release in vivo. Thus, it is an advantage of the present invention that a GLP-1 peptide or variant thereof can be fused to a TTR polypeptide of the invention to stabilize GLP-1 and increase its half life in vivo. Accordingly, in another embodiment of the invention, a TTR-GLP1 fusion protein as described herein can be used to treat conditions generally known to involve non-insulin dependent diabetes mellitus (NIDDM), which is also known as type II diabetes.

One of skill in the art will recognize that the sequence of a GLP-1 peptide can be varied such that it retains its insulinotropic effects. Particular examples of such variations known in the art include, for example, GLP-1 (7-34), (7-35), (7-36) or (7-37), Gln$^9$-GLP-1 (7-37), D-Gln$^9$-GLP-1 (7-37), Thr$^{16}$-Lys$^{18}$-GLP-1 (7-37), and Lys$^{18}$-GLP-1 (7-37). Additional examples of GLP-1 variants are described in U.S. Pat. Nos. 5,118,666, 5,545,618, 5,977,071, and WO 02/46227 and in Adelhorst et al., J. Biol. Chem. 269:6275 (1994), which are incorporated by reference. Accordingly, any GLP-1 peptide can be used to generate fusion proteins of the invention, as long as the GLP-1 fusion protein is capable of binding and inducing a signal through it's cognate receptor. Receptor binding and activation can be measured by standard assays (U.S. Pat. No. 5,120,712).

The dose of fusion protein effective to normalize a patient's blood glucose will depend on a number of factors among which are included the subject's weight, age, severity of their inability to regulate blood glucose, the route of administration, the bioavailability, the pharmokinetic profile of the fusion protein and the formulation as is discussed more fully below.

The therapeutic methods, compositions and compounds of the present invention may also be employed, alone or in combination with other diabetes treatments, including but not limited to insulin, DPPIV-inhibitors and the like. The dosage of the GLP-1 fusion protein would be adjusted to compensate for such additional components in the therapeutic composition. Progress of the treated patient can be monitored by conventional methods, such as, for example, the monitoring of blood glucose levels.

The present invention also provides pharmaceutical compositions of the inventive compounds. Such pharmaceutical compositions may be for administration for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation, e.g., embedded under the splenic capsule, brain, or in the cornea. The treatment may consist of a single dose or a plurality of doses over a period of time. In general, comprehended by the invention are pharmaceutical compositions comprising effective amounts of a compound of the invention together with pharmaceutically acceptable diluents, preservatives, stabilizers, solubilizers, emulsifiers, adjuvants and/or carriers. Such compositions include diluents of various buffer content (e.g., Tris-HCl, acetate, phosphate, citrate, etc.), pH and ionic strength; additives such as detergents and solubilizing agents (e.g., Tween 80, Polysorbate 80, etc.), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. The pharmaceutical compositions optionally may include still other pharmaceutically acceptable liquid, semisolid, or solid diluents that serve as pharmaceutical vehicles, excipients, or media, including but are not limited to, polyoxyethylene sorbitan monolaurate, magnesium stearate, methyl- and propylhydroxybenzoate, starches, sucrose, dextrose, gum acacia, calcium phosphate, mineral oil, cocoa butter, and oil of theobroma. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712 which are herein incorporated by reference. The compositions may be prepared in liquid form, or may be in dried powder, such as lyophilized form. Implantable sustained release formulations are also contemplated, as are transdermal formulations.

Controlled release formulation may be desirable. The drug could be incorporated into an inert matrix which permits release by either diffusion or leaching mechanisms e.g., gums. Slowly degenerating matrices may also be incorporated into the formulation, e.g., alginates, polysaccharides. Another form of a controlled release of this therapeutic is by a method based on the Oros therapeutic system (Alza Corp.), i.e., the drug is enclosed in a semipermeable membrane which allows water to enter and push drug out through a single small opening due to osmotic effects. Some enteric coatings also have a delayed release effect.

Also contemplated herein is pulmonary delivery of the present protein (or derivatives thereof). The protein (or derivative) is delivered to the lungs of a mammal while inhaling and traverses across the lung epithelial lining to the blood stream. (Other reports of this include Adjei et al., Pharmaceutical Research 7:565-569 (1990); Adjei et al., International Journal of Pharmaceutics 63:135-144 (1990)(leuprolide acetate); Braquet et al., Journal of Cardiovascular Pharmacology 13 (suppl. 5): s.143-146 (1989)(endothelin-1); Hubbard et al., Annals of Internal Medicine 3:206-212 (1989)(1-antitrypsin); Smith et al., J. Clin. Invest. 84:1145-1146 (1989) (1-proteinase); Oswein et al., "Aerosolization of Proteins", Proceedings of Symposium on Respiratory Drug Delivery II, Keystone, Colo., March, 1990 (recombinant human growth hormone); Debs et al., The Journal of Immunology 140:3482-3488 (1988)(interferon- and tumor necrosis factor ) and Platz et al., U.S. Pat. No. 5,284,656 (granulocyte colony stimulating factor).

Contemplated for use in the practice of this invention are a wide range of mechanical devices designed for pulmonary delivery of therapeutic products, including but not limited to nebulizers, metered dose inhalers and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the inventive compound. Typically, each formulation is specific to the type of device employed and may involve the use of an appropriate propellant material, in addition to diluents, adjuvants and/or carriers useful in therapy.

The inventive compound should most advantageously be prepared in particulate form with an average particle size of less than 10 µm (or microns), most preferably 0.5 to 5 µm, for most effective delivery to the distal lung.

Carriers include carbohydrates such as trehalose, mannitol, xylitol, sucrose, lactose, and sorbitol. Other ingredients for use in formulations may include DPPC, DOPE, DSPC and DOPC. Natural or synthetic surfactants may be used. Polyethylene glycol may be used (even apart from its use in derivatizing the protein or analog). Dextrans, such as cyclodextran, may be used. Bile salts and other related enhancers may be used. Cellulose and cellulose derivatives may be used. Amino acids may be used, such as use in a buffer formulation.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the dose should be in the range of 0.1 µg to 100 mg of the inventive compound per kilogram of body weight per day, preferably 0.1 to 1000 µg/kg; and more preferably 0.1 to 150 µg/kg, given in daily doses or in equivalent doses at longer or shorter intervals, e.g., every other day, twice weekly, weekly, or twice or three times daily.

The inventive compounds may be administered by an initial bolus followed by a continuous infusion to maintain therapeutic circulating levels of drug product. As another example, the inventive compounds may be administered as a one-time dose. Those of ordinary skill in the art will readily optimize effective dosages and administration regimens as determined by good medical practice and the clinical condition of the individual patient. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Depending on the route of administration, a suitable dose may be calculated according to body weight, body surface area or organ size.

Appropriate dosages may be ascertained through use of established assays for determining serum levels in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels and duration of treatment for various diseases and conditions.

The following Examples are intended for illustration purposes only, and should not be construed to limit the invention in any way.

EXAMPLE 1

This example describes the preparation of DNA for native recombinant human transthyretin (TTR) and the following TTR variants: TTR(C10A), TTR(C10A/A37C), TTR(C10A/D38C), TTR(C10A/A81C), TTR(C10A/G83C), and TTR (C10A/K15A/G83C).

The expression plasmid pAMG21 is available from the ATCC under accession number 98113, which was deposited on Jul. 24, 1996 (see PCT WO 97/23614, published 3 Jul. 1997 for a description of pAMG21). DNA sequence coding for TTR, TTR variants or TTR-peptide fusions was placed under control of the LuxPR promoter in pAMG21.

The bacterial host GM221 is an $E.$ $coli$ K-12 strain that has been modified to contain both the temperature sensitive lambda repressor cI857s7 in the early ebg region and the lacI$^Q$ repressor in the late ebg region (68 minutes). The presence of these two repressor genes allows the use of this host with a variety of expression systems, however both of these repressors are irrelevant to the expression from luxP$_R$. The untransformed host has no antibiotic resistances. The ribosomal binding site of the cI857s7 gene has been modified to include an enhanced RBS. It has been inserted into the ebg operon between nucleotide position 1170 and 1411 as numbered in Genbank accession number M64441Gb_Ba with deletion of the intervening ebg sequence. The construct was delivered to the chromosome using a recombinant phage called MMebg-cI857s7 enhanced RBS #4 into F'tet/393. After recombination and resolution only the chromosomal insert described above remains in the cell. It was renamed F'tet/GM101. F'tet/

GM101 was then modified by the delivery of a lacI$^Q$ construct into the ebg operon between nucleotide position 2493 and 2937 as numbered in the Genbank accession number M64441Gb_Ba with the deletion of the intervening ebg sequence. The construct was delivered to the chromosome using a recombinant phage called λGebg-lacI$^Q$ #5 into F'tet/GM101. After recombination and resolution only the chromosomal insert described above remains in the cell. It was renamed F'tet/GM221. The F'tet episome was cured from the strain using acridine orange at a concentration of 25 µg/ml in LB. The cured strain was identified as tetracyline sensitive and was stored as GM221.

Oligonucleotides (1.0 nm each) were synthesized by phosphoramidite method. Nucleotides were, in some cases, altered for optimized expression in E. coli. These codon changes did not result in changes in the amino acid sequence. Each of the oligonucleotides utilized in this example are listed in Table 1.

PCR was performed with the Expand Long Polymerase according to the manufacturer's protocol (Boehringer Mannheim). PCR products were verified by agarose gel electrophoresis, purified and digested with NdeI and XhoI (New England Biolabs). Expression vector pAMG21 was digested in the same manner and then treated with calf intestinal phosphatase (Boehringer Mannheim). The vector and insert were purified from an agarose gel, then mixed and ligated by T4 DNA ligase (New England Biolabs). Ligation was done at 4° C. for 2 hrs. Each ligation mixture was transformed by electroporation into the host strain GM221 described above with a Biorad GenePulser (Biorad Laboratories) using 2.5V, 25 uFD, and 200 ohms in a cuvette with a gap length of about 2 mm. After electroporation, the cells were allowed to recover in 1 ml of Luria broth (LB) for about one hour at 37° C. with gentle shaking. The entire transformation mix was plated on LB agar containing 50 ug/ml kanamycin. Colonies were screened for presence of the desired molecular weight by PCR using oligonucleotides directed against flanking vector sequence. The PCR products were evaluated by agarose gel electrophoresis. Positive clones were further screened for the ability to produce the recombinant protein product and finally verified by nucleotide sequencing.

The DNA and amino acid sequences of TTR are known (Mita, S et al., Biochem. Biophys. Res. Commun. 124 (2), 558-564 [1984]). These sequences have been deposited in Genbank as accession number K02091. The cDNA of native TTR excluding the signal peptide was cloned from a cDNA library derived from human liver (Clontech). Specifically, an oligonucleotide encoding eight codons of the TTR 5' (Oligo 2693-79) end and an oligonucleotide encoding seven codons of TTR 3' end including a terminating codon (Oligo 2693-80) were synthesized and used to amplify the full-length mature TTR with Expand Long polymerase using human liver cDNA library as template. The resulting PCR fragment was digested with NdeI and XhoI, gel purified and ligated with NdeI/XhoI restricted expression vector pAMG21. After 2 hours at 4° C., the ligation mixture was electroporated into GM221 cells. Single colonies were picked and plasmid DNA was prepared and sequenced. One resulting plasmid (strain #5316) was shown to have the correct DNA sequence of native TTR (plus a methionine at the N-terminus) and was used for expression. This DNA sequence is identified in SEQ ID NO:2.

Mutant TTR(C10A) was made by using oligonucleotide 2693-80 above and oligonucleotide 2820-88 (encompasses the first 11 codons of native TTR in which the codon Cys at the tenth position was changed to Ala). The PCR procedure and the process for selecting the expression strain were similar to that described above. The resulting strain (strain #5619) had the DNA sequence identified in SEQ ID NO:3.

Plasmid 5619 was further modified by replacing the amino acids at the following positions: A37, D38, A81 and G83, with the amino acid Cysteine. As described below, each pair of the complementary oligonucleotides harboring the desired mutations was used in conjunction with TTR 5' and 3' primers described above in a standard two-step PCR procedure designed for site-specific mutagenesis. Each of the forward primers were used with a TTR 3' primer and each of the reverse primers were used with a TTR 5' primer in a 20-cycle PCR in which plasmid derived from strain 5619 was used as the template. The resulting PCR amplified 5' and 3' fragments were mixed and used as the template for the second step PCR to generate the full-length mutants. Subsequent cloning and sequencing procedures were similar to those already described. The following oligonucleotides were utilized: TTR(A37C) forward (Oligo 2823-91); TTR(A37C) reverse (Oligo 2823-92); TTR(D38C) forward (Oligo 2823-93); TTR (D38C) reverse (Oligo 2823-94); TTR(A81C) forward (Oligo 2823-95); TTR(A81C) reverse (Oligo 2823-96); TTR (G83C) forward (Oligo 2823-97); TTR(G83C) reverse (Oligo 2823-98).The resulting E. coli strains containing the plasmids are described as follows: TTR(C10A/A37C)(strain 5641) had the DNA sequence identified in SEQ ID NO:4. TTR(C10A/D38C)(strain 5642) had the DNA sequence identified in SEQ ID NO:5. TTR(C10A/A81C)(strain 5643) had the DNA sequence identified in SEQ ID NO:6. TTR(C10A/G83C)(strain 5651) had the DNA sequence identified in SEQ ID NO:7.

The Lys in the 15th position in strain 5651 was further mutagenized to Ala using oligonucleotides 2953-67 and 2953-68 by a procedure similar to that described for strains 5641, 5642, 5643 and 5651.

The resulting strain, TTR(C10A/K15A/G83C)(strain 5895) had the DNA sequence identified in SEQ ID NO:8.

TABLE 1

| Oligo | Sequence | SEQ ID Number |
|---|---|---|
| 2693-79 | GAGGAATAACATATGGGTCCAACTGGTACCGGTGAA | 18 |
| 2693-80 | CCGCGGATCCTCGAGATTATTCCTTGGGATTGGTGA | 19 |
| 2820-88 | GAGGAATAACATATGGGTCCAACTGGTACCGGTGAA TCCAAGGCTCCT | 20 |
| 2823-91 | AGAAAGGCTTGTGATGACACCTGG | 21 |
| 2823-92 | CCAGGTGTCATCACAAGCCTTTCT | 22 |
| 2823-93 | AGAAAGGCTGCTTGTGACACCTGG | 23 |
| 2823-94 | CCAGGTGTCACAAGCAGCCTTTCT | 24 |
| 2823-95 | TACTGGAAGTGTCTTGGCATCTCC | 25 |
| 2823-96 | GGAGATGCCAAGACACTTCCAGTA | 26 |
| 2823-97 | AAGGCACTTTGCATCTCCCCATTC | 27 |
| 2823-98 | GAATGGGGAGATGCAAAGTGCCTT | 28 |
| 2953-67 | CTGATGGTCGCAGTTCTAGAT | 29 |
| 2953-68 | ATCTAGAACTGCGACCATCAG | 30 |

EXAMPLE 2

This example describes the preparation of various TMP-TTR fusions. Several fusion proteins containing TTR and a TMP were prepared. Each of the oligonucleotides utilized in this example are listed in Table 2.

A fragment containing the TMP was first amplified from a strain harboring a plasmid encoding a full-length TMP-Fc fusion (see PCT Publication No. 00/24770) using oligonucleotides 2743-96 which encodes the first 7 codons of the TMP plus a 12 nucleotide 5' extension including a Nde1 site and 2743-97 which encodes the first 7 codons of native TTR and the last 7 codons of the TMP of interest. The resulting PCR fragment was mixed with plasmid derived from strain 5619 and the mixture was used as a template for oligonucleotide primers 2743-96 and 2693-80 to amplify full-length TMP-TTR. Similar procedures described above were used for cloning and expression. The resulting strain, TMP-TTR (strain 5513) had the DNA sequence identified in SEQ ID NO:9.

The TMP was then introduced to the N-terminus of strains 5641, 5642, 5643 and 5651, respectively. Plasmid 5513 was digested with Xba1, the resulting Xba1/Xba1 insert containing the TMP and the first 18 codons of TTR(C10A) was gel purified and ligated with Xba1 restricted, phosphatase treated and gel purified vector derived from 5641, 5642, 5643 and 5651. DNA sequencing was performed to select the correct orientation for each fusion. The resulting *E. coli* strains containing the plasmids are described as follows: TMP-TTR (C10A/A37C)(strain 5704) had the DNA sequence identified in SEQ ID NO:10. TMP-TTR(C10A/D38C)(strain 5705) had the DNA sequence identified in SEQ ID NO:11. TMP-TTR (C10A/A81C)(strain 5706) had the DNA sequence identified in SEQ ID NO:12. TMP-TTR(C10A/G83C)(strain 5707) had the DNA sequence identified in SEQ ID NO:13.

TABLE 2

| Oligo | Sequence | SEQ ID Number |
|---|---|---|
| 2743-96 | GAGGAATAACATATGATCGAAGGTCCGACTCTGCGT | 31 |
| 2743-97 | TTCACCGGTACCAGTTGGACCTGCGCGTGCTGCAAG CCATT | 32 |

EXAMPLE 3

This example describes the preparation of PTH (1-34)-TTR(C10A/K15A/G83C) fusion. Each of the oligonucleotides utilized in this example are listed in Table 3.

Two new oligonucleotides, oligonucleotide 2694-01, which encodes the first 7 codons of human PTH, and oligonucleotide 2694-03, which encodes the first 7 codons of TTR and amino acids 28-34 of PTH, were synthesized to make the fusion. Oligonucleotides 2694-01 and 2694-03 were used in a 20-cycle PCR procedure as described above to amplify PTH (1-34) with the TTR linker. The template for this reaction was a strain which harbors a plasmid encoding a PTH1-34-Fc fusion (see PCT Publication No. 01/81415). The resulting PCR mixture was combined with strain 5895 and used as the template to amplify the full length PTH (1-34)-TTR(C10A/K15A/G83C) using primers 2694-01 and 2693-80. After sequence confirmation, the resulting expression strain containing the new plasmid was designated PTH-TTR(C10A/K15A/G83C)(strain 5920) and had the DNA sequence identified in SEQ ID NO:14.

TABLE 3

| Oligo | Sequence | SEQ ID Number |
|---|---|---|
| 2694-01 | GAGGAATAACATATGTCTGTTTCTGAAATCCAG | 33 |
| 2694-03 | TTCACCGGTACCAGTTGGACCAAAGTTATGAACGTC | 34 |

EXAMPLE 4

This example describes the preparation of an IL-1ra-TTR (C10A) fusion and a TTR(C10A)-GSGS-IL-1ra fusion. Each of the oligonucleotides utilized in this example are listed in Table 4.

To prepare the IL-1ra-TTR(C10A) fusion, two oligonucleotides, oligonucleotide 2823-13, which encodes the first 7 codons of the human protein IL-1ra, and oligonucleotide 2823-14, which encodes the last 7 amino acids of IL-1ra and the first 7 amino acids of TTR, were synthesized. The plasmid derived from a strain which expresses IL-1ra (see PCT Publication No. 91/08285) was amplified using oligonucleotides 2823-13 and 2823-14. The resulting PCR product was mixed with plasmid purified from strain 5619 and used as a template to amplify full-length IL-1-ra-TTR(C10A) using oligonucleotide primers 2823-13 and 2693-80. The PCR product was cloned, sequenced and expressed as described above. The resultant strain containing the new plasmid was designated IL-1ra-TTR(C10A) (strain 5644) and had the DNA sequence identified in SEQ ID NO:15.

To make TTR(C10A)-IL-1ra, the following two oligonucleotides, oligonucleotide 2787-32, which encodes the last 7 amino acids of TTR, the first 7 amino acids of IL-1-ra between which a GSGS linker was introduced, and oligonucleotide 2787-33, which encodes the last 7 codons of IL-1-ra, were synthesized. These two oligonucleotide primers were used to amplify plasmid 2693, and the resulting PCR product was mixed with plasmid 5619, and together these were used as a template to amplify full-length TTR(C10A)-IL-1ra using primers 2787-33 and 2693-79. The PCR product was cloned, sequenced and expressed as described above. The resultant strain containing the new plasmid was designated TTR(C10A)-IL-1ra (strain 5645) and had the DNA sequence identified in SEQ ID NO:16.

TABLE 4

| Oligo | Sequence | SEQ ID Number |
|---|---|---|
| 2823-13 | GAGGAATAACATATGCGACCGTCCGGACGTAA | 35 |
| 2823-14 | TTCTACTTCCAGGAAGACGAAGGTCCAACTGGTACC | 36 |
| 2787-32 | GTCGTCACCAATCCCAAGGAAGGTAGTGGTAGCCGA CCGTCCGGCCGTAAGAGC | 37 |
| 2787-33 | CCGCGGATCCTCGAGATTATTCGTCTTCCTGGAAGT AGAA | 38 |

EXAMPLE 5

This example describes the preparation of TTR(C10A/G83C)-Bradykinin. Each of the oligonucleotides utilized in this example are listed in Table 5.

Plasmid purified from strain 5651 was used for PCR with oligonucleotide primer 2693-79 and oligonucleotide primer 2943-47, which is a TTR 3' primer containing a PstI restriction site. This PCR product was gel purified and restriction digested with NdeI and PstI. The resulting DNA fragment was used in a ligation mixture containing AMG21, digested with NdeI and XhoI, and the annealed oligonucleotide linkers 2943-48, which encodes the GSGSG linker, and oligonucleotide 2943-49, which encodes the Bradykinin antagonist peptide KRPPGFSPL with PstI 5' and XhoI 3' overlapping ends. GM121 was transformed with this ligation product and DNA was purified from the kanamycin resistant colonies. The DNA sequence was then confirmed in the resistant colonies. The confirmed strain was grown at 30° C. and induced for expression in a 10-liter fermentation described below. The new strain was designated TTR(C10A/G83C)-Bradykinin (strain 5914) and had the DNA sequence identified in SEQ ID NO:17.

TABLE 5

| Oligo | Sequence | SEQ ID Number |
| --- | --- | --- |
| 2693-79 | GAGGAATAACATATGGGTCCAACTGGTACCGGTGAA | 39 |
| 2943-47 | AATATACTGCAGTGGTGGAATAGGAG | 40 |
| 2943-48 | GTCGTCACCAATCCCAAGGAAGGATCAGGATCCGGA AAACGTCCGCCGGGTTTCTCCCCGCTGTAATC | 41 |
| 2943-49 | TCGAGATTACAGCGGGGAGAAACCCGGCGGACGTTT TCCGGATCCTGATCCTTCCTTGGGATTGGTGACGAC TGCA | 42 |

EXAMPLE 6

This example describes the recombinant expression of TTR and the TTR fusion constructs in E. coli. Each of the newly constructed TTR or TTR fusions were first examined for soluble expression at temperatures ranging from 16° C. to 37° C. For this purpose, cultures (25 ml) of GM221 expressing each of the TTR or TTR fusions were grown in LB medium supplemented with 50 µg/ml kanamycin at 37° C. until the optical density (OD) at 600 nm reached 0.5 to 1.0. The cultures were then placed in shakers with temperature settings at 16° C., 20° C., 25° C., 30° C., 34° C. and 37° C., respectively. The induction of gene product expression from the luxPR promoter was achieved following the addition of the synthetic autoinducer N-(3-oxohexanoyl)-DL-homoserine lactone to the culture media to a final concentration of 20 ng/ml. After 6 hours, the bacterial cultures were examined by microscopy for the presence of inclusion bodies. Often soluble or partial soluble expression could be achieved by growing the cultures at temperatures lower than 30° C. for TTR and its fusions, and this temperature was used for large-scale expression. In cases where soluble expression could not be achieved, temperatures at which the level of expression was at the highest were used for large-scale shakers or fermentors.

Large-scale expression was normally done in 4 liter flasks. Four to eight 4 liter shakers containing 1 liter of LB was inoculated with overnight cultures of TTR or its fusion strains. Expression was done essentially as described above. Cells were collected by centrifugation.

The fermentation stage, employing aseptic technique, begins with the inoculation from a seed culture of strains produced in a shake flask containing 500 mL of sterilized Luria broth. When this culture obtained the appropriate cell density (0.8-2 at 600 nm), the contents were used to inoculate a 20 liter fermentor containing 10 liter of complex based growth medium. The fermentor is maintained at 30° C. and pH 7 with dissolved oxygen levels kept at 30% saturation. When the cell density reached an optical density of 10-12 OD units at 600 nm, at which point the culture was induced by the addition of N-(3-oxo-hexanoyl) homoserine lactone. At 6 hours post-induction the cells were harvested from the fermentor by centrifugation.

EXAMPLE 7

This example describes the purification of TTR(C10A/G83C)-Bradykinin. About 193 g of E. coli paste from clone 5914 stored at −80° C. was defrosted in 1447 ml of 50 mM tris HCl, 5 mM EDTA, pH 8.0. 50 tablets of Sigma protease inhibitor cocktail 1-873-580 (Saint Louis, Mo.) was dissolved in the cell suspension and the suspension was passed through a model 110-Y microfluidizer (Microfluidics, Newton, Mass.) twice at 12,000 PSI. The lysate (FIG. 1, Lane 2) was centrifuged at 11,325×g for 50 min 4° C. The supernatant was removed as the soluble fraction. The soluble fraction was heated in a 65° C. water bath for 30 minutes in polypropylene bottles, at which time the temperature of the contents was 63° C. The soluble fraction was centrifuged at 11,325×g for 50 minutes 4° C. The supernatant was removed as Heat Soluble (FIG. 1, Lane 3). The heat soluble fraction was filtered through a 0.45 µm cellulose acetate filter with two prefilters and then loaded on to a 240 ml Q-sepharose fast flow (5 cm ID) column (Amersham Pharmacia Biotech, Piscataway, N.J.) at 20 ml/min equilibrated in Q-Buffer A (20 mM tris HCl, 2.5 mM EDTA, pH 8.0) at room temperature (about 23° C.). Column was washed with about 2300 ml Q-Buffer A at 20 ml/min. Q-column was eluted with a 15 column volume linear gradient to 60% Q-Buffer B (20 mM tris HCl, 1 M NaCl, 2.5 mM EDTA, pH 8.0) followed by a 2 column volume step to 100% Q-Buffer B. Fractions containing the TTR fusion as determined by SDS-PAGE were pooled into a single Q-pool (1150 ml) (FIG. 1, Lane 4) and 1.77 g of DTT was added. The Q-pool was gently stirred for 30 min at room temperature (about 23° C.). To the Q-pool, 410 ml of 3.8 M ammonium sulfate pH 7.0 was slowly added and the pH was lowered from about 7.5 to 7.0 by slow addition of 1 M HCl. About one-half of the Q-pool was then loaded on to an 84 ml phenyl sepharose high performance column (2.6 cm ID) (Amersham Pharmacia Biotech) in P-Buffer A (50 mM NaH$_2$PO$_4$, 1 M ammonium sulfate, pH 7.0) at 10 ml/min. The column was washed with about 170 ml P-Buffer A followed by three step elutions using 50%, 80%, and 100% P-Buffer B (50 mM NaH$_2$PO$_4$, pH 7.0). The remaining half of the Q-pool was then processed using the same protocol as the first half. Fractions containing the TTR fusion as determined by SDS-PAGE were pooled into a single P-pool (260 ml) (FIG. 1, Lane 5) and the P-pool was dialyzed against 4 L of HA-Buffer A (10 mM NaH$_2$PO$_4$, pH 7.0) for 2 hours at room temperature (about 23° C.) using 20.4 mm diameter 8 kDa cutoff dialysis tubing (Spectrum Laboratories Inc., Rancho Dominguez, Calif.). The dialysis buffer was changed with a fresh 4 L of HA-Buffer A and dialysis was continued for approximately an additional 15 hours. The P-pool was removed from dialysis and 600 µl of 1 M DTT was added followed by incubation at room temperature (about 23° C.) for about 1 hour. P-pool was loaded on to a 105 ml (2.6 cm) type 1 ceramic hydroxyapatite column (Bio-Rad Inc., Hercules, Calif.) at 10 ml/min in HA-Buffer A. Column was washed with approximately 210 ml HA-Buffer A at 10 ml/min followed by 4 steps of 12.5%, 25%, 50%, and 100% HA-Buffer B (400 mM NaH$_2$PO$_4$, pH 7.0). The flowthrough was pooled as HA-pool (340 ml) (FIG.

1, Lane 6) and 524 mg of DTT was added followed by incubation at room temperature (about 23° C.) for 1 hour.

About one-half of the HA-pool was loaded on to a 47 ml source 15Q (2.6 cm ID) column (Amersham Pharmacia Biotech) at 10 ml/min followed by a wash with about 250 ml Q-Buffer A. Column was eluted with a 20 column volume linear gradient from 10% to 50% Q-Buffer B followed by a step of 2 column volumes of 100% Q-Buffer B. The remaining half of the HA-Pool was then processed using the same protocol as the first half. Fractions containing the TTR fusion as determined by SDS-PAGE were pooled into a single Q2-pool (260 ml) and concentrated to about 75 ml using a stirred cell with a 10 kDa membrane. Q2-pool (FIG. 1, Lane 7) was then filtered through a 0.22 μm cellulose acetate filter and the protein concentration was determined to be 16.9 mg/ml using a calculated extinction coefficient of 18,450 $M^{-1}$ $cm^{-1}$. The pyrogen level was determined to be <1 EU/mg of protein using the Limulus Ameboycyte Lysate assay (Associates of Cape Cod, Falmouth, Mass.). The nucleic acid content was determined to be negligible, since the ratio of the absorbance at 260 nm over 280 nm was determined to be 0.52.

EXAMPLE 8

Figure 2:
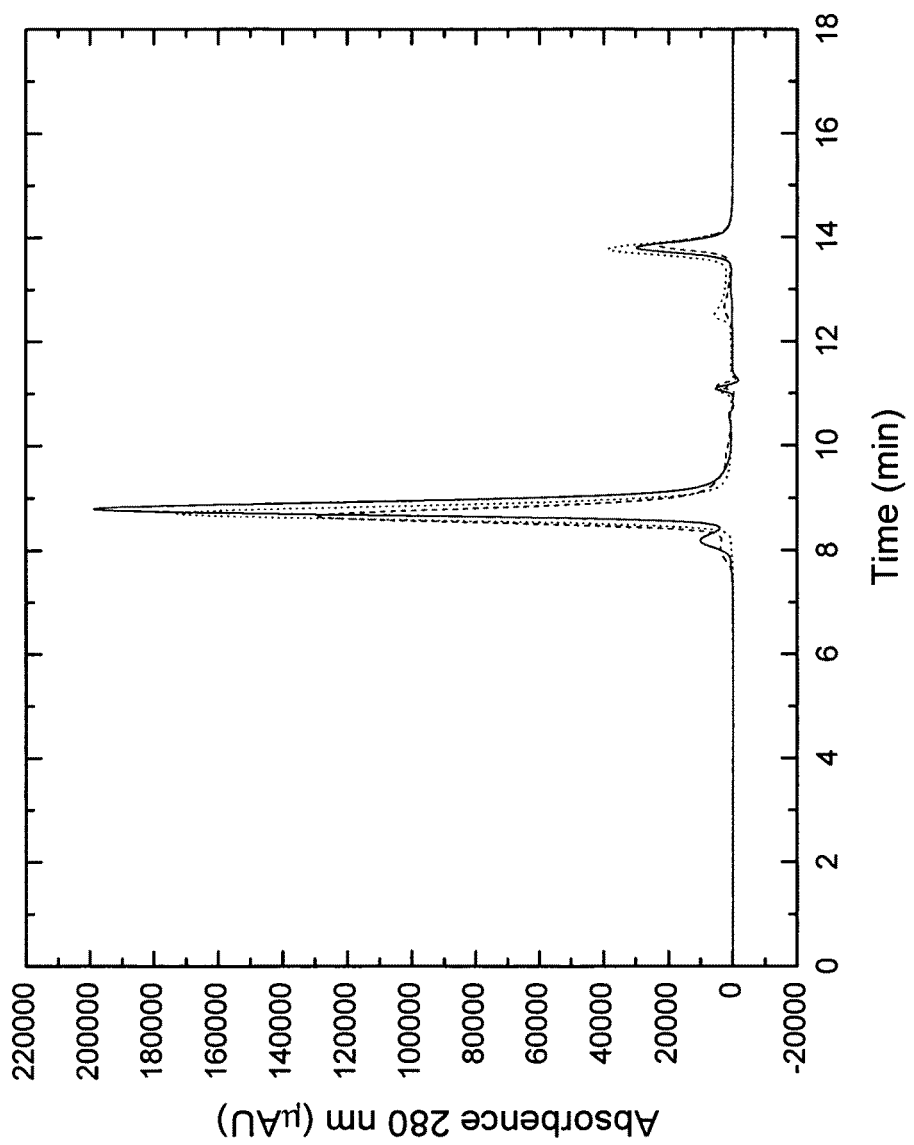
FIG. 2 demonstrates by size exclusion chromatography that fusion of peptides to the amino-terminus or carboxy-terminus of a TTR variant, TTR(C10A/G83C), does not alter its oligomeric structure. Solid line is TTR(C10A/G83C), dashed line is parathyroid hormone (PTH) fused to the amino-terminus of TTR(C10A/G83C), and the dotted line is Bradykinin fused to the carboxy-terminus of TTR(C10A/G83C).

This example demonstrates that fusing a peptide to either the C-terminus or N-terminus of TTR(C10A/G83C)does not have a significant impact on its oligomeric structure. TTR (C10A/G83C), PTH-TTR(C10A/K15A/G83C), and TTR (C10A/G83C)-Bradykinin in 20 mM tris pH 8.0 and about 250 mM NaCl were reduced with 9 mM DTT for about 1 hour at room temperature (about 23° C.). About 50 μg of the reduced TTR was injected on to a Biosep-Sec-S 3000 column (7.8 mm ID×300 mm) (Phenomenex, Torrance, Calif.) in SEC-Buffer (50 mM $NaH_2PO_4$, 500 mM NaCl, pH 6.7) at 1 ml/min. Bio-Rad molecular weight standards (151-1901) were used to calibrate the column and calculate the approximate molecular size of the injected samples. As can be seen in FIG. 2, TTR(C10A/G83C) eluted at approximately 8.8 min corresponding to a molecular size of 49 kDa, which is comparable to the calculated molecular weight of the tetramer at 55 kDa. PTH-TTR(C10A/K15A/G83C) eluted at about 8.6 min corresponding to a molecular size of 67 kDa, which is close to the calculated 71 kDa for the tetramer. TTR(C10A/G83C)-Bradykinin eluted at about 8.7 min corresponding to a molecular size of 57 kDa, which is also close to the calculated 60 kDa for the tetramer.

EXAMPLE 9

Figure 3:
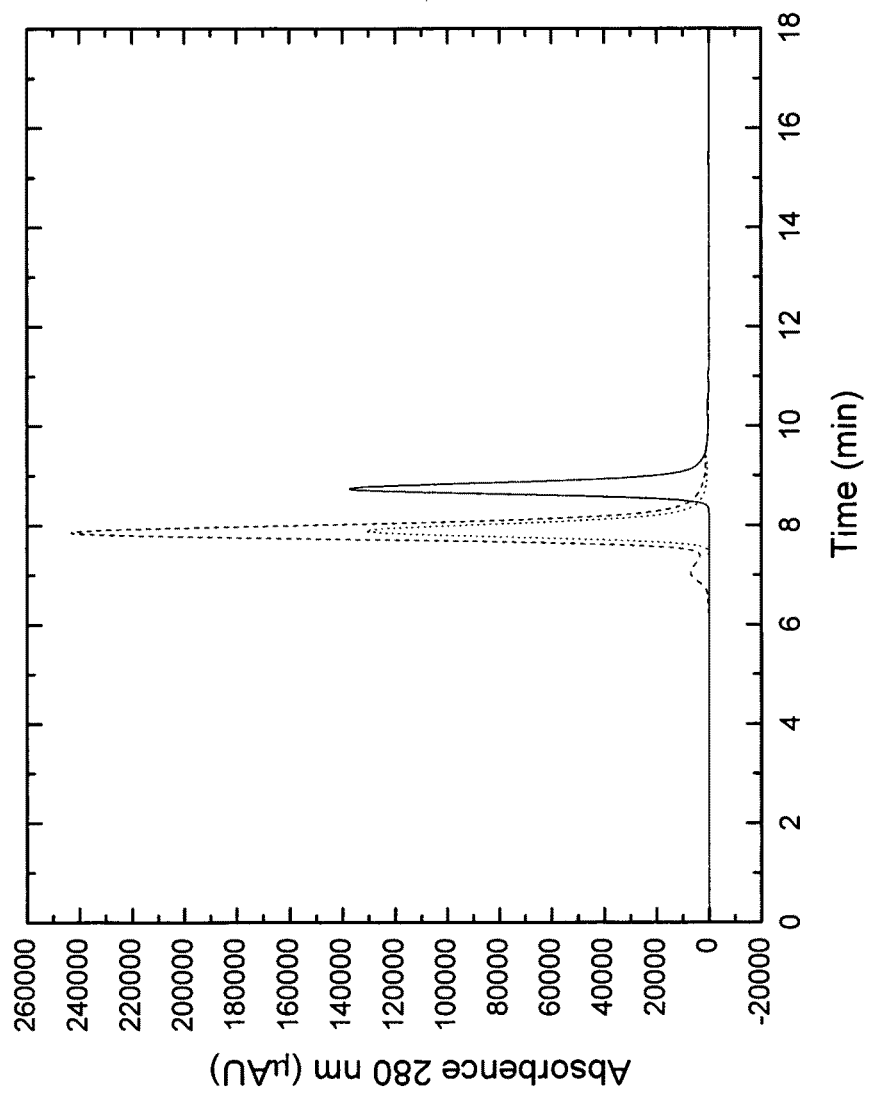
FIG. 3 demonstrates by size exclusion chromatography that fusion of proteins to the amino-terminus or carboxy-terminus of a TTR variant, TTR(C10A), does not alter its oligomeric structure. Solid line is TTR(C10A), dashed line is IL-1-ra fused to the carboxy-terminus of TTR(C10A), and the dotted line is IL-1-ra fused to the amino-terminus of TTR (C10A).

This example demonstrates that fusing a protein containing disulfide bonds to either the C-terminus or N-terminus of TTR(C10A) does not have a significant impact on its oligomeric structure. About 50 μg each of TTR(C10A), IL-1-ra-TTR(C10A), and TTR(C10A)-IL-1-ra was injected on to a Biosep-Sec-S 3000 column (7.8 mm ID×300 mm) (Phenomenex) in SEC-Buffer at 1 ml/min. Bio-Rad molecular weight standards (151-1901) were used to calibrate the column and calculate the approximate molecular weight of the injected samples. As can be seen in FIG. 3, TTR(C10A) elutes at approximately 8.8 min, which corresponds to a molecular size of 49 kDa which is comparable to the calculated molecular weight of the tetramer at 55 kDa. The IL-1-ra-TTR(C10A) fusion eluted at about 7.9 min corresponding to a molecular size of 188 kDa, which is noticeably larger than that expected for the tetramer at 124 kDa. Similarly, TTR(C10A)-IL-1-ra eluted at about 7.9 min, again corresponding to a molecular size of 188 kDa compared to the 124 kDa expected for the tetramer. These size discrepancies are likely due to differences in the shape of the molecule, since size exclusion chromatography is shape dependant and the standards are calibrated for globular proteins.

EXAMPLE 10

This example compares the binding of a TMP sequence fused to the carboxy-terminus of human immunoglobulin Fc (Fc-TMP) and TMP(m)-TTR to soluble human myeloproliferative leukemia (MPL) receptor. In addition, this example shows the effect of pegylation of the native TTR cysteine on the binding of the TMP fusion to the MPL receptor. The preparation of the pegylated TTR fusions is described in detail in Example 13.

Figure 4:
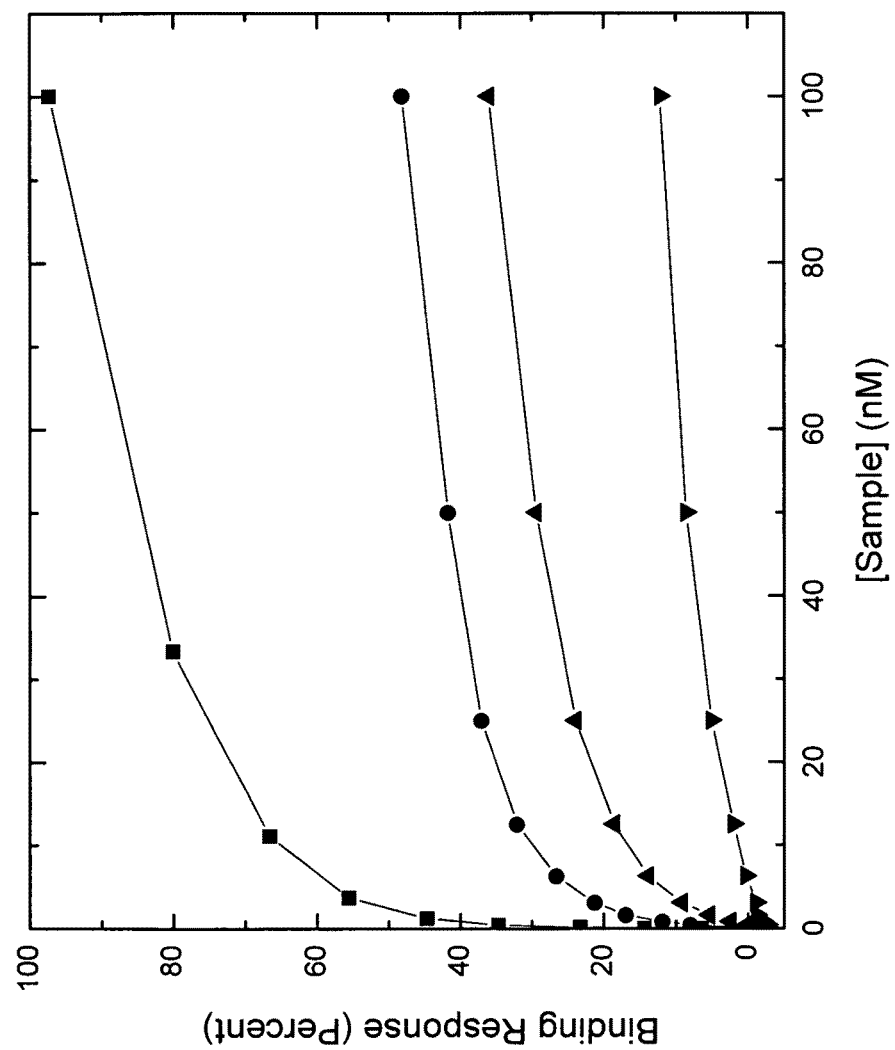
FIG. 4 shows the binding observed using BIAcore of various TPO-mimetic peptide (TMP) constructs to human MPL receptor: ■ Fc-TMP, ● TMP(m)-TTR, ▲ TMP(m)-TTR-PEG5K, ▼ TMP(m)-TTR-PEG20K.

For this example, human MPL receptor was covalently bound to a BIAcore CM5 chip at $R_L$=1300 $R_U$ using the EDC/NHS chemistry as per the manufacturer's instructions (BIAcore, Uppsula, Sweden). All samples were passed over the chip at 50 μl/min in Dulbecco's PBS (Gibco BRL, Gaithersburg, Md.) with 0.1 mg/ml bovine serum albumin and 0.005% P20 (polyoxyethylenesorbitan). The equilibrium endpoint was taken 3 min post injection. As can be seen in FIG. 4, Fc-TMP shows superior binding characteristics compared to TMP(m)-TTR. Further, this figure demonstrates that pegylation of the native TTR cysteine (Cys 10) interferes with the binding of TMP to the MPL receptor. The binding of TMP(m)-TTR-PEG5K showed a significantly repressed binding response compared to its non-pegylated counterpart, and TMP(m)-TTR-PEG20K showed an even more severe inhibition. This indicates that the presence of PEG on cysteine 10 likely causes steric interference for binding of the fused TMP to the MPL receptor, and larger PEGs produce more interference.

EXAMPLE 11

This example shows the effect of injecting TMP(m)-TTR into mice on blood platelet count. For this example 50 BDF1 mice (Charles River Laboratories, Wilmington, Mass.) were split into 5 groups and injected (day 0) subcutaneously with either diluting agent (Dulbecco's PBS with 0.1% bovine serum albumin) or diluting agent with 50 μg test protein per kg animal. Each group was divided in half and bled (140 μl) on alternate time points (day 0, 3, 5, 7, 11, 12, 14, and 17). Mice were anesthetized with isoflurane prior to collection.

Figure 5:
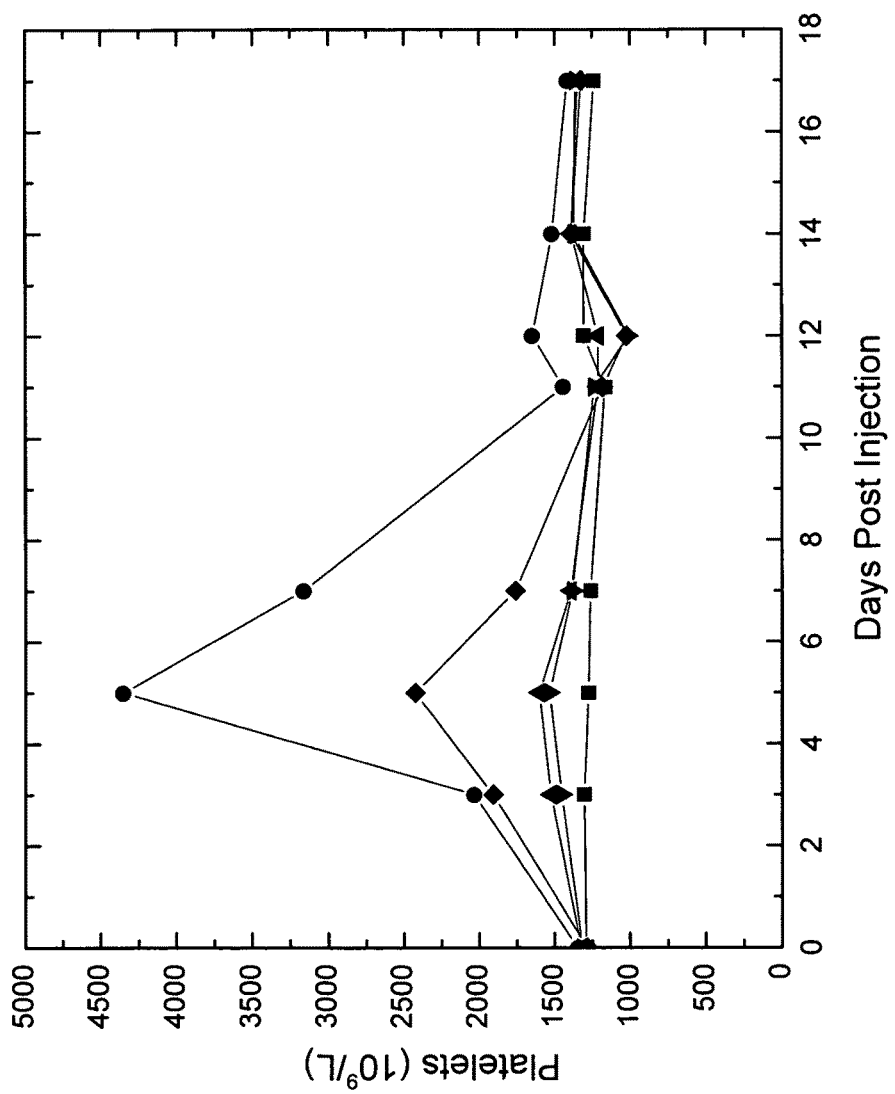
FIG. 5 shows that injection of TMP(m)-TTR-PEG5K induces platelet formation in mice. The following symbols correspond to the corresponding constructs: ■ Carrier, ● Fc-TMP, ▲ TTR-TMP, ▼ TMP(m)-TTR, and ♦ TMP(m)-TTR-PEG5K.

The collected blood was analyzed for a complete and differential count using an ADVIA 120 automated blood analyzer with murine software (Bayer Diagnostics, New York, N.Y.). As seen in FIG. 5, Fc-TMP showed the greatest response with platelet count peaking at $4.3 \times 10^{12}$ platelets $L^{-1}$ on day 5, which is over 3.4 times baseline at $1.2 \times 10^{12}$ platelets $L^{-1}$. TMP(m)-TTR-PEG 5K was a moderate responder peaking at $2.3 \times 10^{12}$ platelets $L^{-1}$ which is just under twice the baseline level. The non-pegylated form of TMP(m)-TTR shows very little response at $1.5 \times 10^{12}$ platelets $L^{-1}$ which is only 20% over the baseline level. The non-pegylated form of TMP(m)-TTR shows better binding in vitro than its pegylated counterparts (FIG. 4), but it has poor performance in vivo compared to TMP(m)-TTR-PEG 5K. This indicates that PEG is required to improve the biological half-life of the TTR construct, and this more than compensates for the reduced affinity for the receptor.

EXAMPLE 12

Figure 6:
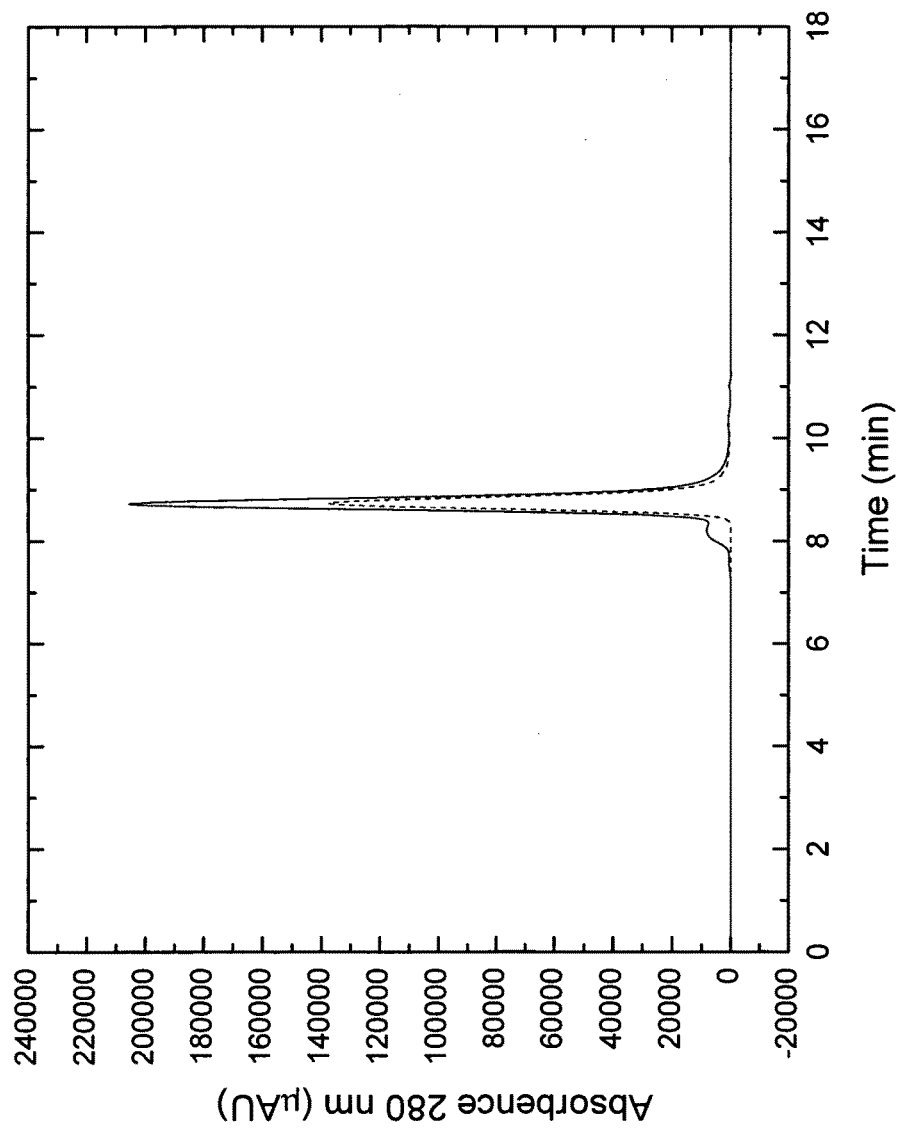
FIG. 6 demonstrates by size exclusion chromatography that native TTR and TTR(C10A) maintain a similar oligomeric configuration (an apparent tetramer). Solid line is native TTR and the dashed line is TTR(C10A).

This example demonstrates that mutation of cysteine 10 on TTR to alanine TTR(C10A) does not have a significant impact on its oligomeric structure. About 50 µg each of TTR and TTR(C10A) was injected on to a Biosep-Sec-S 3000 column (7.8 mm ID×300 mm) (Phenomenex) in SEC-Buffer at 1 ml/min. Bio-Rad molecular weight standards (151-1901) were used to calibrate the column and calculate the approximate molecular size of the injected samples. As can be seen in FIG. 6, TTR(C10A) elutes at approximately 8.8 min, which corresponds to a molecular size of 57 kDa which is similar to the calculated molecular weight of the tetramer at 55 kDa. This data combined with the observation that both forms of TTR are resistant to precipitation at 65° C. (data not shown) indicates that mutation of cysteine 10 to alanine does not have a significant impact on the structure or stability of TTR.

EXAMPLE 13

This example demonstrates that mutation of alanine 37 to cysteine TMP-TTR(C10A/A37C), aspartate 38 to cysteine TMP-TTR(C10A/D38C), alanine 81 to cysteine TMP-TTR (C10A/A81C), or glycine 83 to cysteine TMP-TTR(C10A/G83C) in a cysteine 10 to alanine background does not have a significant impact on the oligomeric structure of TTR. In addition, this example demonstrates that pegylation of these mutant forms of TTR with a 5K or 20K PEG produces two distinct species of TTR with significantly greater molecular size than the unpegylated form. The pegylation of TTR was carried out by first reducing about 8 ml of the TTR (7.28 mg/ml) with 10 mM DTT for 30 minutes at 30° C. in the presence of 50 mM tris HCl, pH 8.5. The reduced TTR was then desalted using a 26 ml SEPHADEX™ G25 medium column (2.6 cm ID) (Amersham Pharmacia Biotech) at 2.5 ml/min in 20 mM tris HCl, pH 8.5. The concentration was then determined by measuring the absorbance of the reduced TTR at 280 nm and using the calculated extinction coefficient (29,450 $M^{-1}$ for TMP-TTR(C10A/A37C) (5.14 mg/ml). One-half (4.6 ml) of the reduced sample was then immediately mixed with 810 µl of 5 mM methoxy-PEG-maleimide 5K (Shearwater Corporation, Huntsville, Ala.) and the remaining half was mixed with 1620 µl 2.5 mM methoxy-PEG-maleimide 20K (Shearwater Corporation). The reaction was allowed to proceed at 30° C. for 30 min and was quenched by the addition of 46 µl 1 M DTT. Each pegylated sample was then loaded on to a 5 ml HiTrap Q-sepharose column at 2.5 ml/min and washed with several column volumes of Q-Buffer A (20 mM tris HCl, pH 8.0) at 5 ml/min. The columns were eluted with a linear gradient to 40% Q-Buffer B (20 mM tris HCl, 1 M NaCl, pH 8.0) followed by a 2 column volume step to 100% Q-Buffer B. Peak fractions were pooled and the concentration determined by measuring the absorbance of the pool at 280 nm.

Figure 7:
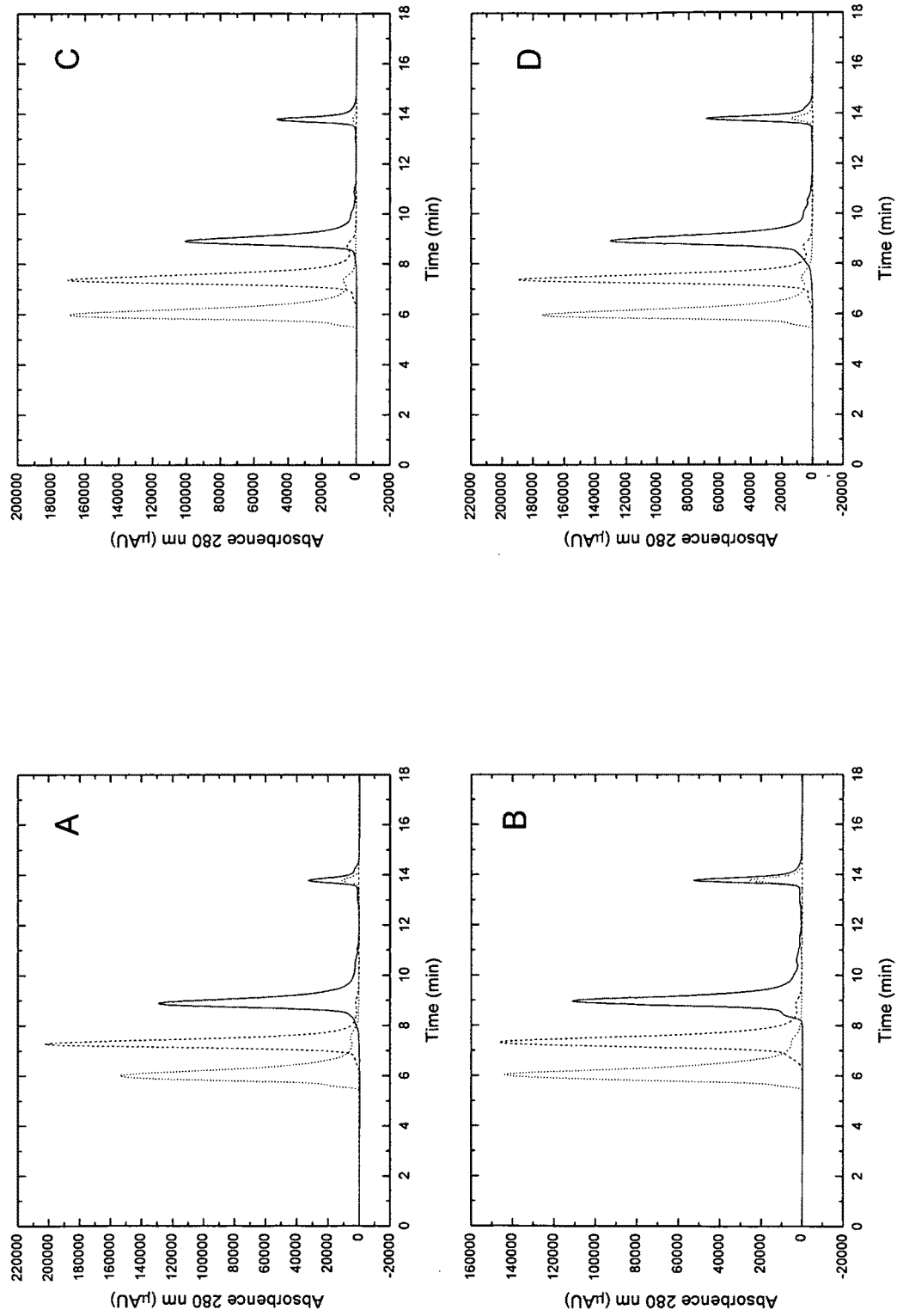
FIG. 7 demonstrates by size exclusion chromatography that conjugation of PEG to TTR increases its molecular size in a predictable uniform manner. Solid lines indicate no PEG conjugated, dashed lines indicate 5K PEG fused, and dotted lines indicate 20K PEG fused. The following constructs were used: A) TMP-TTR(C10A/A37C), B) TMP-TTR(C10A/D38C), C) TMP-TTR(C10A/A81C), and D) TMP-TTR (C10A/G83C).

About 50 µg of each sample was injected on to a Biosep-Sec-S 3000 column (7.8 mm ID×300 mm) (Phenomenex) in SEC-Buffer at 1 ml/min. Bio-Rad molecular weight standards (151-1901) were used to calibrate the column and calculate the approximate molecular size of the injected samples. As can be seen in FIG. 7, the apparent molecular size of the 4 non-pegylated TMP-TTR constructs is between 40 and 45 kDa which is noticeably lower than the expected 70 kDa tetramer. This retarded elution time is likely due to a slight interaction of the TMP-TTR construct with the size exclusion resin, which has been observed with several other TMP constructs (data not shown). After conjugation with the 5K PEG, the apparent molecular size increases to between 421 and 428 kDa (1.53-1.64 minutes more advanced elution than the unpegylated counterparts), which is much greater than the expected 90 kDa. The observation of an exaggerated molecular weight of pegylated molecules on size exclusion chromatography is frequently observed phenomenon (data not shown). The 20K PEG constructs elute earlier than the largest calibration standard (670 kDa) showing a 1.28-1.40 minutes more advanced elution than their 5K pegylated counterparts. This data taken together demonstrates that all 4 engineered mutant forms of TMP-TTR can be pegylated drastically increasing their apparent molecular size.

Figure 8:
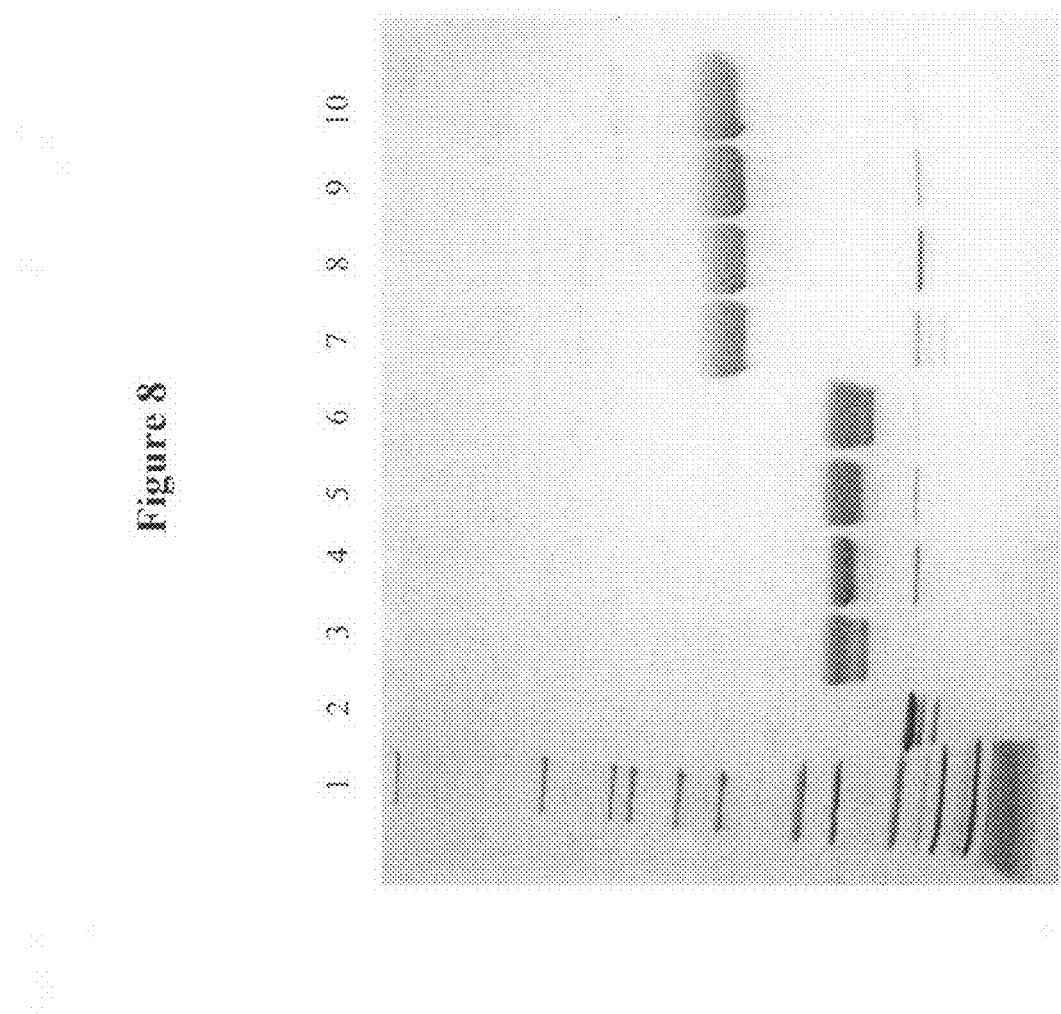
FIG. 8 is an SDS gel that depicts the extent of pegylation of various TMP-TTR constructs involving TTR variants having a non-native cysteine engineered in at one of four different locations. Lane 1 contains NOVEX® 12 molecular weight standards; lane 2 is unpegylated TMP-TTR(C10A/A37C); lanes 3-6 are 5K pegylated versions of TMP-TTR(C10A/A37C), TMP-TTR(C10A/D38C), TMP-TTR(C10A/A81C), and TMP-TTR(C10A/G83C) respectively; lanes 7-10 are 20K pegylated versions of TMP-TTR(C10A/A37C), TMP-TTR(C10A/D38C), TMP-TTR(C10A/A81C), and TMP-TTR(C10A/G83C), respectively.

About 2 µg of the pegylated TMP-TTR constructs were analyzed by SDS-PAGE (FIG. 8). This figure demonstrates by gel shift that most of the TMP-TTR monomers were modified by only one methoxy-PEG-maleimide, and the reaction was nearly complete leaving very little unmodified monomer.

EXAMPLE 14

Figure 9:
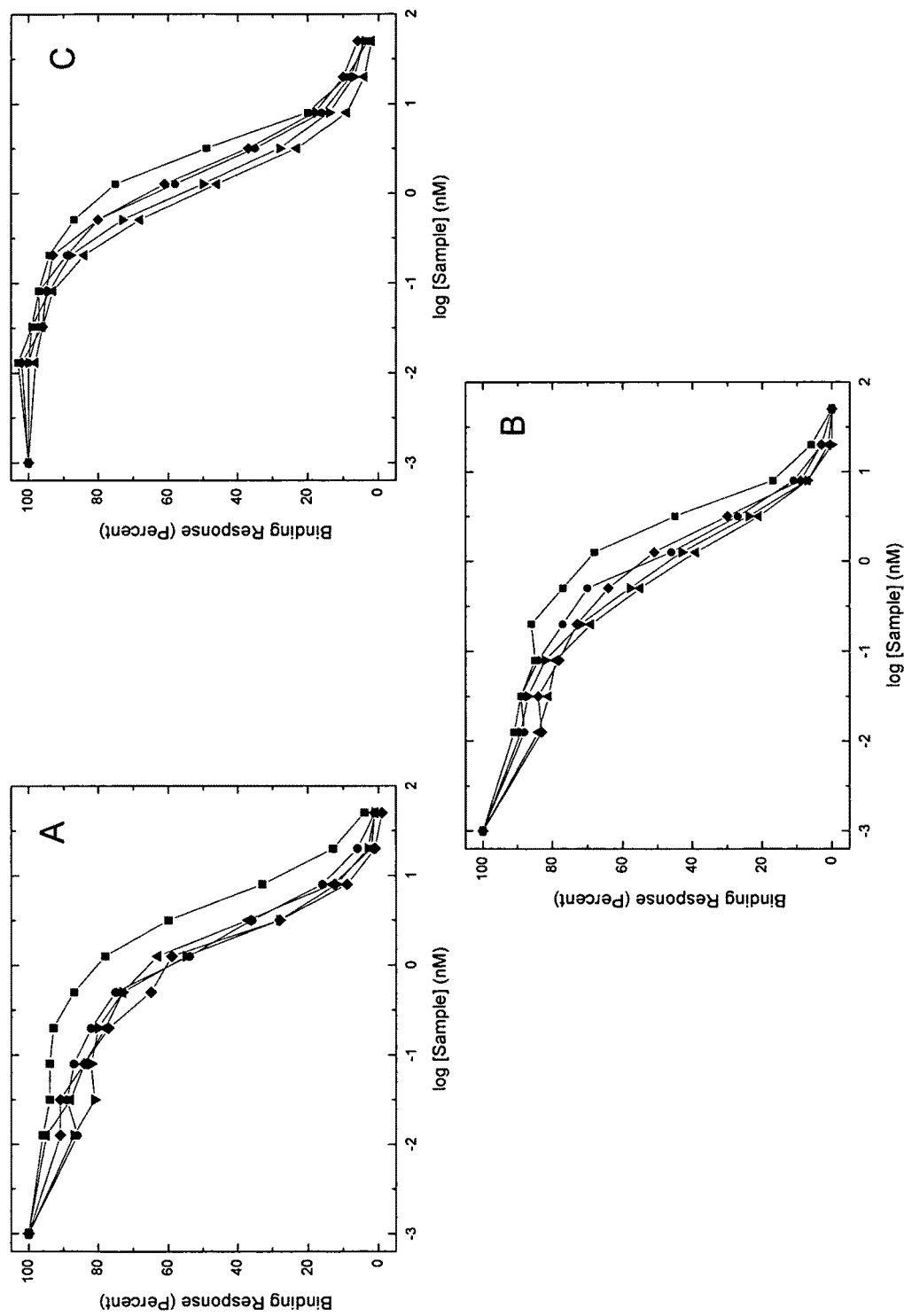
FIGS. 9A-C compare the competitive binding of Fc-TMP and TMP-TTR to human MPL by BIAcore analysis. A) ■ Fc-TMP, ● TMP-TTR(C10A/A37C), ▲ TMP-TTR(C10A/D38C), ▼ TMP-TTR(C10A/A81C), ♦ TMP-TTR(C10A/G83C). B) ■ Fc-TMP, 5K pegylated versions of TMP-TTR (C10A/A37C) (●), TMP-TTR(C10A/D38C) (▲), TMP-TTR(C10A/A81C) (▼), TMP-TTR(C10A/G83C)(♦). C) ■ Fc-TMP, 20K pegylated versions of TMP-TTR(C10A/A37C) (●), TMP-TTR(C10A/D38C)(▲), TMP-TTR(C10A/A81C) (▼), TMP-TTR(C10A/G83C)(♦).

This example demonstrates that Fc-TMP, TMP-TTR (C10A/A37C), TMP-TTR(C10A/D38C), TMP-TTR(C10A/A81C), and TMP-TTR(C10A/G83C) have similar affinities for binding human MPL receptor in vitro. For this example, Fc-TMP was bound to a BIAcore protein G chip at high density as per the manufacturer's instructions (BIAcore, Uppsula, Sweden). Test proteins were preincubated with 5 nM MPL receptor in Binding Buffer (Dulbecco's PBS (Gibco BRL, Gaithersburg, Md.) with 0.1 mg/ml bovine serum albumin and 0.005% P20 (polyoxyethylenesorbitan) for >2 hours at room temperature (about 23° C.). For non-pegylated proteins, 0.1 mg/ml heparin was added to prevent non-specific binding. All samples were then passed over the chip at 50 µl/min in Binding Buffer. The equilibrium endpoint was taken 3 min post injection. As can be seen in FIG. 9, all TTR constructs showed similar affinity for the MPL receptor with affinities ranging from 0.881 to 2.333 nm, while the Fc-TMP construct had affinities ranging from 3.276 to 5.369 nm.

EXAMPLE 15

This example shows the effect of injecting pegylated TMP-TTR constructs into mice on blood platelet count. For this example 170 BDF1 mice were split into 17 groups and injected (day 0) subcutaneously with 50 µg test protein per kg animal (TMP fusion construct, Fc-TMP, or a TTR(C10A) control). Each group was divided in half and bled (140 µl) on alternate time points (day 0, 3, 5, 7, 10, 12, and 14). Mice were anesthetized with isoflurane prior to collection.

Figure 10:
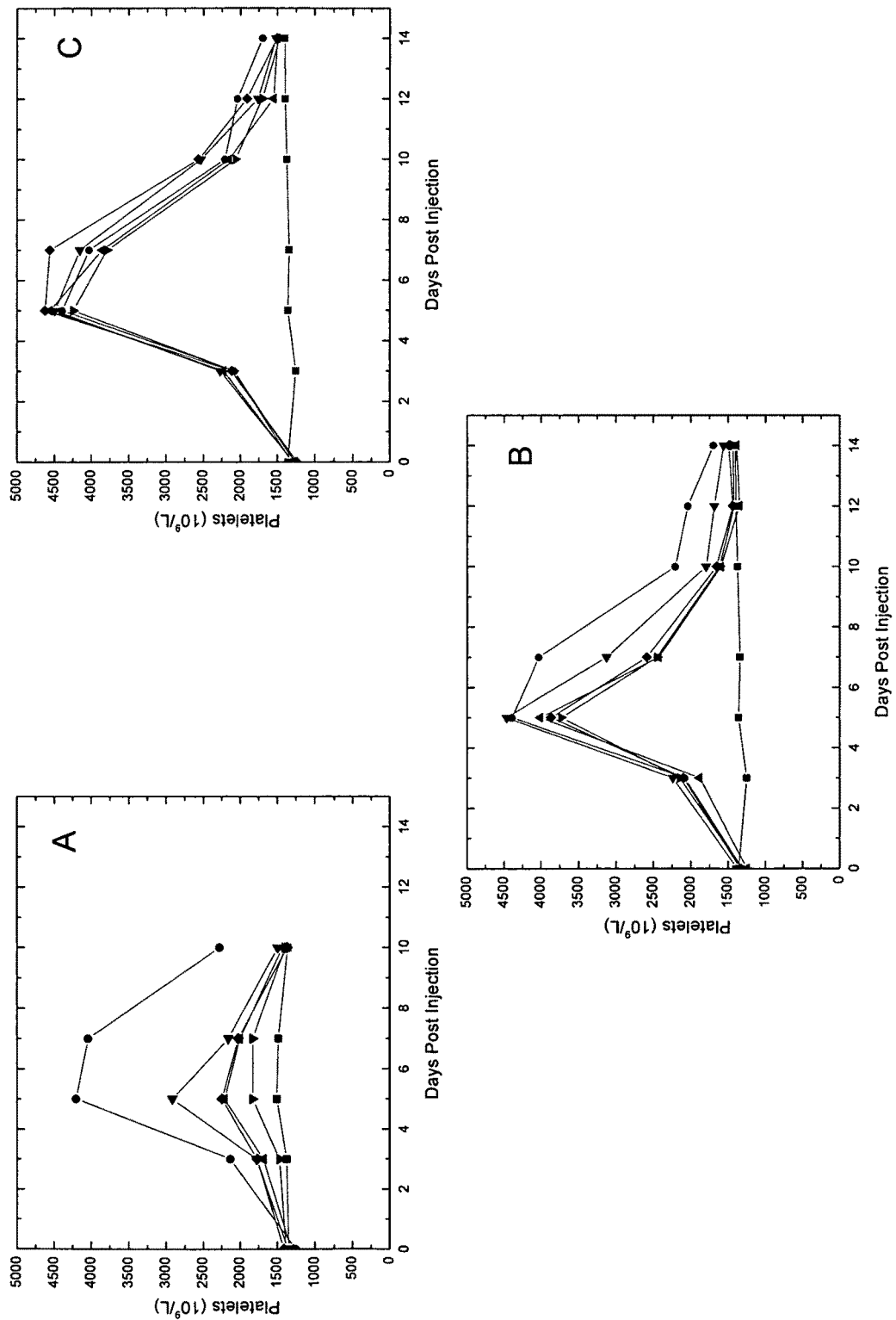
FIGS. 10A-C show that injection of TMP-TTR with PEG conjugated to engineered cysteines induces platelet formation in mice. A) ■ TTR(C10A), ● Fc-TMP, ▲ TMP-TTR (C10A/A37C), ▼ TMP-TTR(C10A/D38C) (carboxamidomethylated), ♦ TMP-TTR(C10A/A81C), ◄ TMP-TTR (C10A/G83C). B) ■ TTR(C10A), ● Fc-TMP, 5K pegylated versions of TMP-TTR(C10A/A37C)(▲), TMP-TTR(C10A/D38C) (▼), TMP-TTR(C10A/A81C)(♦), TMP-TTR(C10A/G83C)(◄). C) ■ TTR(C10A), ● Fc-TMP, 20K pegylated versions of TMP-TTR(C10A/A37C) (▲), TMP-TTR(C10A/D38C) (▼), TMP-TTR(C10A/A81C)(♦), TMP-TTR(C10A/G83C)(◄).

The collected blood was analyzed for a complete and differential count using an ADVIA 120 automated blood analyzer with murine software (Bayer Diagnostics, New York, N.Y.). As seen in FIG. 10A, Fc-TMP showed the greatest response with platelet count rising to over $4.2 \times 10^{12}$ platelets $L^{-1}$ on day 5 which is 3 times baseline at $1.4 \times 10^{12}$ platelets $L^{-1}$. All 4 of the non-pegylated TMP-TTR constructs preformed better than the control, but not as well as Fc-TMP with platelet counts between 1.8 and $2.9 \times 10^{12}$ platelets $L^{-1}$ on day 5, which is between a 29% and 107% improvement over baseline. As can be seen in FIG. 10B, addition of a 5K PEG group to the engineered cysteine of all 4 TMP-TTR constructs substantially improves efficacy with platelet counts between 3.7 and $4.4 \times 10^{12}$ platelets $L^{-1}$ (2.8 to 3.4 times baseline).

Also as can be seen in FIG. 10C, conjugation of a 20K PEG to TMP-TTR results in an additional, but less dramatic improvement in efficacy with platelet counts between 4.2 and $4.6 \times 10^{12}$ platelets $L^{-1}$ (3.2 to 3.5 times baseline). Since all of the TMP fusion constructs had similar binding affinities for MPL in vitro, this difference is likely due to the effect of PEG conjugation increasing the effective biological half-life of the construct.

EXAMPLE 16

This example shows the effect of injecting pegylated PTH-TTR constructs into mice on blood ionized calcium release. For this example 60 male, BDF1, 4 week-old mice were split into 12 groups and injected (day 0) subcutaneously with 8.91 mg test protein per kg animal (PTH fusion construct, PTH-Fc, or a TTR(C10A) control). Each group was bled (75 µl) at time points 0, 24, 48, and 72 hours. Mice were anesthetized with isoflurane prior to collection.

Figure 11:
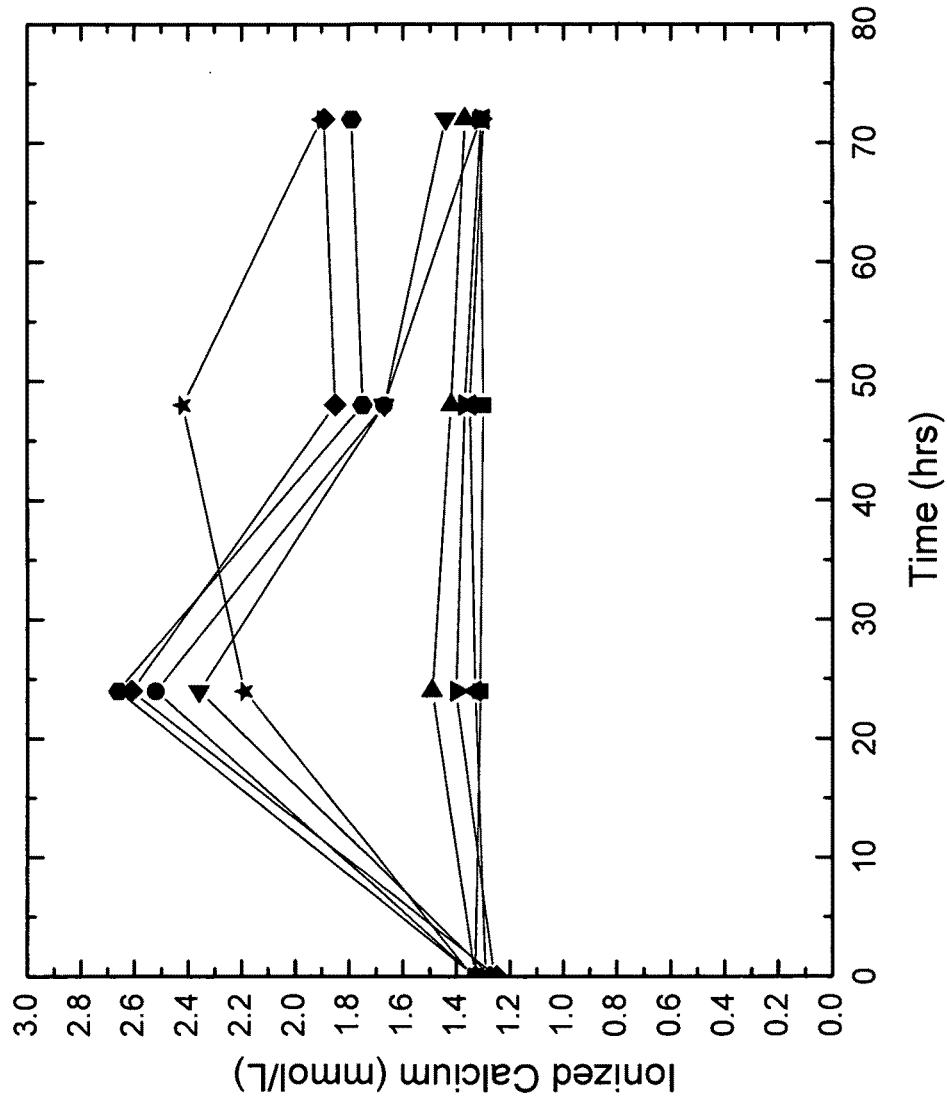
FIG. 11 shows that injection of PTH-TTR with PEG conjugated to engineered cysteines induces ionized calcium release in mice. The following symbols correspond to the corresponding constructs: ■ TTR(C10A), ● PTH-Fc, ▲ PTH-TTR, ▼ PTH-TTR(C10A/K15A/A37C) (carboxamidomethylated), ♦ 5K pegylated version of PTH-TTR(C10A/K15A/A37C), ◄ 20K pegylated version of PTH-TTR (C10A/K15A/A37C), ► PTH-TTR(C10A/K15A/G83C) (carboxamidomethylated), ● 5K pegylated version of PTH-TTR(C10A/K15A/G83C), and ★ 20K pegylated version of PTH-TTR(C10A/K15A/G83C).

The collected blood was analyzed for ionized calcium using a Ciba*Corning 634 Ca++/pH analyzer. As seen in FIG. 11, PTH-Fc, PTH-TTR(C10A/K15A/A37C) (PEG 5K), PTH-TTR(C10A/K15A/A37C) (PEG 20K), PTH-TTR (C10A/K15A/G83C) (PEG 5K), and PTH-TTR(C10A/K15A/G83C) (PEG 20K) showed the greatest response with ionized calcium levels rising between 2.2 and 2.7 mmol per L at 24 hours post-injection, which is 1.7 times baseline at 1.3 mmol per L. At 72 hours post injection, the ionized calcium levels of all groups returned to baseline, except PTH-TTR (C10A/K15A/A37C) (PEG 5K), PTH-TTR(C10A/K15A/G83C) (PEG 5K), and PTH-TTR(C10A/K15A/G83C) (PEG 20K) treated groups that maintained elevated ionized calcium levels between 1.8 and 1.9 mmol per L. The non-pegylated PTH-TTR constructs were equivalent to or slightly better than the TTR(C10A) control at raising serum ionized calcium levels.

EXAMPLE 17

This example describes the construction of a PTH-TTR (C10A/K15A/A81C) containing plasmid. The Xba1/Xba1 fragment of 5920 was ligated with the purified vector derived from digesting plasmid 5643 (described in example 1) with Xba1. The *E. coli* strain containing the resulting plasmid is described as 5933 PTH-TTRC10A/K15A/A81C.

```
SEQ ID NO: 43:
ATGTCTGTTTCTGAAATCCAGCTGATGCATAACCTGGGTAAACATCTGAA

CTCTATGGAACGTGTTGAATGGCTGCGTAAGAAACTGCAGGACGTTCATA

ACTTTGGTCCAACTGGTACCGGTGAATCCAAGGCTCCTCTGATGGTCGCA

GTTCTAGATGCTGTCCGAGGCAGTCCTGCCATCAATGTGGCCGTGCATGT

GTTCAGAAAGGCTGCTGATGACACCTGGGAGCCATTTGCCTCTGGGAAAA

CCAGTGAGTCTGGAGAGCTGCATGGGCTCACAACTGAGGAGGAATTTGTA

GAAGGGATATACAAAGTGGAAATAGACACCAAATCTTACTGGAAGTGTCT

TGGCATCTCCCCATTCCATGAGCATGCAGAGGTGGTATTCACAGCCAACG

ACTCCGGCCCCCGCCGCTACACCATTGCCGCCCTGCTGAGCCCCTACTCC

TATTCCACCACGGCTGTCGTCACCAATCCCAAGGAATAA
```

EXAMPLE 18

This example describes the preparation of a GLP-1-TTR (C10A/G83C) fusion and a GLP-1-TTR(C10A/K15A/G83C) fusion. These constructs were cloned using plasmid pAMG21, which is described in example 1. Each of the oligonucleotides utilized in this example are listed in Table 6.

The bacterial host GM121 is an *E. coli* K-12 strain that has been modified to contain the lacI$^Q$ repressor in the late ebg region (68 minutes). The presence of this repressor gene allows the use of this host with a variety of expression systems, however this repressor is irrelevant to the expression from luxPR. The untransformed host has no antibiotic resistances. Specifically, F'tet/393 was modified by the delivery of a lacI$^Q$ construct into the ebg operon between nucleotide position 2493 and 2937 as numbered in the Genbank accession number M64441Gb_Ba with the deletion of the intervening ebg sequence. The construct was delivered to the chromosome using a recombinant phage called AGebg-lacI$^Q$ #5.

After recombination and resolution only the chromosomal insert described above remains in the cell. It was renamed F'tet/GM120. F'tet/GM120 was then mutated in the hsdR gene to inactivate it. This was renamed F'tet/GM121. The F'tet episome was cured from the strain, verified as tetracyline sensitive and was stored as GM121 (ATCC #202174).

PCR was performed with Roche PCR Core Kit (Cat. No. 1 578 553) in 80 ul reactions containing 2-4 ul mini-prep plasmid DNA template, 1 uM each oligonucleotide, 0.2 mM each oligonucleotide, 5% DMSO (Sigma), and 2 U Taq DNA polymerase in order to amplify the GLP-1 sequence and a linker. Reaction cycles were 94° C. for 5 min followed by 35 cycles of [94° C. for 20 sec, 45° C. for 30 sec, 72° C. for 1 min]. PCR products were purified with QIAquick® PCR Purification Kit according to the manufacturer's protocol (QIAGEN). PCR products and vectors were then digested with NdeI and KpnI (New England Biolabs).

Digested DNA was purified from an agarose gel, then mixed and ligated by T4 DNA ligase (New England Biolabs) for 1.5-2 hours at room temperature. Each ligation mixture was transformed by electroporation into the host strain GM121 described above with a Biorad *E. coli* Pulser at 2.5KV in a cuvette with a gap length of 2 mm. The cells were allowed to recover in 2 ml Terrific Broth (TB) for about 3 hours at 37° C. at 250 rpm. 70-100 µl of the recovery culture was plated on LB agar containing 40 ug/ml kanamycin. DNA mini-preps were prepared and correct clones were verified by nucleotide sequencing.

To prepare the GLP-1-TTR(C10A/G83C) fusion, two oligonucleotides, oligonucleotide 1209-85, which binds the luxR promoter region, and 3131-63, which encodes the last 12 amino acids of the fusion linker and the first 8 amino acids of TTR, were synthesized. A pAMG21 plasmid derived from a strain which expresses a GLP-1 sequence with a N-terminal Met-Lys start followed by a seven Histidine sequence for nickel column purification, an Aspartic acid-Glutamic acid-Valine-Aspartic acid sequence for cleavage before the first Histidine of GLP-1 by caspase, the GLP-1 (A2G) sequence, and a 27 amino acid fusion linker was amplified using oligonucleotides 1209-85 and 3131-63. The PCR product was cloned and sequenced as described above. The resultant strain containing the new plasmid was designated GLP-1-TTR (C10A/G83C) (strain 6298) and had the DNA sequence identified in SEQ ID NO:47.

To prepare the GLP-1-TTR(C10A/K15A/G83C) fusion, two oligonucleotides, oligonucleotide 3183-83, which contains and NdeI site and encodes the purification and cleavage sequence described above plus the first six amino acids of GLP-1 (A2G), and 3183-84, which encodes the last 6 amino acids of the fusion linker and the first 8 amino acids of TTR, were synthesized.

A pAMG21 plasmid derived from a strain which expresses a GLP-1 sequence with a N-terminal Met-Lys start followed by a seven Histidine sequence for nickel column purification, an Aspartic acid-Glutamic acid-Valine-Aspartic acid sequence for cleavage before the first Histidine of GLP-1 by caspase, the GLP-1(A2G) sequence, and a 25 amino acid fusion linker was amplified using oligonucleotides 3183-83 and 3183-84. The PCR product was cloned and sequenced as described above. The resultant strain containing the new plasmid was designated GLP-1-TTR(C10A/K15A/G83C) (strain 6450) and had the DNA sequence identified in SEQ ID NO:48.

TABLE 6

| Oligo | Sequence | SEQ ID Number |
|---|---|---|
| 1209-85 | CGTACAGGTTTACGCAAGAAAATGG | 44 |
| 3131-63 | GGATTCACCGGTACCAGTTGGACCACCACCACCACC ACCACCCGCACTGCCTGAACCAGAGC | 45 |
| 3183-83 | TGACTAAGCCATATGAAACATCATCACCATCACCAT CATGACGAAGTTGATCACGGTGAAGGTACTTTCAC | 46 |
| 3183-84 | GGATTCACCGGTACCAGTTGGACCACCACCAC CACCGCTAC | 47 |

SEQ ID NO: 48
ATGAAACATCATCACCATCACCATCATGACGAAGTTGATCACGGTGAAGG
TACTTTCACTTCTGACGTTTCTTCTTATCTGGAAGGTCAGGCTGCTAAAG
AATTCATCGCTTGGCTGGTTAAAGGTCGTGGTGGTTCTGGTTCTGCTACT
GGTGGTTCCGGCTCCACCGCAAGCTCTGGTTCAGGCAGTGCGGGTGGTGG
TGGTGGTGGTGGTCCAACTGGTACCGGTGAATCCAAGGCTCCTCTGATGG
TCAAAGTTCTAGATGCTGTCCGAGGCAGTCCTGCCATCAATGTGGCCGTG
CATGTGTTCAGAAAGGCTGCTGATGACACCTGGGAGCCATTTGCCTCTGG
GAAAACCAGTGAGTCTGGAGAGCTGCATGGGCTCACAACTGAGGAGGAAT
TTGTAGAAGGGATATACAAAGTGGAAATAGACACCAAATCTTACTGGAAG
GCACTTTGCATCTCCCCATTCCATGAGCATGCAGAGGTGGTATTCACAGC
CAACGACTCCGGCCCCCGCCGCTACACCATTGCCGCCCTGCTGAGCCCCT
ACTCCTATTCCACCACGGCTGTCGTCACCAATCCCAAGGAATAA

SEQ ID NO: 49
ATGAAACATCATCACCATCACCATCATGACGAAGTTGATCACGGTGAAGG
TACTTTCACTTCTGACGTTTCTTCTTATCTGGAAGGTCAGGCTGCTAAAG
AATTCATCGCTTGGCTGGTTAAAGGTCGTGGTGGTGGTGGTTCTGGT
GGTGGTGGTTCTGGTGGTGGTGGTTCTGGCGGCGGTGGTAGCGGTGGTGG
TGGTGGTGGTCCAACTGGTACCGGTGAATCCAAGGCTCCTCTGATGGTCA
CAGTTCTAGATGCTGTCCGAGGCAGTCCTGCCATCAATGTGGCCGTGCAT
GTGTTCAGAAAGGCTGCTGATGACACCTGGGAGCCATTTGCCTCTGGGAA
AACCAGTGAGTCTGGAGAGCTGCATGGGCTCACAACTGAGGAGGAATTTG
TAGAAGGGATATACAAAGTGGAAATAGACACCAAATCTTACTGGAAGGCA
CTTTGCATCTCCCCATTCCATGAGCATGCAGAGGTGGTATTCACAGCCAA
CGACTCCGGCCCCCGCCGCTACACCATTGCCGCCCTGCTGAGCCCCTACT
CCTATTCCACCACGGCTGTCGTCACCAATCCCAAGGAATAA

EXAMPLE 19

This example describes the preparation of a GLP-1 (A2G)-K-Fc fusion. This construct was cloned using plasmid pAMG33*, which differs from pAMG21 in that the lux protein and promoters are replaced with lacI binding sites and an IPTG inducible promoter and the ribosomal binding site sequence is shorter (the sequence between the AatII and ClaI recognition sites is replaced with AATTGTGAGCGGATAA-CAATTGAC AAATGCTAAAATTCTTGATTAATTGT-GAGCGGATAACAATTTATCGATTTGAT-
TCTAGAAGGAGGAATAA) and some of the sequence after the SacII recognition site was deleted (leaving ATAAATAAGTAACGATCCGGTCCAG-
TAATGACCTCAGAAC TCCATCTGGATTTGTTCA-GAACGCTCGGTTGCCGCCGGGCGTTTTT-
TATTGGTGAGAATCGCAGCAAC
TTGTCGCGCCAATCGAGCCAT-
GTCGTCGTCAACGACCCCCCATTCAA-
GAACAGCAAGCAGCATTGAGA ACTTTGGAATC-CAGTCCCTCTTCCACCTGCTGACCG). Each of the oligonucleotides utilized in this example are listed in Table 7.

To prepare the GLP-1 (A2G)-Fc fusion, two oligonucleotides, oligonucleotide 2985-92, which contains and NdeI site and encodes the purification and cleavage sequence described above plus the first eight amino acids of GLP-1 (A2G), and 2687-50, which encodes the amino acids 18 through 23 of the Fc, were synthesized. A pAMG33* plasmid derived from a strain which expresses a GLP-1 (A2G) sequence with a N-terminal Met start, a 27 amino acid linker, and an Fc sequence was amplified using oligonucleotides 2985-92 and 2687-50. The PCR product was cloned and sequenced as described above except the enzymes used were NdeI and EcoRI. A colony screening step was included which verified the presence of insert by PCR with oligonucleotides directed against upstream vector sequence and the 5 His-Aspartic acid sequence which the insert introduced. The resultant strain containing the new plasmid was designated GLP-1 (A2G)-K-Fc (strain 5945) and had the DNA sequence identified in SEQ ID NO:51.

TABLE 7

| Oligo | Sequence | SEQ ID Number |
|---|---|---|
| 2985-92 | AGACCTGTACATATGAAACATCATCACCATCACCAT CATGACGAAGTTGATCACGGTGAAGGTACTTTCAC TTCTG | 50 |
| 2687-50 | GGGGGAAGAGGAAAACTGAC | 51 |

SEQ ID NO: 52
ATGAAACATCATCACCATCACCATCATGACGAAGTTGATCACGGTGAAGG
TACTTTCACTTCTGACGTTTCTTCTTATCTGGAAGGTCAGGCTGCTAAAG
AATTCATCGCTTGGCTGGTTAAAGGTCGTGGTGGTTCTGGTTCTGCTACT
GGTGGTTCCGGCTCCACCGCAAGCTCTGGTTCAGGCAGTGCGACTCATGG
TGGTGGTGGTGGTGACAAAACTCACACATGTCCACCGTGCCCAGCACCTG
AACTCCTGGGGGGACCGTCAGTTTTCCTCTTCCCCCCAAAACCCAAGGAC
ACCCTCATGATCTCCCGGACCCCTGAGGTCACATGCGTGGTGGTGGACGT
GAGCCACGAAGACCCTGAGGTCAAGTTCAACTGGTACGTGGACGGCGTGG
AGGTGCATAATGCCAAGACAAAGCCGCGGGAGGAGCAGTACAACAGCACG
TACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCG
AGAAAACCATCTCCAAAGCCAAAGGGCAGCCCCGAGAACCACAGGTGTAC
ACCCTGCCCCCATCCCGGGATGAGCTGACCAAGAACCAGGTCAGCCTGAC
CTGCCTGGTCAAAGGCTTCTATCCCAGCGACATCGCCGTGGAGTGGGAGA
GCAATGGGCAGCCGGAGAACAACTACAAGACCACGCCTCCCGTGCTGGAC
TCCGACGGCTCCTTCTTCCTCTACAGCAAGCTCACCGTGGACAAGAGCAG
GTGGCAGCAGGGGAACGTCTTCTCATGCTCCGTGATGCATGAGGCTCTGC
ACAACCACTACACGCAGAAGAGCCTCTCCCTGTCTCCGGGTAAA

EXAMPLE 20

This example describes the cloning of the CH2 domain of an immunoglobulin molecule to the TTR(C10A) to generate TMP-CH2-TTRC10A and TTRC10A-CH2-TMP.

The CH2 domain derived from TMP-Fc was linked to the C-terminal end of TTR(C10A), i.e., strain 5619, by a two-step PCR procedure. The CH2 domain (containing from 5' to 3': the last 7 codons of TTR, CH2 and a BamH1-XhoI linker) was first amplified by the following oligos:

2973-77:
(SEQ ID NO: 53)
GTC GTC ACC AAT CCC AAG GAA GGT TCT GGC TCC GGA

TCA GGG GGA CCG TCA GTT TTC CTC,
and 2973-78:
(SEQ ID NO: 54)
CCG CGG ATC CTC GAG ATT AGG ATC CAG AAC CCC CTT

TGG CTT TGG AGA TGG T.

This fragment was then fused to 5619 in a subsequent PCR by oligos 2973-78 and 2973-79:
(SEQ ID NO: 55)
GAG GAA TAA CAT ATG GGT CCA ACT GGT ACC GGT GAA

TCC AAG, followed by Nde1/XhoI digest and cloning into similarly restricted pAMG21. The resulting plasmid is described as 6017 (TTRC10A-CH2):

SEQ ID NO: 56:
ATGGGTCCAACTGGTACCGGTGAATCCAAGGCTCCTCTGATGGTCAAAGT

TCTAGATGCTGTCCGAGGCAGTCCTGCCATCAATGTGGCCGTGCATGTGT

TCAGAAAGGCTGCTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGGCACTTG

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGCTCCGGAT

CAGGGGGACCGTCAGTTTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAGGGGGTTCTGGATCCTAA

The Xba1/Xba1 fragment of 6017 was replaced with the corresponding fragment of 5704 as described above to construct TMP-TTRC10A-CH2 (Strain 6024):

SEQ ID NO: 57:
ATGATCGAAGGTCCGACTCTGCGTCAGTGGCTGGCTGCTCGTGCTGGCGG

TGGTGGCGGAGGGGGTGGCATTGAGGGCCCAACCCTTCGCCAATGGCTTG

CAGCACGCGCAGGTCCAACTGGTACCGGTGAATCCAAGGCTCCTCTGATG

GTCAAAGTTCTAGATGCTGTCCGAGGCAGTCCTGCCATCAATGTGGCCGT

GCATGTGTTCAGAAAGGCTGCTGATGACACCTGGGAGCCATTTGCCTCTG

GGAAAACCAGTGAGTCTGGAGAGCTGCATGGGCTCACAACTGAGGAGGAA

TTTGTAGAAGGGATATACAAAGTGGAAATAGACACCAAATCTTACTGGAA

GGCACTTGGCATCTCCCCATTCCATGAGCATGCAGAGGTGGTATTCACAG

CCAACGACTCCGGCCCCCGCCGCTACACCATTGCCGCCCTGCTGAGCCCC

TACTCCTATTCCACCACGGCTGTCGTCACCAATCCCAAGGAAGGTTCTGG

CTCCGGATCAGGGGGACCGTCAGTTTTCCTCTTCCCCCCAAAACCCAAGG

ACACCCTCATGATCTCCCGGACCCCTGAGGTCACATGCGTGGTGGTGGAC

GTGAGCCACGAAGACCCTGAGGTCAAGTTCAACTGGTACGTGGACGGCGT

GGAGGTGCATAATGCCAAGACAAAGCCGCGGGAGGAGCAGTACAACAGCA

CGTACCGTGTGGTCAGCGTCCTCACCGTCCTGCACCAGGACTGGCTGAAT

GGCAAGGAGTACAAGTGCAAGGTCTCCAACAAAGCCCTCCCAGCCCCCAT

CGAGAAAACCATCTCCAAAGCCAAGGGGGTTCTGGATCCTAA

Construction of TTRC10A-CH2-TMP was done as follows: the TMP fragment containing a 5' BamHI linker and 3' XhoI linker was amplified by oligos 2694-19 and 2974-70:
(SEQ ID NO: 58)
GAG GAA TAA GGA TCC ATC GAA GGT CCG ACT CTG CG.

The amplified fragment was digested with BamH1 and Xho1 and was subsequently ligated with similarly restricted 6017. The resulting clone is described as strain 6104 (TTRC10A-CH2-TMP).

SEQ ID NO: 59:
ATGGGTCCAACTGGTACCGGTGAATCCAAGGCTCCTCTGATGGTCAAAGT

TCTAGATGCTGTCCGAGGCAGTCCTGCCATCAATGTGGCCGTGCATGTGT

TCAGAAAGGCTGCTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGGCACTTG

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGCTCCGGAT

CAGGGGGACCGTCAGTTTTCCTCTTCCCCCCAAAACCCAAGGACACCCTC

ATGATCTCCCGGACCCCTGAGGTCACATGCGTGGTGGTGGACGTGAGCCA

CGAAGACCCTGAGGTCAAGTTCAACTGGTACGTGGACGGCGTGGAGGTGC

ATAATGCCAAGACAAAGCCGCGGGAGGAGCAGTACAACAGCACGTACCGT

GTGGTCAGCGTCCTCACCGTCCTGCACCAGGACTGGCTGAATGGCAAGGA

GTACAAGTGCAAGGTCTCCAACAAAGCCCTCCCAGCCCCCATCGAGAAAA

CCATCTCCAAAGCCAAGGGGGTTCTGGATCCATCGAAGGTCCGACTCTG

CGTCAGTGGCTGGCTGCTCGTGCTGGCGGTGGTGGCGGAGGGGGTGGCAT

TGAGGGCCCAACCCTTCGCCAATGGCTTGCAGCACGCGCATAA

Another configuration of this fusion was made as TMP-CH2-TTR2. The CH2 domain derived from TMP-Fc was first linked to N-terminus of TTRC10A by a two-step PCR. The CH2 domain (containing from 5' to 3': a NdeI-BamHI linker, CH2 and the first 7 codons of TTR C10A) was first amplified by oligos 2974-65:
(SEQ ID NO: 60)
TTC ACC GGT ACC AGT TGG ACC AGA ACC CCC TTT GGC TTT GGA GAT GGT,
and 2974-66:
(SEQ ID NO: 61)
GAG GAA TAA CAT ATG GGA TCC GGT TCT GGG GGA CCG

TCA GTT TTC CTC.

This fragment was fused to 5619 in a subsequent PCR by oligos 2974-66 and 2693-80 (example 1), followed by restriction with NdeI/XhoI and cloning into similarly restricted pAMG21. The resulting clone is described as 6016 (CH2-TTRC10A):

SEQ ID NO: 62:
ATGGGATCCGGTTCTGGGGGACCGTCAGTTTTCCTCTTCCCCCCAAAACC

CAAGGACACCCTCATGATCTCCCGGACCCCTGAGGTCACATGCGTGGTGG

TGGACGTGAGCCACGAAGACCCTGAGGTCAAGTTCAACTGGTACGTGGAC

GGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGC

TGAATGGCAAGGAGTACAAGTGCAAGGTCTCCAACAAAGCCCTCCCAGCC

CCCATCGAGAAAACCATCTCCAAAGCCAAAGGGGGTTCTGGTCCAACTGG

TACCGGTGAATCCAAGGCTCCTCTGATGGTCAAAGTTCTAGATGCTGTCC

GAGGCAGTCCTGCCATCAATGTGGCCGTGCATGTGTTCAGAAAGGCTGCT

GATGACACCTGGGAGCCATTTGCCTCTGGGAAAACCAGTGAGTCTGGAGA

GCTGCATGGGCTCACAACTGAGGAGGAATTTGTAGAAGGGATATACAAAG

TGGAAATAGACACCAAATCTTACTGGAAGGCACTTGGCATCTCCCCATTC

CATGAGCATGCAGAGGTGGTATTCACAGCCAACGACTCCGGCCCCCGCCG

CTACACCATTGCCGCCCTGCTGAGCCCCTACTCCTATTCCACCACGGCTG

TCGTCACCAATCCCAAGGAATAA

The TMP fragment containing a NdeI linker at 5' end and a BamHI linker at 3' end was amplified by oligos 2974-68:
(SEQ ID NO: 63)
GAG GAA TAA CAT ATG ATC GAA GGT CCG ACT CTG,
and 2974-69:
(SEQ ID NO: 64)
TAA CAT ATG GGA TCC TGC GCG TGC TGC AAG CCA TTG.

This fragment was then digested with NdeI/BamHI and ligated with the vector which was similarly restricted, gel purified from strain 6016. The resulting clone is described as 6110 (TMP-CH2-TTRC10A):

SEQ ID NO: 65:
ATGATCGAAGGTCCGACTCTGCGTCAGTGGCTGGCTGCTCGTGCTGGCGG

TGGTGGCGGAGGGGGTGGCATTGAGGGCCCAACCCTTCGCCAATGGCTTG

CAGCACGCGCAGGATCCGGTTCTGGGGGACCGTCAGTTTTCCTCTTCCCC

CCAAAACCCAAGGACACCCTCATGATCTCCCGGACCCCTGAGGTCACATG

CGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAG

CAGTACAACAGCACGTACCGTGTGGTCAGCGTCCTCACCGTCCTGCACCA

GGACTGGCTGAATGGCAAGGAGTACAAGTGCAAGGTCTCCAACAAAGCCC

TCCCAGCCCCCATCGAGAAAACCATCTCCAAAGCCAAAGGGGGTTCTGGT

CCAACTGGTACCGGTGAATCCAAGGCTCCTCTGATGGTCAAAGTTCTAGA

TGCTGTCCGAGGCAGTCCTGCCATCAATGTGGCCGTGCATGTGTTCAGAA

AGGCTGCTGATGACACCTGGGAGCCATTTGCCTCTGGGAAAACCAGTGAG

TCTGGAGAGCTGCATGGGCTCACAACTGAGGAGGAATTTGTAGAAGGGAT

ATACAAAGTGGAAATAGACACCAAATCTTACTGGAAGGCACTTGGCATCT

CCCCATTCCATGAGCATGCAGAGGTGGTATTCACAGCCAACGACTCCGGC

CCCCGCCGCTACACCATTGCCGCCCTGCTGAGCCCCTACTCCTATTCCAC

CACGGCTGTCGTCACCAATCCCAAGGAATAA

EXAMPLE 21

This example describes the construction of TTRC10A/K15A-TMP, TTRC10A/K15A/A81C-TMP and TTRC10A/K15A/G83C-TMP.

TMP was also cloned at the C-termini of TTR and variants thereof. The full length TMP containing at its N-terminal end a 5-amino acids linker (gsgsg) plus the last 7 amino acids of wt TTR was amplified by the following set of oligonucleotides in a standard PCR procedure.

2694-18:
(SEQ ID NO: 66)
GTC GTC ACC AAT CCC AAG GAA GGT TCT GGT TCT GGT
ATC GAA,
and 2694-19:
(SEQ ID NO: 67)
CCG CGG ATC CTC GAG ATT ATG CGC GTG CTG CAA GCC
ATT G This PCR fragment was further linked to the 3' end of wt TTR by a second PCR utilizing oligos 2694-19 and 2693-79 as described in example 1. The resulting clone was sequence confirmed and is described as strain 5365 (TTR-TMP):

SEQ ID NO: 68:
ATGGGTCCAACTGGTACCGGTGAATCCAAGTGTCCTCTGATGGTCAAAGT

TCTAGATGCTGTCCGAGGCAGTCCTGCCATCAATGTGGCCGTGCATGTGT

TCAGAAAGGCTGCTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGGCACTTG

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGTTCTGGTA

TCGAAGGTCCGACTCTGCGTCAGTGGCTGGCTGCTCGTGCTGGCGGTGGT

GGCGGAGGGGGTGGCATTGAGGGCCCAACCCTTCGCCAATGGCTTGCAGC

ACGCGCATAA

The Xba1/Xba1 fragment of 5365 was then replaced by the corresponding Xba1/Xba1 fragment of strain 5895 to make strain 5921 (TTRC10A/K15A-TMP) as described above:

SEQ ID NO: 69:
ATGGGTCCAACTGGTACCGGTGAATCCAAGGCTCCTCTGATGGTCGCAGT

TCTAGATGCTGTCCGAGGCAGTCCTGCCATCAATGTGGCCGTGCATGTGT

TCAGAAAGGCTGCTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGGCACTTG

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGTTCTGGTA

TCGAAGGTCCGACTCTGCGTCAGTGGCTGGCTGCTCGTGCTGGCGGTGGT

GGCGGAGGGGGTGGCATTGAGGGCCCAACCCTTCGCCAATGGCTTGCAGC

ACGCGCATAA

Plasmid 5921 was subsequently modified by replacing the amino acids at the following positions: A37, A81 and G83, with the amino acid Cysteine as described in example 1, except that the TTR 3' oligo utilized with the mutation oligos (2693-80) in example 1 was replaced with 2694-19, resulting in Strain 5982, containing TTRC10A/K15A/A37C-TMP (SEQ ID NO:70), Strain 5983 containing TTRC10A/K15A/A81C-TMP (SEQ ID NO:71), and Strain 5984 containing TTRC10A/K15A/G83C-TMP (SEQ ID NO:72).

SEQ ID NO: 70:
ATGGGTCCAACTGGTACCGGTGAATCCAAGGCTCCTCTGATGGTCGCAGT

TCTAGATGCTGTCCGAGGCAGTCCTGCCATCAATGTGGCCGTGCATGTGT

TCAGAAAGGCTTGTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGGCACTTG

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGTTCTGGTA

TCGAAGGTCCGACTCTGCGTCAGTGGCTGGCTGCTCGTGCTGGCGGTGGT

GGCGGAGGGGGTGGCATTGAGGGCCCAACCCTTCGCCAATGGCTTGCAGC

ACGCGCATAA

SEQ ID NO: 71:
ATGGGTCCAACTGGTACCGGTGAATCCAAGGCTCCTCTGATGGTCGCAGT

TCTAGATGCTGTCCGAGGCAGTCCTGCCATCAATGTGGCCGTGCATGTGT

TCAGAAAGGCTGCTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGTGTCTTG

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGTTCTGGTA

TCGAAGGTCCGACTCTGCGTCAGTGGCTGGCTGCTCGTGCTGGCGGTGGT

GGCGGAGGGGGTGGCATTGAGGGCCCAACCCTTCGCCAATGGCTTGCAGC

ACGCGCATAA

SEQ ID NO: 72:
ATGGGTCCAACTGGTACCGGTGAATCCAAGGCTCCTCTGATGGTCGCAGT

TCTAGATGCTGTCCGAGGCAGTCCTGCCATCAATGTGGCCGTGCATGTGT

TCAGAAAGGCTGCTGATGACACCTGGGAGCCATTTGCCTCTGGGAAAACC

AGTGAGTCTGGAGAGCTGCATGGGCTCACAACTGAGGAGGAATTTGTAGA

AGGGATATACAAAGTGGAAATAGACACCAAATCTTACTGGAAGGCACTTT

GCATCTCCCCATTCCATGAGCATGCAGAGGTGGTATTCACAGCCAACGAC

TCCGGCCCCCGCCGCTACACCATTGCCGCCCTGCTGAGCCCCTACTCCTA

TTCCACCACGGCTGTCGTCACCAATCCCAAGGAAGGTTCTGGTTCTGGTA

TCGAAGGTCCGACTCTGCGTCAGTGGCTGGCTGCTCGTGCTGGCGGTGGT

GGCGGAGGGGGTGGCATTGAGGGCCCAACCCTTCGCCAGTGGCTTGCAGC

ACGCGCATAA

EXAMPLE 22

This example describes the construction of TMP-TTRC10A/K15A/A81C and TMP-TTRC10A/K15A/A37C. The Lys at 15th position of TTR was mutagenized to Ala in strains 5704, 5706 and 5707 by the following methods. Plasmid 5513 was digested with Nde1/Kpn1, the insert harboring TMP fragment and the first 6 amino acids of TTR was purified and ligated with Nde1/Kpn1 restricted and gel purified vector derived from strain 5895. The bacterial strain containing the resulting plasmid is described as 5919 (TMP-TTRC10A/K15A/G83C). Plasmid 5919 was then digested with Xba1, the resulting Xba1/Xba1 fragment containing TMP and the first 18 codons of TTR including the C10A and K15A mutations was gel purified and ligated with Xba1 digested, phosphatase treated and gel purified vectors derived from strain 5704 and 5706. The new strains are described as 5918 (TMP-TTRC10A/K15A/A81C) and 6023 (TMP-TTRC10A/K15A/A37C).

TMP-TTRC10A/K15A/G83C (SEQ ID NO: 73):
ATGATCGAAGGTCCGACTCTGCGTCAGTGGCTGGCTGCTCGTGCTGGCGG

TGGTGGCGGAGGGGGTGGCATTGAGGGCCCAACCCTTCGCCAATGGCTTG

CAGCACGCGCAGGTCCAACTGGTACCGGTGAATCCAAGGCTCCTCTGATG

GTCGCAGTTCTAGATGCTGTCCGAGGCAGTCCTGCCATCAATGTGGCCGT

GCATGTGTTCAGAAAGGCTGCTGATGACACCTGGGAGCCATTTGCCTCTG

GGAAAACCAGTGAGTCTGGAGAGCTGCATGGGCTCACAACTGAGGAGGAA

TTTGTAGAAGGGATATACAAAGTGGAAATAGACACCAAATCTTACTGGAA

GGCACTTTGCATCTCCCCATTCCATGAGCATGCAGAGGTGGTATTCACAG

CCAACGACTCCGGCCCCCGCCGCTACACCATTGCCGCCCTGCTGAGCCCC

TACTCCTATTCCACCACGGCTGTCGTCACCAATCCCAAGGAATAA

TMP-TTRC10A/K15A/A81C (SEQ ID NO: 74):
ATGATCGAAGGTCCGACTCTGCGTCAGTGGCTGGCTGCTCGTGCTGGCGG

TGGTGGCGGAGGGGGTGGCATTGAGGGCCCAACCCTTCGCCAATGGCTTG

CAGCACGCGCAGGTCCAACTGGTACCGGTGAATCCAAGGCTCCTCTGATG

GTCGCAGTTCTAGATGCTGTCCGAGGCAGTCCTGCCATCAATGTGGCCGT

-continued

```
GCATGTGTTCAGAAAGGCTGCTGATGACACCTGGGAGCCATTTGCCTCTG

GGAAAACCAGTGAGTCTGGAGAGCTGCATGGGCTCACAACTGAGGAGGAA

TTTGTAGAAGGGATATACAAAGTGGAAATAGACACCAAATCTTACTGGAA

GTGTCTTGGCATCTCCCCATTCCATGAGCATGCAGAGGTGGTATTCACAG

CCAACGACTCCGGCCCCGCCGCTACACCATTGCCGCCCTGCTGAGCCCC

TACTCCTATTCCACCACGGCTGTCGTCACCAATCCCAAGGAATAA

TMP-TTRC10A/K15A/A37C (SEQ ID NO: 75):
ATGATCGAAGGTCCGACTCTGCGTCAGTGGCTGGCTGCTCGTGCTGGCGG

TGGTGGCGGAGGGGGTGGCATTGAGGGCCCAACCCTTCGCCAATGGCTTG

CAGCACGCGCAGGTCCAACTGGTACCGGTGAATCCAAGGCTCCTCTGATG

GTCGCAGTTCTAGATGCTGTCCGAGGCAGTCCTGCCATCAATGTGGCCGT

GCATGTGTTCAGAAAGGCTTGTGATGACACCTGGGAGCCATTTGCCTCTG

GGAAAACCAGTGAGTCTGGAGAGCTGCATGGGCTCACAACTGAGGAGGAA

TTTGTAGAAGGGATATACAAAGTGGAAATAGACACCAAATCTTACTGGAA

GGCACTTGGCATCTCCCCATTCCATGAGCATGCAGAGGTGGTATTCACAG

CCAACGACTCCGGCCCCGCCGCTACACCATTGCCGCCCTGCTGAGCCCC

TACTCCTATTCCACCACGGCTGTCGTCACCAATCCCAAGGAATAA
```

EXAMPLE 23

This example describes the expression of GLP-1 fusions proteins in *E. coli*. 25-100 ml of a saturated overnight culture was used to inoculate 50 ml TB with 20 ug/ml kanamycin in a 250 ml baffled flask and incubated at 37 C, 250 rpm overnight. 10-35 ml of these overnight cultures were used to inoculate 1 L TB with 20 ug/ml kanamycin in a 2 L baffled flask and incubated at 37 C, 250 rpm until the optical density at 600 nm reached approximately 0.7. The cultures were then induced to express recombinant protein by the addition of: 1 ml of ethanol containing 30 ug/ml N-(B-ketocaproyl)-DL-homoserine lactone (Sigma) in the case of pAMG21, or IPTG to 0.1 mM in the case of pAMG33*. The incubation was continued for an additional 2-4 hours and the cells were collected by centrifugation.

EXAMPLE 24

This example describes the purification of PTH-TTR (C10A/K15A/A81C). About 197 g of *E. coli* paste from clone 5933 stored at −80° C. was defrosted in 1480 ml of 50 mM tris HCl, 5 mM EDTA, pH 8.0. 60 tablets of Sigma protease inhibitor cocktail 1-873-580 (Saint Louis, Mo.) was dissolved in the cell suspension and the suspension was passed through a model 110-Y microfluidizer (Microfluidics, Newton, Mass.) twice at 14,000 PSI. The lysate was centrifuged at 11,325×g for 50 min 4° C. The supernatant was removed as the soluble fraction. The soluble fraction was heated in a 65° C. water bath for 30 minutes in polypropylene bottles, at which time the temperature of the contents was 63° C. The soluble fraction was centrifuged at 11,325×g for 50 minutes 4° C. The supernatant was removed as Heat Soluble. The heat soluble fraction was filtered through a 0.45 μm cellulose acetate filter with two prefilters and then loaded. on to a 240 ml Q-sepharose fast flow (5 cm ID) column (Amersham Pharmacia Biotech, Piscataway, N.J.) at 25 ml/min equilibrated in Q-Buffer A (20 mM tris HCl, 2.5 mM EDTA, pH 8.0) at room temperature (about 23° C.). Column was washed with about 2200 ml Q-Buffer A at 30 ml/min. Q-column was eluted with a 15 column volume linear gradient to 60% Q-Buffer B (20 mM tris HCl, 1 M NaCl, 2.5 mM EDTA, pH 8.0) followed by a 2 column volume step to 100% Q-Buffer B. Fractions containing the TTR fusion as determined by SDS-PAGE were pooled into a single Q-pool (1300 ml). To the Q-pool, 464 ml of 3.8 M ammonium sulfate pH 7.2 was slowly added. The solution was centrifuged at 11,325×g for 50 min 4° C. The supernatant was removed as the ammonium sulfate soluble fraction and discarded, and the pellet was resuspended in 450 ml 10 mM $NaH_2PO_4$, pH 7.0 by gentle agitation at room temperature for about 30 min. The solution was centrifuged at 11,325×g for 50 min 4° C. Supernatant was removed as phosphate buffer soluble fraction and filtered through a 0.45 μm cellulose acetate filter. Added 240 μl 1 M dithiothreitol to the phosphate buffer soluble fraction and loaded on to a 105 ml (2.6 cm) type 1 ceramic hydroxyapatite column (Bio-Rad Inc., Hercules, Calif.) at 10 ml/min in HA-Buffer A. Column was washed with approximately 210 ml HA-Buffer A at 10 ml/min followed by 3 steps of 25%, 50%, and 100% HA-Buffer B (400 mM $NaH_2PO_4$, pH 7.0). The fractions from the 50% elution were pooled as HA-pool (725 ml) and filtered through a 0.22 μm cellulose acetate filter. 1.16 g of dithiothreitol was added to HA-Pool, and the pH was raised to 8.0 using tris base followed by incubation at room temperature for about 30 minutes. Diluted HA-pool with 750 ml water and loaded on to a 50 ml source 15Q (2.6 cm ID) column (Amersham Pharmacia Biotech) at 10 ml/min followed by a wash with about 250 ml Q-Buffer A. Column was eluted with a 20 column volume linear gradient from 10% to 60% Q-Buffer B followed a step of 2 column volumes of 100% Q-Buffer B. Fractions containing the TTR fusion as determined by SDS-PAGE were pooled into a single Q2-pool (170 ml) and filtered through a 0.22 μm cellulose acetate filter. The protein concentration was determined to be 3.7 mg/ml using a calculated extinction coefficient of 23,950 $M^{-1}$ $cm^{-1}$. The pyrogen level was determined to be <1 EU/mg of protein using the Limulus Ameboycyte Lysate assay (Associates of Cape Cod, Falmouth, Mass.). The nucleic acid content was determined to be negligible, since the ratio of the absorbance at 260 nm over 280 nm was determined to be 0.61.

EXAMPLE 25

This example describes the purification of TMP-TTR (C10A/D38C). About 170 g of *E. coli* paste from clone 5705 stored at −80° C. was defrosted in 1275 ml of 50 mM tris HCl, 5 mM EDTA, pH 8.0. 50 tablets of Sigma protease inhibitor cocktail 1-873-580 (Saint Louis, Mo.) was dissolved in the cell suspension and the suspension was passed through a model 110-Y microfluidizer (Microfluidics, Newton, Mass.) twice at 14,000 PSI. The lysate was centrifuged at 11,325×g for 30 min 4° C. The supernatant was removed as the soluble fraction and discarded. The pellets were resuspended in 1200 ml water using a tissue grinder and 20 more Sigma protease inhibitor tablets were added. The suspension was centrifuged at 11,325×g for 30 min 4° C. The supernatant was filtered through a Whatman GF/A filter and 2.1 g of dithiothreitol was added followed by incubation at 7° C. for 30 minutes. The reduced sample was loaded on to a 240 ml Q-sepharose fast flow (5 cm ID) column (Amersham Pharmacia Biotech, Piscataway, N.J.) at 30 ml/min equilibrated in Q-Buffer A (20 mM tris HCl, 0.02% sodium azide, pH 8.0) at 7° C. Column was washed with about 1920 ml Q-Buffer A at 30 ml/min. Q-column was eluted with 3 steps of 20%, 35%, and 100% Q-Buffer B (20 mM tris HCl, 1 M NaCl, 0.02% sodium azide, pH 8.0). Added 13 ml 500 mM EDTA pH 8.0 to the flowthrough from the Q-column and centrifuged for 30 min at 11,325 g at 4° C. Supernatant was discarded, and the pellet was resuspended in 700 ml 4 M urea, 20 mM tris HCl, pH 8.0. The urea solublized pellet was then filtered through a Whatman GF/A filter and loaded on to a 240 ml Q-sepharose fast flow (5 cm ID) column (Amersham Pharmacia Biotech, Piscataway, N.J.) at 30 ml/min equilibrated in Q-Buffer A (20 mM tris HCl, 0.02% sodium azide, pH 8.0) at 7° C. Column was washed with about 1920 ml Q-Buffer A at 30 ml/min. Q-column was eluted with 3 steps of 20%, 35%, and 100% Q-Buffer B (20 mM tris HCl, 1 M NaCl, 0.02% sodium azide, pH 8.0) at 15 ml/min. Fractions containing the 35% elution peak were pooled, filtered through a 0.22 µm cellulose acetate filter, and 0.5 g of dithiothreitol (10 mM final concentration) was added followed by incubation for 30 min at 7° C. The 35% Q-pool was then loaded on to a 45 ml (2.6 cm) type 1 ceramic hydroxyapatite column (Bio-Rad Inc., Hercules, Calif.) at 5 ml/min in 20 mM tris HCl, 350 mM NaCl, pH 8.0 at 7° C. Column was washed with approximately 70 ml 20 mM tris HCl, 350 mM NaCl, pH 8.0 at 5 ml/min followed by 3 steps of 2.5%, 25%, and 100% HA-Buffer B (400 mM $NaH_2PO_4$, pH 7.0). The fractions from the 2.5% elution were pooled as HA-pool (80 ml) and filtered through a 0.22 µm cellulose acetate filter. The protein concentration was determined to be 6.8 mg/ml using a calculated extinction coefficient of 29,450 $M^{-1} cm^{-1}$. The pyrogen level was determined to be <1 EU/mg of protein using the Limulus Ameboycyte Lysate assay (Associates of Cape Cod, Falmouth, Mass.). The nucleic acid content was determined to be negligible, since the ratio of the absorbance at 260 nm over 280 nm was determined to be 0.54.

EXAMPLE 26

This example describes the refolding and purification of TTR(C10A)-CH2-TMP. About 23 g of *E. coli* paste from clone 6104 stored at −80° C. was defrosted in 200 ml of 50 mM tris HCl, 5 mM EDTA, pH 8.0. 10 tablets of Sigma protease inhibitor cocktail 1-873-580 (Saint Louis, Mo.) was dissolved in the cell suspension and the suspension was passed through a microfluidizer (Microfluidics, Newton, Mass.) twice at 12,000 PSI. The lysate was centrifuged at 15,344×g for 50 min 4° C. The supernatant was removed as the soluble fraction and discarded. The pellet was resuspended in 200 ml 50 mM tris HCl, 5 mM EDTA, pH 8.0 using a tissue grinder. The suspension was centrifuged at 15,344×g for 50 min 4° C. The supernatant was removed as the wash and discarded. The pellet was resuspended in 50 ml 50 mM tris HCl, 5 mM EDTA, pH 8.0 using a tissue grinder. The suspension was centrifuged at 14,000×g for 10 min room temperature. The supernatant was removed as the wash and discarded. The pellets were dissolved in 50 ml 8 M guanidine HCl, 50 mM tris HCl, pH 8.0 using a sonicator for about 1 min. Dissolved protein was reduced for 30 min room temperature by adding 500 µl 1 M DTT. Reduced protein was centrifuged for 30 min at 20° C. at 27,216 g. Supernatant was then added to 4 L 50 mM tris base, 160 mM arginine base, 1 M urea, 1 mM cystamine, 4 mM cysteine, pH 9.5 at 2 ml/min and incubated about 16 hours 4° C. Refolded protein was then filtered through a Gellman SUPORCAP® 50 and then concentrated to about 500 ml using a Pall Filtron 3 square foot YM10 membrane tangential flow system followed by diafiltration against 2 L 20 mM tris HCl pH 8.0. Concentrated protein was then loaded on to a 45 ml source 15Q (2.6 cm ID) column (Amersham Pharmacia Biotech) at 18 ml/min followed by a wash with about 150 ml Q-Buffer A (20 mM tris HCl pH 8.0). Column was eluted with a 20 column volume linear gradient from 0% to 60% Q-Buffer B followed a step of 2 column volumes of 100% Q-Buffer B. Fractions containing the TTR fusion as determined by SDS-PAGE were pooled into a single Q-pool (29 ml). The Q-Pool was then concentrated to about 6.3 ml using a Millipore CENTRIPREP™ 10 and then passed through a Pall ACRODISC® MUSTANG™ E membrane filter at 1 ml/min. The protein concentration was determined to be 10.5 mg/ml using a calculated extinction coefficient of 46,410 $M^{-1} cm^{-1}$. The pyrogen level was determined to be <1 EU/mg of protein using the Limulus Ameboycyte Lysate assay (Associates of Cape Cod, Falmouth, Mass.). The nucleic acid content was determined to be negligible, since the ratio of the absorbance at 260 nm over 280 nm was determined to be 0.51.

EXAMPLE 27

This example describes the purification of GLP1-TTR (C10A/K15A/G83C). About 30 g of *E. coli* paste from clone 6450 stored at −80° C. was defrosted in 250 ml of 50 mM $NaH_2PO_4$, pH 7.0. Cell suspension was passed through a microfluidizer (Microfluidics, Newton, Mass.) twice at 12,000 PSI. The lysate was centrifuged at 15,344×g for 50 min 4° C. The supernatant was discarded as the soluble fraction, and the pellet was resuspended in 200 ml deoxycholate using a tissue grinder. The suspension was centrifuged at 15,344×g for 50 min 4° C. The supernatant was discarded as the wash, and the pellet was resuspended in 200 ml water using a tissue grinder. The suspension was centrifuged at 15,344×g for 50 min 4° C. The supernatant was discarded as the wash, and the pellet was resuspended in 100 ml water using a tissue grinder. The suspension was centrifuged at 27,216×g for 30 min room temperature. The supernatant was discarded as the wash, and about ⅔ of the pellets were dissolved in 75 ml 8 M guanidine HCl, 50 mM tris HCl, pH 8.0 by agitation for about 15 min. The suspension was centrifuged at 27,216×g for 30 min room temperature, and the supernatant was diluted with 18 ml water. Sample was then loaded on to a 50 ml chelating sepharose fast flow column (Amersham Pharmacia Biotech, Piscataway, N.J.), loaded with $NiCl_2$, at 5 ml/min. After washing with about 150 ml Ni-Buffer A (6 M guanidine HCl, 37.5 ml tris HCl, pH 8.0) at 10 ml/min, eluted with two step of 10% and 100% Ni-Buffer B (6 M guanidine HCl, 37.5 mM tris HCl, 400 mM imidazole, pH 8.0). Combined the peak containing the fusion construct as Ni-Pool (40 ml) and determined the protein content to be 6.4 mg/ml by observing the absorbance at 280 nm in 8 M guanidine HCl using an extinction coefficient of 25,440 $M^{-1}$. Added 800 µl 500 mM EDTA pH 8.0 and removed 80 mg of protein for the PEGylation reaction. Added 230 µl 1 M DTT and incubated for 30 min at 30° C. Loaded on to a 130 ml SEPHADEX™ G25 medium column (2.6 cm ID) (Amersham Pharmacia Biotech, Piscataway, N.J.) at 8 ml/min in 20 mM tris HCl, 6 M urea, pH 8.5. Pooled the protein peak as determined by absorbance at 280 nm (22 ml) and determined the concentration to be 3.2 mg/ml by observing the absorbance at 280 nm in 20 mM tris HCl, 6 M urea, pH 8.5 using an extinction coefficient of 25,440 $M^{-1}$. Reacted 45% of the buffer exchanged material with 950 µl of 5 mM methoxy-PEG-maleimide 5K (Shearwater Corporation, Huntsville, Ala.) for 140 min at 30° C. Added 100 µl 1 M 2-mercaptoethanol to each reaction to quench. Dialyzed reaction against 1 L 25 mM $NaH_2PO_4$, 3 M urea, pH 7.25 using a Pierce 10 kDa Slidealyzer for 2 hour room temperature. Changed the dialysis buffer for 25 mM $NaH_2PO_4$, 10% sucrose, 2 mM EDTA, pH 7.25 and incubated for about 16 hours room temperature.

Added 140 μl 5% CHAPS and 7.28 μl 2-mercaptoethanol and 0.475 ml of 3 mg/ml caspase 3 followed by a 2 hour incubation at room temperature. Reaction mixture was loaded on to a 5 ml HiTrap Q-sepharose HP column (Amersham Pharmacia Biotech, Piscataway, N.J.) at 1 ml/min in 20 mM tris HCl pH 8.0 followed by about a 15 ml wash in the same buffer. Column was then developed at 5 ml/min using a linear gradient to 60% 20 mM tris HCl, 1 M NaCl, pH 8.0 followed by a step to 100% of the elution buffer. Fractions containing the TTR fusion as determined by SDS-PAGE were pooled into a single Q-pool (9.5 ml). Concentrated Q-Pool to 3.2 ml using a Millipore CENTRIPREP™ 30 kDa and filtered through a Pall MUSTANG™ E membrane at about 1 ml/min. Diluted Q-Pool to 6.5 ml with water and added 375 μl acetonitrile. Injected on to a Vydac Protein/Peptide 10×250 mm $C_4$ column (Vydac, Hisperia, Calif.) in 95% RP-Buffer A (0.1% trifluoroacetic acid) with 5% RP-Buffer B (95% acetonitrile, 0.1% trifluoroacetic acid) at 5 ml/min. Developed column running a linear gradient to 100% RP-Buffer B. Concentrated protein peak to about 3 ml using a Millipore CENTRIPREP™ 30 kDa and diluted to 15 ml using 20 mM tris HCl pH 8.0. Repeated buffer exchange 3 more times then passed though a Pall MUSTANG™ E membrane at about 1 ml/min. The protein concentration was determined to be 7.7 mg/ml using a calculated extinction coefficient of 25,440 $M^{-1}$ $cm^{-1}$. The pyrogen level was determined to be <1 EU/mg of protein using the Limulus Ameboycyte Lysate assay (Associates of Cape Cod, Falmouth, Mass.). The nucleic acid content was determined to be negligible, since the ratio of the absorbance at 260 nm over 280 nm was determined to be 0.54.

EXAMPLE 28

This example shows the effect of injecting pegylated GLP1-TTR constructs into mice on blood glucose levels. For this example 40 male, db/db, 9 week-old mice were split into 4 groups and injected (hour 0) intraperitoneal with 7.4-16.6 mg test protein per animal (538 pmol monomers for all groups) (5K pegylated GLP1-TTR fusion construct 10 mg, 20K pegylated GLP1-TTR fusion construct 10 mg, GLP1-Fc 16.6 mg, and a TTR(C10A) control 7.4 mg). Each group was bled at time points 0(baseline measurement), 1, 4, 6, 12, 24, and 48 hours post injection. Food was withheld from the mice for the first 6 hours of the experiment and replaced after the bleed at the 6 hour time point.

Figure 12:
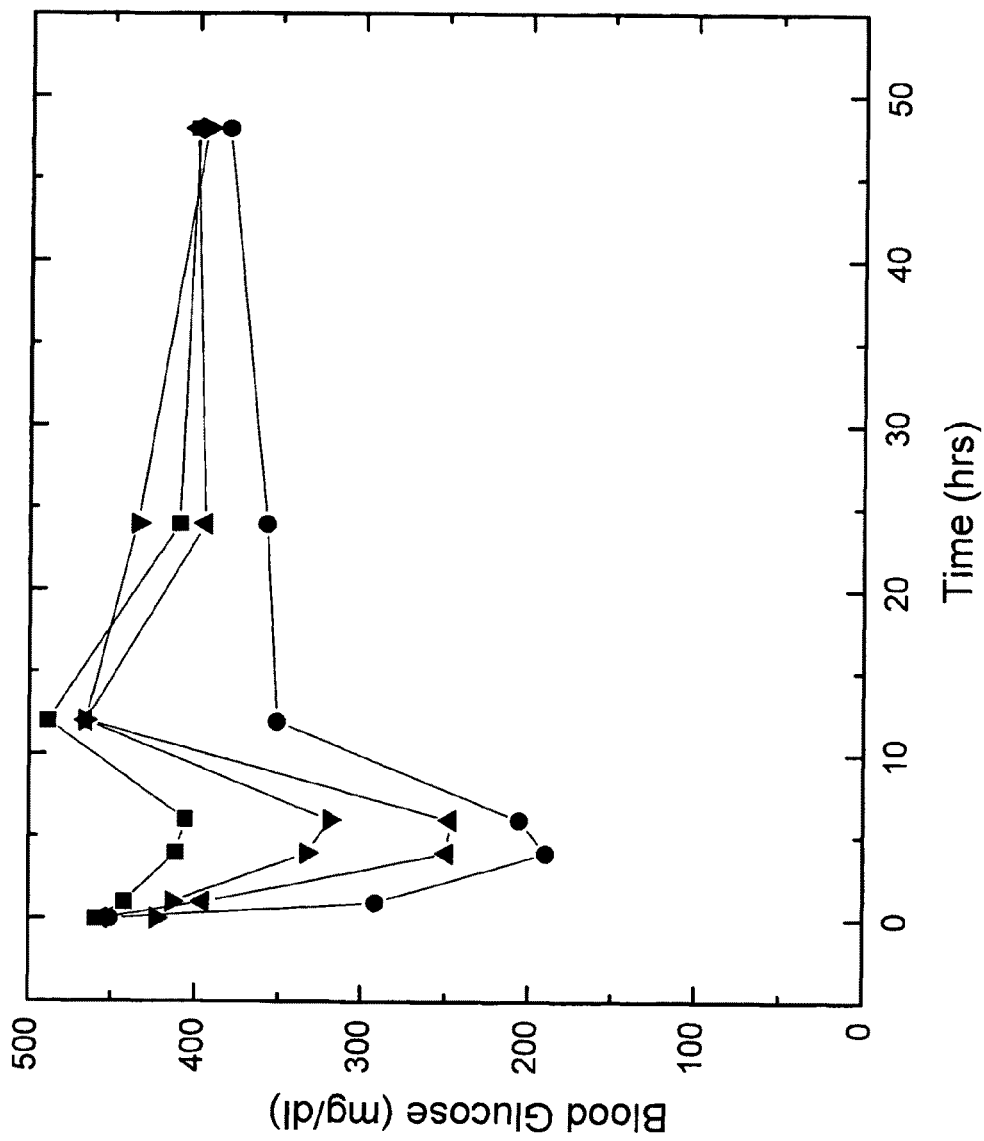
FIG. 12 shows that injection of Glucagon-like Peptide 1 (GLP1)-TTR with PEG conjugated to engineered cysteines lowers blood glucose levels in mice. The following symbols correspond to the corresponding constructs: ■ TTR(C10A), ● GLP1-Fc, ▲ GLP1-TTR(C10A/K15A/G83C) (PEG 5K), and ▼ GLP1-TTR(C10A/K15A/G83C) (PEG 20K).

Each collected drop of blood per time point was analyzed for glucose content using a One Touch Profile glucose meter and the results are depicted in FIG. 12.

EXAMPLE 29

This example shows the effect of injecting TMP-TTR constructs with fused antibody CH2 domains into mice on blood platelet count. For this example 50 female BDF1 mice were split into 5 groups and injected (day 0) subcutaneously with 50 mg test protein per kg animal (TMP fusion construct, Fc-TMP, or a TTR(C10A) control). Each group was divided in half and bled (140 ml) on alternate time points (day 0, 3, 5, 7, and 10). Mice were anesthetized with isoflurane prior to collection.

Figure 13:
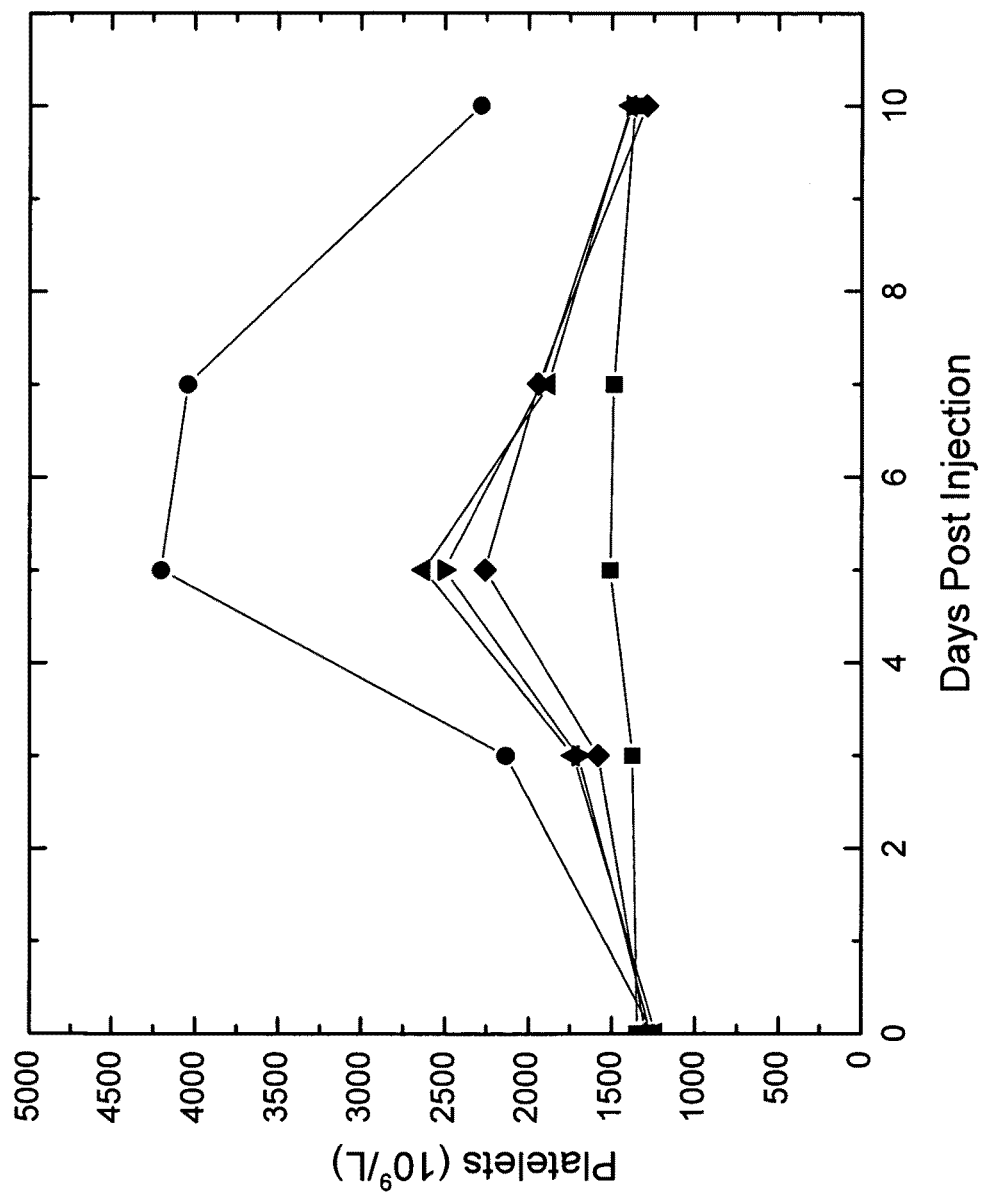
FIG. 13 shows that injection of TMP-TTR conjugates with fused CH2 domains increase serum platelet levels in mice. The following symbols correspond to the corresponding constructs: ■ TTR(C10A), ● Fc-TMP, ▲ TMP-TTR(C10A)-CH2, ▼ TTR(C10A)-CH2-TMP, and ♦ TMP-CH2-TTR (C10A).

The collected blood was analyzed for a complete and differential count using an ADVIA 120 automated blood analyzer with murine software (Bayer Diagnostics, New York, N.Y.). As seen in FIG. 13, Fc-TMP showed the greatest response with platelet count rising to over 4.2×1012 platelets L-1 on day 5 which is 3 times baseline at 1.4×1012 platelets L-1. All three of the CH2 fused TMP-TTR constructs preformed better than the control, but not as well as Fc-TMP with platelet counts between 2.3×1012 and 2.6×1012 platelets L-1 on day 5, which is between a 64% and 86% improvement over baseline.

EXAMPLE 30

This example shows the effect of injecting pegylated TTR constructs with TMP fused to the carboxy-terminus of pegylated TTR into mice on blood platelet count. For this example 80 BDF1 mice were split into 8 groups and injected (day 0) subcutaneously with 50 mg test protein per kg animal (TMP fusion constructs, Fc-TMP, or a TTR(C10A) control). Each group was divided in half and bled (140 ml) on alternate time points (day 0, 3, 5, 7, 10, and 12). Mice were anesthetized with isoflurane prior to collection.

Figure 14:
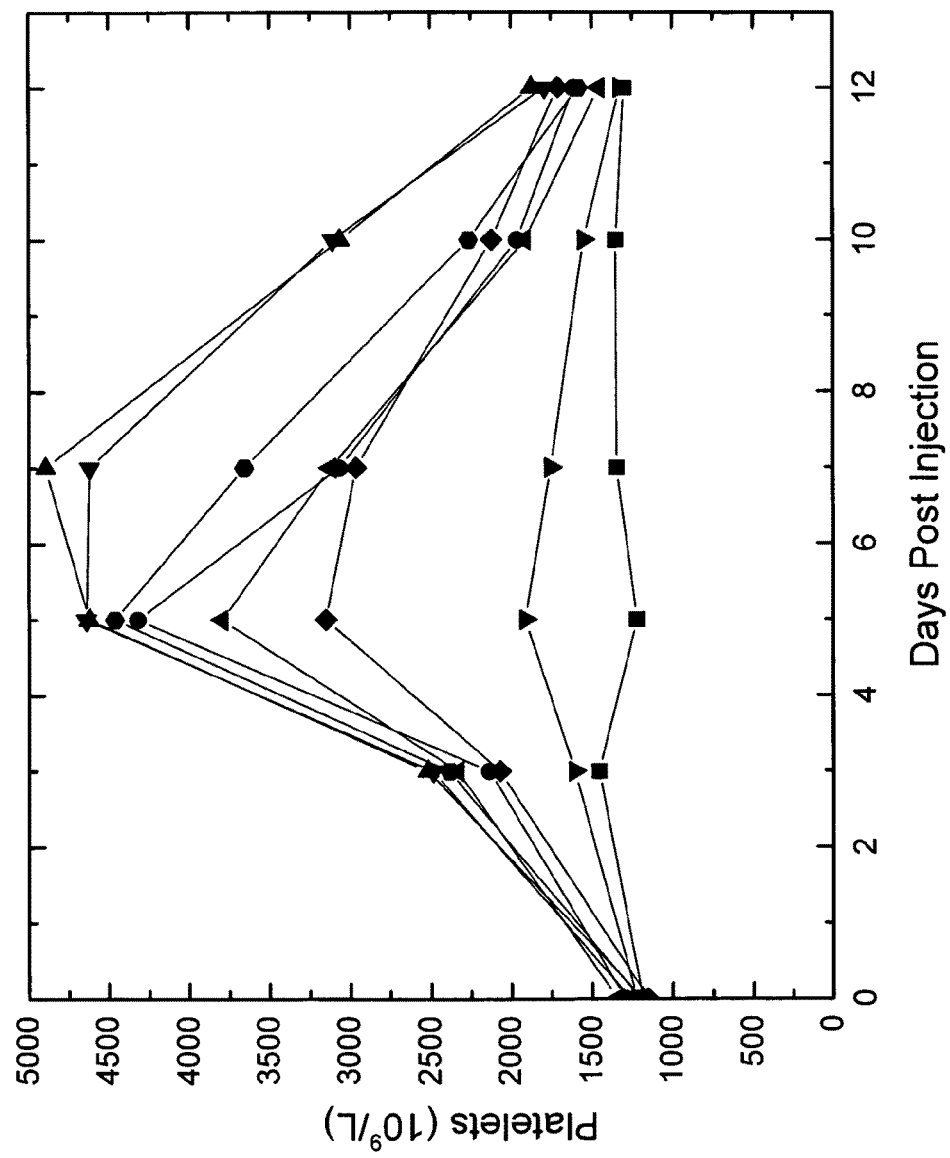
FIG. 14 shows that injection of and carboxy-terminal fusions of TMP with pegylated TTR increases blood platelet counts in mice. The following symbols correspond to the corresponding constructs: ■ TTR(C10A), ● Fc-TMP, ▲ TTR(C10A/K15A/A37C)-TMP (PEG 20K), ▼ TTR(C10A/K15A/A81C)-TMP (PEG 20K), ♦ TTR(C10A/K15A/G83C)-TMP (PEG 20K), ◄ TMP-TTR(C10A/K15A/A37C) (PEG 20K), ► TMP-TTR(C10A/K15A/A81C) (PEG 20K), ● TMP-TTR(C10A/K15A/G83C) (PEG 20K).

The collected blood was analyzed for a complete and differential count using an ADVIA 120 automated blood analyzer with murine software (Bayer Diagnostics, New York, N.Y.). As seen in FIG. 14, Fc-TMP and the three amino terminal (TMP-TTR) fusions showed the greatest response with platelet count rising between $4.3 \times 10^{12}$ and $4.6 \times 10^{12}$ platelets L-1 on day 5 which is over three times baseline at $1.3 \times 10^{12}$ platelets L-1. All three of the carboxy terminal (TTR-TMP) constructs performed better than the control.

EXAMPLE 31

This example shows the effect of injecting pegylated TTR-TMP constructs containing a K15A alteration into mice on blood platelet count. For this example 120 BDF1 mice were split into 12 groups and injected (day 0) subcutaneously with 50 mg test protein per kg animal (TMP fusion constructs, Fc-TMP, or a TTR(C10A) control) (this study was split into two batches (PEG 20K in one and the PEG 5K and non-pegylated samples in the other) completed at separate times with repeated controls). Each group was divided in half and bled (140 ml) on alternate time points (day 0, 3, 5, 7, 10, and 12). Mice were anesthetized with isoflurane prior to collection.

Figure 15:
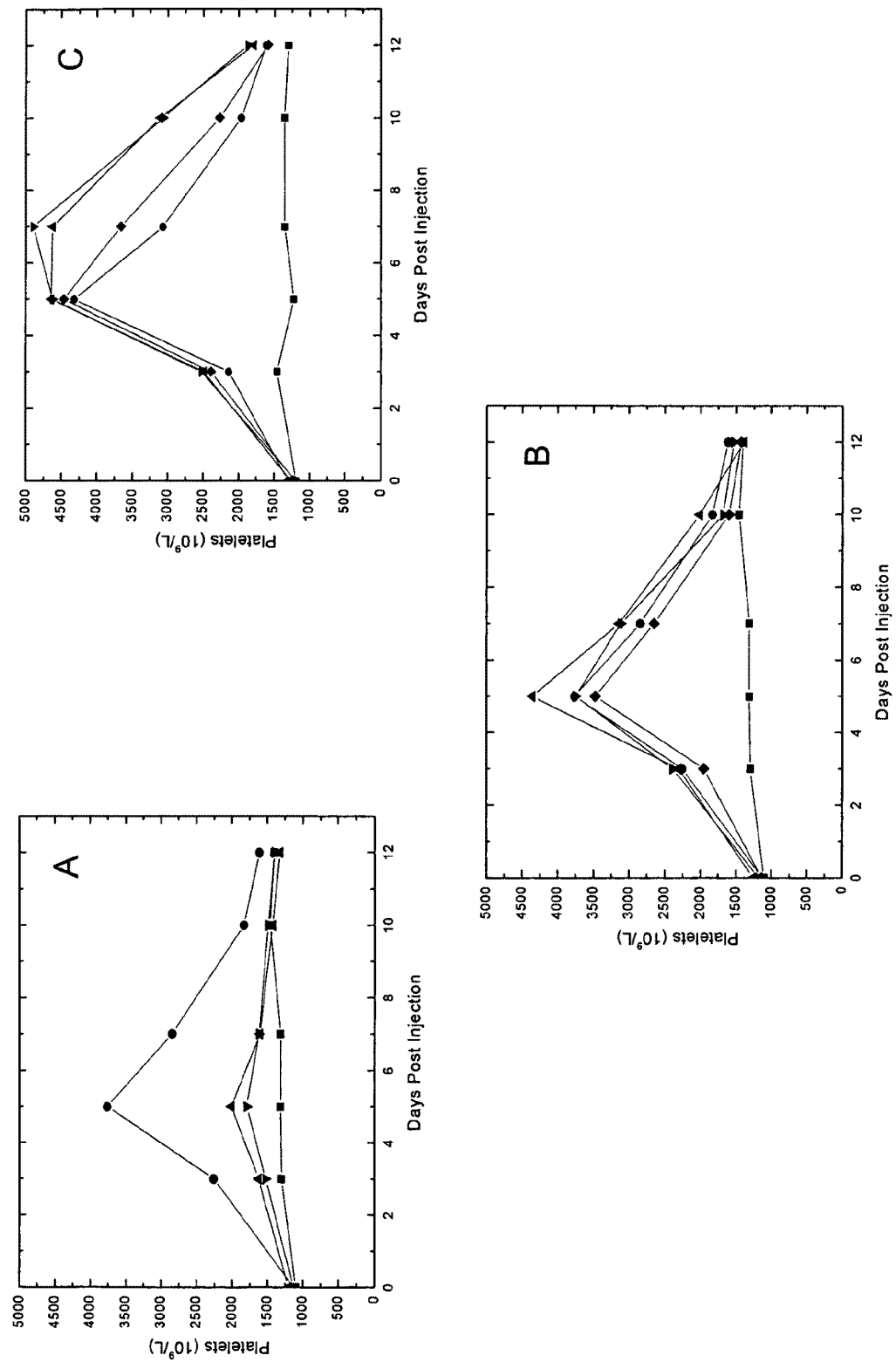
FIGS. 15 A-C show that injection of pegylated TMP-TTR fusions containing a K15A alteration increases blood platelet counts in mice. The following symbols correspond to the corresponding constructs: A) ■ TTR(C10A), ● Fc-TMP, ▲ TMP-TTR(C10A/K15A/A37C) (carboxyamidomethylated), and ▼ TMP-TTR(C10A/K15A/A81C) (carboxyamidomethylated); B) ■ TTR(C10A), ● Fc-TMP, ▲ TMP-TTR (C10A/K15A/A37C) (PEG 5K), ▼ TMP-TTR(C10A/K15A/A81C) (PEG 5K), and ♦ TMP-TTR(C10A/K15A/G83C) (PEG 5K); C) ■ TTR(C10A), ● Fc-TMP, ▲ TMP-TTR (C10A/K15A/A37C) (PEG 20K), ▼ TMP-TTR(C10A/K15A/A81C) (PEG 20K), and ♦ TMP-TTR(C10A/K15A/G83C) (PEG 20K).

The collected blood was analyzed for a complete and differential count using an ADVIA 120 automated blood analyzer with murine software (Bayer Diagnostics, New York, N.Y.). As seen in FIG. 15A, the two non-pegylated constructs outperformed the baseline ($1.3 \times 10^{12}$ platelets L-1) with platelet responses at day 5 rising between $1.8 \times 10^{12}$ and $2.0 \times 10^{12}$ platelets L-1. As seen in FIG. 15B, Fc-TMP and the three 5K pegylated fusions showed equivalent responses at day 5 with platelet counts rising between $3.5 \times 10^{12}$ and $4.4 \times 10^{12}$ platelets L-1 which is at least 2.7 times baseline ($1.3 \times 10^{12}$ platelets L-1). As seen in FIG. 15C, Fc-TMP and the three 20K pegylated fusions showed equivalent responses at day 5 with platelet count rising between $4.3 \times 10^{12}$ and $4.6 \times 10^{12}$ platelets L-1 which is over three times baseline at $1.3 \times 10^{12}$ platelets L-1.

In addition, the 20K pegylated TTR constructs appear to have an improved sustained response with platelets at day 7 ranging from $3.7 \times 10^{12}$ to $4.9 \times 10^{12}$ platelets L-1 compared to Fc-TMP at $3.1 \times 10^{12}$ platelets L-1. This sustained response is maintained at day 10 for the three 20K pegylated TTR constructs with platelets ranging from $2.3 \times 10^{12}$ to $3.1 \times 10^{12}$ platelets L-1 compared to Fc-TMP at $2.0 \times 10^{12}$ platelets L-1.

What is claimed is:

1. An isolated transthyretin (TTR) variant comprising the amino acid sequence as set forth in SEQ ID NO:1 having two to three amino acid substitutions, wherein the cysteine at position 10 and the lysine at position 15 of SEQ ID NO:1 are substituted for another amino acid.

2. The TTR variant of claim 1, wherein the cysteine at position 10 is substituted for alanine.

3. The TTR variant of claim 1, wherein one or more amino acids is substituted to cysteine.

4. The TTR variant of claim 3, wherein the amino acid substituted to cysteine is selected from the group consisting of A37, D38, A81, and G83.

5. The TTR variant of claim 4, wherein the amino acid substituted to cysteine is A81.

6. The TTR variant of claim 4, wherein the amino acid substituted to cysteine is G83.

7. The TTR variant of claim 1, wherein the lysine at position 15 is substituted for alanine.

8. The TTR variant of claim 1, wherein the TTR variant is chemically modified with a chemical selected from the group consisting of dextran, poly(n-vinyl pyrrolidone), polyethylene glycols, propylene glycol homopolymers, polypropylene oxide/ethylene oxide co-polymers, polyoxyethylated polyols, and polyvinyl alcohols.

9. The TTR variant of claim 8, wherein the TTR variant is chemically modified with polyethylene glycol (PEG).

10. The TTR variant of claim 9, wherein the PEG has a molecular weight of about 1 kD to about 100 kD.

11. The TTR variant of claim 10, wherein the PEG has a molecular weight of about 5 kD to about 30 kD.

12. A fusion protein or TTR-peptide fusion comprising a biologically active protein fused to the TTR variant of claim 1, wherein said fusion protein or TTR-peptide fusion has a longer half-life in serum than the biologically active protein lacking the TTR variant.

13. The fusion protein or TTR-peptide fusion of claim 12, wherein the biologically active protein is fused to the TTR variant of claim 8.

14. A method of increasing the half-life in serum of a biologically active protein, said method comprising fusing said biologically active protein to a TTR variant of claim 1.

15. A method of increasing the half-life in serum of a biologically active protein, said method comprising fusing said biologically active protein to a TTR variant of claim 8.

* * * * *

SEQUENCE LISTING

<160> NUMBER OF SEQ ID NOS: 75

<210> SEQ ID NO 1
<211> LENGTH: 127
<212> TYPE: PRT
<213> ORGANISM: Homo sapiens

<400> SEQUENCE: 1

Gly Pro Thr Gly Thr Gly Glu Ser Lys Cys Pro Leu Met Val Lys Val
 1               5                  10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
        115                 120                 125

<210> SEQ ID NO 2
<211> LENGTH: 387
<212> TYPE: DNA
<213> ORGANISM: Homo sapiens

<400> SEQUENCE: 2
agtggtccaa ctggtaccgg tgaatccaag tgtcctctga tggtcaaagt tctagatgct      60
gtccgaggca gtcctgccat caatgtggcc gtgcatgtgt tcagaaaggc tgctgatgac     120
acctgggagc catttgcctc tgggaaaacc agtgagtctg gagagctgca tgggctcaca     180
actgaggagg aatttgtaga agggatatac aaagtggaaa tagacaccaa atcttactgg     240
aaggcacttg gcatctcccc attccatgag catgcagagg tggtattcac agccaacgac     300
tccggccccc gccgctacac cattgccgcc ctgctgagcc cctactccta ttccaccacg     360
gctgtcgtca ccaatcccaa ggaataa                                         387

<210> SEQ ID NO 3
<211> LENGTH: 387
<212> TYPE: DNA
<213> ORGANISM: Homo sapiens

<400> SEQUENCE: 3
atgggtccaa ctggtaccgg tgaatccaag gctcctctga tggtcaaagt tctagatgct      60
gtccgaggca gtcctgccat caatgtggcc gtgcatgtgt tcagaaaggc tgctgatgac     120
acctgggagc catttgcctc tgggaaaacc agtgagtctg gagagctgca tgggctcaca     180
actgaggagg aatttgtaga agggatatac aaagtggaaa tagacaccaa atcttactgg     240
aaggcacttg gcatctcccc attccatgag catgcagagg tggtattcac agccaacgac     300
tccggccccc gccgctacac cattgccgcc ctgctgagcc cctactccta ttccaccacg     360
gctgtcgtca ccaatcccaa ggaataa                                         387

<210> SEQ ID NO 4
<211> LENGTH: 387
<212> TYPE: DNA
<213> ORGANISM: Homo sapiens

<400> SEQUENCE: 4

```
atgggtccaa ctggtaccgg tgaatccaag gctcctctga tggtcaaagt tctagatgct    60
gtccgaggca gtcctgccat caatgtggcc gtgcatgtgt tcagaaaggc ttgtgatgac   120
acctgggagc catttgcctc tgggaaaacc agtgagtctg gagagctgca tgggctcaca   180
actgaggagg aatttgtaga agggatatac aaagtggaaa tagacaccaa atcttactgg   240
aaggcacttg gcatctcccc attccatgag catgcagagg tggtattcac agccaacgac   300
tccggccccc gccgctacac cattgccgcc ctgctgagcc cctactccta ttccaccacg   360
gctgtcgtca ccaatcccaa ggaataa                                       387
```

<210> SEQ ID NO 5
<211> LENGTH: 387
<212> TYPE: DNA
<213> ORGANISM: Homo sapiens

<400> SEQUENCE: 5

```
atgggtccaa ctggtaccgg tgaatccaag gctcctctga tggtcaaagt tctagatgct    60
gtccgaggca gtcctgccat caatgtggcc gtgcatgtgt tcagaaaggc tgcttgtgac   120
acctgggagc catttgcctc tgggaaaacc agtgagtctg gagagctgca tgggctcaca   180
actgaggagg aatttgtaga agggatatac aaagtggaaa tagacaccaa atcttactgg   240
aaggcacttg gcatctcccc attccatgag catgcagagg tggtattcac agccaacgac   300
tccggccccc gccgctacac cattgccgcc ctgctgagcc cctactccta ttccaccacg   360
gctgtcgtca ccaatcccaa ggaataa                                       387
```

<210> SEQ ID NO 6
<211> LENGTH: 387
<212> TYPE: DNA
<213> ORGANISM: Homo sapiens

<400> SEQUENCE: 6

```
atgggtccaa ctggtaccgg tgaatccaag gctcctctga tggtcaaagt tctagatgct    60
gtccgaggca gtcctgccat caatgtggcc gtgcatgtgt tcagaaaggc tgctgatgac   120
acctgggagc catttgcctc tgggaaaacc agtgagtctg gagagctgca tgggctcaca   180
actgaggagg aatttgtaga agggatatac aaagtggaaa tagacaccaa atcttactgg   240
aagtgtcttg gcatctcccc attccatgag catgcagagg tggtattcac agccaacgac   300
tccggccccc gccgctacac cattgccgcc ctgctgagcc cctactccta ttccaccacg   360
gctgtcgtca ccaatcccaa ggaataa                                       387
```

<210> SEQ ID NO 7
<211> LENGTH: 387
<212> TYPE: DNA
<213> ORGANISM: Homo sapiens

<400> SEQUENCE: 7

```
atgggtccaa ctggtaccgg tgaatccaag gctcctctga tggtcaaagt tctagatgct    60
gtccgaggca gtcctgccat caatgtggcc gtgcatgtgt tcagaaaggc tgctgatgac   120
acctgggagc catttgcctc tgggaaaacc agtgagtctg gagagctgca tgggctcaca   180
```

| | |
|---|---|
| actgaggagg aatttgtaga agggatatac aaagtggaaa tagacaccaa atcttactgg | 240 |
| aaggcacttt gcatctcccc attccatgag catgcagagg tggtattcac agccaacgac | 300 |
| tccggccccc gccgctacac cattgccgcc ctgctgagcc cctactccta ttccaccacg | 360 |
| gctgtcgtca ccaatcccaa ggaataa | 387 |

<210> SEQ ID NO 8
<211> LENGTH: 387
<212> TYPE: DNA
<213> ORGANISM: Homo sapiens

<400> SEQUENCE: 8

| | |
|---|---|
| atgggtccaa ctggtaccgg tgaatccaag ctcctctga tggtcgcagt tctagatgct | 60 |
| gtccgaggca gtcctgccat caatgtggcc gtgcatgtgt tcagaaaggc tgctgatgac | 120 |
| acctgggagc catttgcctc tgggaaaacc agtgagtctg gagagctgca tgggctcaca | 180 |
| actgaggagg aatttgtaga agggatatac aaagtggaaa tagacaccaa atcttactgg | 240 |
| aaggcacttt gcatctcccc attccatgag catgcagagg tggtattcac agccaacgac | 300 |
| tccggccccc gccgctacac cattgccgcc ctgctgagcc cctactccta ttccaccacg | 360 |
| gctgtcgtca ccaatcccaa ggaataa | 387 |

<210> SEQ ID NO 9
<211> LENGTH: 495
<212> TYPE: DNA
<213> ORGANISM: Homo sapiens

<400> SEQUENCE: 9

| | |
|---|---|
| atgatcgaag gtccgactct gcgtcagtgg ctggctgctc gtgctggcgg tggtggcgga | 60 |
| gggggtggca ttgagggccc aacccttcgc caatggcttg cagcacgcgc aggtccaact | 120 |
| ggtaccggtg aatccaagtg tcctctgatg gtcaaagttc tagatgctgt ccgaggcagt | 180 |
| cctgccatca atgtggccgt gcatgtgttc agaaaggctg ctgatgacac ctgggagcca | 240 |
| tttgcctctg ggaaaaccag tgagtctgga gagctgcatg gctcacaac tgaggaggaa | 300 |
| tttgtagaag ggatatacaa agtggaaata gacaccaaat cttactggaa ggcacttggc | 360 |
| atctccccat tccatgagca tgcagaggtg gtattcacag ccaacgactc cggccccgc | 420 |
| cgctacacca ttgccgccct gctgagcccc tactcctatt ccaccacggc tgtcgtcacc | 480 |
| aatcccaagg aataa | 495 |

<210> SEQ ID NO 10
<211> LENGTH: 495
<212> TYPE: DNA
<213> ORGANISM: Homo sapiens

<400> SEQUENCE: 10

| | |
|---|---|
| atgatcgaag gtccgactct gcgtcagtgg ctggctgctc gtgctggcgg tggtggcgga | 60 |
| gggggtggca ttgagggccc aacccttcgc caatggcttg cagcacgcgc aggtccaact | 120 |
| ggtaccggtg aatccaaggc tcctctgatg gtcaaagttc tagatgctgt ccgaggcagt | 180 |
| cctgccatca atgtggccgt gcatgtgttc agaaaggctt gtgatgacac ctgggagcca | 240 |
| tttgcctctg ggaaaaccag tgagtctgga gagctgcatg gctcacaac tgaggaggaa | 300 |
| tttgtagaag ggatatacaa agtggaaata gacaccaaat cttactggaa ggcacttggc | 360 |
| atctccccat tccatgagca tgcagaggtg gtattcacag ccaacgactc cggccccgc | 420 |
| cgctacacca ttgccgccct gctgagcccc tactcctatt ccaccacggc tgtcgtcacc | 480 |

```
aatcccaagg aataa                                                      495
```

<210> SEQ ID NO 11
<211> LENGTH: 495
<212> TYPE: DNA
<213> ORGANISM: Homo sapiens

<400> SEQUENCE: 11

```
atgatcgaag gtccgactct gcgtcagtgg ctggctgctc gtgctggcgg tggtggcgga       60
gggggtggca ttgagggccc aacccttcgc caatggcttg cagcacgcgc aggtccaact      120
ggtaccggtg aatccaaggc tcctctgatg gtcaaagttc tagatgctgt ccgaggcagt      180
cctgccatca atgtggccgt gcatgtgttc agaaaggctg cttgtgacac ctgggagcca      240
tttgcctctg ggaaaaccag tgagtctgga gagctgcatg ggctcacaac tgaggaggaa      300
tttgtagaag ggatatacaa agtggaaata gacaccaaat cttactggaa ggcacttggc      360
atctccccat tccatgagca tgcagaggtg gtattcacag ccaacgactc cggcccccgc      420
cgctacacca ttgccgccct gctgagcccc tactcctatt ccaccacggc tgtcgtcacc      480
aatcccaagg aataa                                                      495
```

<210> SEQ ID NO 12
<211> LENGTH: 495
<212> TYPE: DNA
<213> ORGANISM: Homo sapiens

<400> SEQUENCE: 12

```
atgatcgaag gtccgactct gcgtcagtgg ctggctgctc gtgctggcgg tggtggcgga       60
gggggtggca ttgagggccc aacccttcgc caatggcttg cagcacgcgc aggtccaact      120
ggtaccggtg aatccaaggc tcctctgatg gtcaaagttc tagatgctgt ccgaggcagt      180
cctgccatca atgtggccgt gcatgtgttc agaaaggctg ctgatgacac ctgggagcca      240
tttgcctctg ggaaaaccag tgagtctgga gagctgcatg ggctcacaac tgaggaggaa      300
tttgtagaag ggatatacaa agtggaaata gacaccaaat cttactggaa gtgtcttggc      360
atctccccat tccatgagca tgcagaggtg gtattcacag ccaacgactc cggcccccgc      420
cgctacacca ttgccgccct gctgagcccc tactcctatt ccaccacggc tgtcgtcacc      480
aatcccaagg aataa                                                      495
```

<210> SEQ ID NO 13
<211> LENGTH: 495
<212> TYPE: DNA
<213> ORGANISM: Homo sapiens

<400> SEQUENCE: 13

```
atgatcgaag gtccgactct gcgtcagtgg ctggctgctc gtgctggcgg tggtggcgga       60
gggggtggca ttgagggccc aacccttcgc caatggcttg cagcacgcgc aggtccaact      120
ggtaccggtg aatccaaggc tcctctgatg gtcaaagttc tagatgctgt ccgaggcagt      180
cctgccatca atgtggccgt gcatgtgttc agaaaggctg ctgatgacac ctgggagcca      240
tttgcctctg ggaaaaccag tgagtctgga gagctgcatg ggctcacaac tgaggaggaa      300
tttgtagaag ggatatacaa agtggaaata gacaccaaat cttactggaa ggcactttgc      360
atctccccat tccatgagca tgcagaggtg gtattcacag ccaacgactc cggcccccgc      420
cgctacacca ttgccgccct gctgagcccc tactcctatt ccaccacggc tgtcgtcacc      480
aatcccaagg aataa                                                      495
```

<210> SEQ ID NO 14
<211> LENGTH: 489
<212> TYPE: DNA
<213> ORGANISM: Homo sapiens

<400> SEQUENCE: 14

```
atgtctgttt ctgaaatcca gctgatgcat aacctgggta acatctgaa ctctatggaa      60
cgtgttgaat ggctgcgtaa gaaactgcag gacgttcata actttggtcc aactggtacc     120
ggtgaatcca aggctcctct gatggtcgca gttctagatg ctgtccgagg cagtcctgcc     180
atcaatgtgg ccgtgcatgt gttcagaaag gctgctgatg acacctggga gccatttgcc     240
tctgggaaaa ccagtgagtc tggagagctg catgggctca aactgagga ggaatttgta      300
gaagggatat acaaagtgga aatagacacc aaatcttact ggaagtgtct tggcatctcc     360
ccattccatg agcatgcaga ggtggtattc acagccaacg actccggccc ccgccgctac     420
accattgccg ccctgctgag cccctactcc tattccacca cggctgtcgt caccaatccc     480
aaggaataa                                                             489
```

<210> SEQ ID NO 15
<211> LENGTH: 843
<212> TYPE: DNA
<213> ORGANISM: Homo sapiens

<400> SEQUENCE: 15

```
atgcgaccgt ccggccgtaa gagctccaaa atgcaggctt ccgtatctg ggacgttaac       60
cagaaaacct tctacctgcg caacaaccag ctggttgctg ctacctgca gggtccgaac      120
gttaacctgg aagaaaaaat cgacgttgta ccgatcgaac cgcacgctct gttcctgggt     180
atccacggtg gtaaaatgtg cctgagctgc gtgaaatctg gtgacgaaac tcgtctgcag     240
ctggaagcag ttaacatcac tgacctgagc gaaaaccgca acaggacaa acgtttcgca      300
ttcatccgct ctgacagcgg cccgaccacc agcttcgaat ctgctgcttg cccgggttgg     360
ttcctgtgca ctgctatgga agctgaccag ccggtaagcc tgaccaacat gccggacgaa     420
ggcgtgatgg taaccaaatt ctacttccag gaagacgaag gtccaactgg taccggtgaa     480
tccaaggctc ctctgatggt caaagttcta gatgctgtcc gaggcagtcc tgccatcaat     540
gtggccgtgc atgtgttcag aaaggctgct gatgacacct gggagccatt tgcctctggg     600
aaaaccagtg agtctggaga gctgcatggg ctcacaactg aggaggaatt tgtagaaggg     660
atatacaaag tggaaataga caccaaatct tactggaagg cacttggcat ctccccattc     720
catgagcatg cagaggtggt attcacagcc aacgactccg gccccgccg ctacaccatt      780
gccgccctgc tgagccccta ctcctattcc accacggctg tcgtcaccaa tcccaaggaa     840
taa                                                                   843
```

<210> SEQ ID NO 16
<211> LENGTH: 855
<212> TYPE: DNA
<213> ORGANISM: Homo sapiens

<400> SEQUENCE: 16

```
atgggtccaa ctggtaccgg tgaatccaag gctcctctga tggtcaaagt tctagatgct      60
gtccgaggca gtcctgccat caatgtggcc gtgcatgtgt tcagaaaggc tgctgatgac     120
acctgggagc catttgcctc tgggaaaacc agtgagtctg gagagctgca tgggctcaca     180
actgaggagg aatttgtaga agggatatac aaagtggaaa tagacaccaa atcttactgg     240
```

```
aaggcacttg gcatctcccc attccatgag catgcagagg tggtattcac agccaacgac      300
tccggccccc gccgctacac cattgccgcc ctgctgagcc cctactccta ttccaccacg      360
gctgtcgtca ccaatcccaa ggaaggtagt ggtagccgac cgtccggccg taagagctcc      420
aaaatgcagg ctttccgtat ctgggacgtt aaccagaaaa ccttctacct gcgcaacaac      480
cagctggttg ctggctacct gcagggtccg aacgttaacc tggaagaaaa aatcgacgtt      540
gtaccgatcg aaccgcacgc tctgttcctg ggtatccacg gtggtaaaat gtgcctgagc      600
tgcgtgaaat ctggtgacga aactcgtctg cagctggaag cagttaacat cactgacctg      660
agcgaaaacc gcaaacagga caaacgtttc gcattcatcc gctctgacag cggcccgacc      720
accagcttcg aatctgctgc ttgcccgggt tggttcctgt gcactgctat ggaagctgac      780
cagccggtaa gcctgaccaa catgccggac gaaggcgtga tggtaaccaa attctacttc      840
caggaagacg aataa                                                      855

<210> SEQ ID NO 17
<211> LENGTH: 439
<212> TYPE: DNA
<213> ORGANISM: Homo sapiens

<400> SEQUENCE: 17
catatgggtc caactggtac cggtgaatcc aaggctcctc tgatggtcaa agttctagat       60
gctgtccgag gcagtcctgc catcaatgtg gccgtgcatg tgttcagaaa ggctgctgat      120
gacacctggg agccatttgc ctctgggaaa accagtgagt ctggagagct gcatgggctc      180
acaactgagg aggaatttgt agaagggata tacaaagtgg aaatagacac caaatcttac      240
tggaaggcac tttgcatctc cccattccat gagcatgcag aggtggtatt cacagccaac      300
gactccggcc cccgccgcta caccattgcc gccctgctga gccccactc ctattccacc      360 actgcagtcg tcaccaatcc caaggaagga tcaggatccg aaaacgtcc gccgggtttc      420 tccccgctgt aatctcgag                                                  439

<210> SEQ ID NO 18
<211> LENGTH: 36
<212> TYPE: DNA
<213> ORGANISM: Homo sapiens

<400> SEQUENCE: 18
gaggaataac atatgggtcc aactggtacc ggtgaa                                36

<210> SEQ ID NO 19
<211> LENGTH: 36
<212> TYPE: DNA
<213> ORGANISM: Homo sapiens

<400> SEQUENCE: 19
ccgcggatcc tcgagattat tccttgggat tggtga                                36

<210> SEQ ID NO 20
<211> LENGTH: 48
<212> TYPE: DNA
<213> ORGANISM: Homo sapiens

<400> SEQUENCE: 20
gaggaataac atatgggtcc aactggtacc ggtgaatcca aggctcct                   48

<210> SEQ ID NO 21
<211> LENGTH: 24
<212> TYPE: DNA
```

```
<213> ORGANISM: Homo sapiens

<400> SEQUENCE: 21
agaaaggctt gtgatgacac ctgg                                          24

<210> SEQ ID NO 22
<211> LENGTH: 24
<212> TYPE: DNA
<213> ORGANISM: Homo sapiens

<400> SEQUENCE: 22
ccaggtgtca tcacaagcct ttct                                          24

<210> SEQ ID NO 23
<211> LENGTH: 24
<212> TYPE: DNA
<213> ORGANISM: Homo sapiens

<400> SEQUENCE: 23
agaaaggctg cttgtgacac ctgg                                          24

<210> SEQ ID NO 24
<211> LENGTH: 24
<212> TYPE: DNA
<213> ORGANISM: Homo sapiens

<400> SEQUENCE: 24
ccaggtgtca caagcagcct ttct                                          24

<210> SEQ ID NO 25
<211> LENGTH: 24
<212> TYPE: DNA
<213> ORGANISM: Homo sapiens

<400> SEQUENCE: 25
tactggaagt gtcttggcat ctcc                                          24

<210> SEQ ID NO 26
<211> LENGTH: 24
<212> TYPE: DNA
<213> ORGANISM: Homo sapiens

<400> SEQUENCE: 26
ggagatgcca agacacttcc agta                                          24

<210> SEQ ID NO 27
<211> LENGTH: 24
<212> TYPE: DNA
<213> ORGANISM: Homo sapiens

<400> SEQUENCE: 27
aaggcacttt gcatctcccc attc                                          24

<210> SEQ ID NO 28
<211> LENGTH: 24
<212> TYPE: DNA
<213> ORGANISM: Homo sapiens

<400> SEQUENCE: 28
gaatggggag atgcaaagtg cctt                                          24

<210> SEQ ID NO 29
<211> LENGTH: 21
<212> TYPE: DNA
```

-continued

<210> SEQ ID NO 29
<211> LENGTH: 21
<212> TYPE: DNA
<213> ORGANISM: Homo sapiens

<400> SEQUENCE: 29
ctgatggtcg cagttctaga t        21

<210> SEQ ID NO 30
<211> LENGTH: 21
<212> TYPE: DNA
<213> ORGANISM: Homo sapiens

<400> SEQUENCE: 30
atctagaact gcgaccatca g        21

<210> SEQ ID NO 31
<211> LENGTH: 36
<212> TYPE: DNA
<213> ORGANISM: Homo sapiens

<400> SEQUENCE: 31
gaggaataac atatgatcga aggtccgact ctgcgt        36

<210> SEQ ID NO 32
<211> LENGTH: 41
<212> TYPE: DNA
<213> ORGANISM: Homo sapiens

<400> SEQUENCE: 32
ttcaccggta ccagttggac ctgcgcgtgc tgcaagccat t        41

<210> SEQ ID NO 33
<211> LENGTH: 33
<212> TYPE: DNA
<213> ORGANISM: Homo sapiens

<400> SEQUENCE: 33
gaggaataac atatgtctgt ttctgaaatc cag        33

<210> SEQ ID NO 34
<211> LENGTH: 36
<212> TYPE: DNA
<213> ORGANISM: Homo sapiens

<400> SEQUENCE: 34
ttcaccggta ccagttggac caaagttatg aacgtc        36

<210> SEQ ID NO 35
<211> LENGTH: 32
<212> TYPE: DNA
<213> ORGANISM: Homo sapiens

<400> SEQUENCE: 35
gaggaataac atatgcgacc gtccggacgt aa        32

<210> SEQ ID NO 36
<211> LENGTH: 36
<212> TYPE: DNA
<213> ORGANISM: Homo sapiens

<400> SEQUENCE: 36
ttctacttcc aggaagacga aggtccaact ggtacc        36

<210> SEQ ID NO 37
<211> LENGTH: 54
<212> TYPE: DNA

<213> ORGANISM: Homo sapiens

<400> SEQUENCE: 37
gtcgtcacca atcccaagga aggtagtggt agccgaccgt ccggccgtaa gagc        54

<210> SEQ ID NO 38
<211> LENGTH: 40
<212> TYPE: DNA
<213> ORGANISM: Homo sapiens

<400> SEQUENCE: 38
ccgcggatcc tcgagattat tcgtcttcct ggaagtagaa                        40

<210> SEQ ID NO 39
<211> LENGTH: 36
<212> TYPE: DNA
<213> ORGANISM: Homo sapiens

<400> SEQUENCE: 39
gaggaataac atatgggtcc aactggtacc ggtgaa                            36

<210> SEQ ID NO 40
<211> LENGTH: 26
<212> TYPE: DNA
<213> ORGANISM: Homo sapiens

<400> SEQUENCE: 40
aatatactgc agtggtggaa taggag                                       26

<210> SEQ ID NO 41
<211> LENGTH: 68
<212> TYPE: DNA
<213> ORGANISM: Homo sapiens

<400> SEQUENCE: 41
gtcgtcacca atcccaagga aggatcagga tccggaaaac gtccgccggg tttctccccg  60
ctgtaatc                                                          68

<210> SEQ ID NO 42
<211> LENGTH: 76
<212> TYPE: DNA
<213> ORGANISM: Homo sapiens

<400> SEQUENCE: 42
tcgagattac agcggggaga aacccggcgg acgttttccg gatcctgatc cttccttggg  60
attggtgacg actgca                                                 76

<210> SEQ ID NO 43
<211> LENGTH: 489
<212> TYPE: DNA
<213> ORGANISM: Homo sapiens

<400> SEQUENCE: 43
atgtctgttt ctgaaatcca gctgatgcat aacctgggta acatctgaa ctctatggaa   60 cgtgttgaat ggctgcgtaa gaaactgcag gacgttcata actttggtcc aactggtacc  120
ggtgaatcca aggctcctct gatggtcgca gttctagatg ctgtccgagg cagtcctgcc  180
atcaatgtgg ccgtgcatgt gttcagaaag gctgctgatg acacctggga gccatttgcc  240
tctgggaaaa ccagtgagtc tggagagctg catgggctca caactgagga ggaatttgta  300
gaagggatat acaaagtgga aatagacacc aaatcttact ggaagtgtct tggcatctcc  360

```
ccattccatg agcatgcaga ggtggtattc acagccaacg actccggccc ccgccgctac    420
accattgccg ccctgctgag cccctactcc tattccacca cggctgtcgt caccaatccc    480
aaggaataa                                                            489

<210> SEQ ID NO 44
<211> LENGTH: 25
<212> TYPE: DNA
<213> ORGANISM: Homo sapiens

<400> SEQUENCE: 44
cgtacaggtt tacgcaagaa aatgg                                           25

<210> SEQ ID NO 45
<211> LENGTH: 62
<212> TYPE: DNA
<213> ORGANISM: Homo sapiens

<400> SEQUENCE: 45
ggattcaccg gtaccagttg gaccaccacc accaccacca cccgcactgc ctgaaccaga     60
gc                                                                    62

<210> SEQ ID NO 46
<211> LENGTH: 71
<212> TYPE: DNA
<213> ORGANISM: Homo sapiens

<400> SEQUENCE: 46
tgactaagcc atatgaaaca tcatcaccat caccatcatg acgaagttga tcacggtgaa     60
ggtactttca c                                                          71

<210> SEQ ID NO 47
<211> LENGTH: 44
<212> TYPE: DNA
<213> ORGANISM: Homo sapiens

<400> SEQUENCE: 47
ggattcaccg gtaccagttg gaccaccacc accaccaccg ctac                      44

<210> SEQ ID NO 48
<211> LENGTH: 594
<212> TYPE: DNA
<213> ORGANISM: Homo sapiens

<400> SEQUENCE: 48
atgaaacatc atcaccatca ccatcatgac gaagttgatc acggtgaagg tactttcact     60
tctgacgttt cttcttatct ggaaggtcag gctgctaaag aattcatcgc ttggctggtt    120
aaaggtcgtg gtggttctgg ttctgctact ggtggttccg gctccaccgc aagctctggt    180
tcaggcagtg cgggtggtgg tggtggtggt ggtccaactg gtaccggtga atccaaggct    240
cctctgatgg tcaaagttct agatgctgtc cgaggcagtc ctgccatcaa tgtggccgtg    300
catgtgttca aaaggctgc tgatgacacc tgggagccat tgcctctgg aaaaccagt       360 gagtctggag agctgcatgg gctcacaact gaggaggaat tgtagaagg gatatacaaa     420 gtggaaatag acaccaaatc ttactggaag gcactttgca tctccccatt ccatgagcat    480
gcagaggtgg tattcacagc caacgactcc ggccccgcc gctacaccat tgccgccctg    540
ctgagcccct actcctattc caccacggct gtcgtcacca atcccaagga ataa          594

<210> SEQ ID NO 49
```

<211> LENGTH: 591
<212> TYPE: DNA
<213> ORGANISM: Homo sapiens

<400> SEQUENCE: 49

| | | | | | |
|---|---|---|---|---|---|
| atgaaacatc | atcaccatca | ccatcatgac | gaagttgatc | acggtgaagg | tactttcact | 60 |
| tctgacgttt | cttcttatct | ggaaggtcag | gctgctaaag | aattcatcgc | ttggctggtt | 120 |
| aaaggtcgtg | gtggtggtgg | tggttctggt | ggtggtggtt | ctggtggtgg | tggttctggc | 180 |
| ggcggtggta | gcggtggtgg | tggtggtggt | ccaactggta | ccggtgaatc | caaggctcct | 240 |
| ctgatggtcg | cagttctaga | tgctgtccga | ggcagtcctg | ccatcaatgt | ggccgtgcat | 300 |
| gtgttcagaa | aggctgctga | tgacacctgg | gagccatttg | cctctgggaa | aaccagtgag | 360 |
| tctggagagc | tgcatgggct | cacaactgag | gaggaatttg | tagaagggat | atacaaagtg | 420 |
| gaaatagaca | ccaaatctta | ctggaaggca | ctttgcatct | ccccattcca | tgagcatgca | 480 |
| gaggtggtat | tcacagccaa | cgactccggc | ccccgccgct | acaccattgc | cgccctgctg | 540 |
| agcccctact | cctattccac | cacggctgtc | gtcaccaatc | ccaaggaata | a | 591 |

<210> SEQ ID NO 50
<211> LENGTH: 76
<212> TYPE: DNA
<213> ORGANISM: Homo sapiens

<400> SEQUENCE: 50

| | | | | | |
|---|---|---|---|---|---|
| agacctgtac | atatgaaaca | tcatcaccat | caccatcatg | acgaagttga | tcacggtgaa | 60 |
| ggtactttca | cttctg | | | | | 76 |

<210> SEQ ID NO 51
<211> LENGTH: 20
<212> TYPE: DNA
<213> ORGANISM: Homo sapiens

<400> SEQUENCE: 51

| | |
|---|---|
| gggggaagag gaaaactgac | 20 |

<210> SEQ ID NO 52
<211> LENGTH: 894
<212> TYPE: DNA
<213> ORGANISM: Homo sapiens

<400> SEQUENCE: 52

| | | | | | |
|---|---|---|---|---|---|
| atgaaacatc | atcaccatca | ccatcatgac | gaagttgatc | acggtgaagg | tactttcact | 60 |
| tctgacgttt | cttcttatct | ggaaggtcag | gctgctaaag | aattcatcgc | ttggctggtt | 120 |
| aaaggtcgtg | gtggtctgg | ttctgctact | ggtggttccg | gctccaccgc | aagctctggt | 180 |
| tcaggcagtg | cgactcatgg | tggtggtggt | ggtgacaaaa | ctcacacatg | tccaccgtgc | 240 |
| ccagcacctg | aactcctggg | gggaccgtca | gttttcctct | tccccccaaa | acccaaggac | 300 |
| accctcatga | tctcccggac | ccctgaggtc | acatgcgtgg | tggtggacgt | gagccacgaa | 360 |
| gaccctgagg | tcaagttcaa | ctggtacgtg | gacggcgtgg | aggtgcataa | tgccaagaca | 420 |
| aagccgcggg | aggagcagta | caacagcacg | taccgtgtgg | tcagcgtcct | caccgtcctg | 480 |
| caccaggact | ggctgaatgg | caaggagtac | aagtgcaagg | tctccaacaa | agccctccca | 540 |
| gcccccatcg | agaaaaccat | ctccaaagcc | aaagggcagc | cccgagaacc | acaggtgtac | 600 |
| accctgcccc | catcccggga | tgagctgacc | aagaaccagg | tcagcctgac | ctgcctggtc | 660 |
| aaaggcttct | atcccagcga | catcgccgtg | gagtgggaga | gcaatgggca | gccggagaac | 720 |

```
aactacaaga ccacgcctcc cgtgctggac tccgacggct ccttcttcct ctacagcaag    780
ctcaccgtgg acaagagcag gtggcagcag gggaacgtct tctcatgctc cgtgatgcat    840
gaggctctgc acaaccacta cacgcagaag agcctctccc tgtctccggg taaa          894

<210> SEQ ID NO 53
<211> LENGTH: 60
<212> TYPE: DNA
<213> ORGANISM: Homo sapiens

<400> SEQUENCE: 53
gtcgtcacca atcccaagga aggttctggc tccggatcag ggggaccgtc agttttcctc     60

<210> SEQ ID NO 54
<211> LENGTH: 52
<212> TYPE: DNA
<213> ORGANISM: Homo sapiens

<400> SEQUENCE: 54
ccgcggatcc tcgagattag gatccagaac cccctttggc tttggagatg gt             52

<210> SEQ ID NO 55
<211> LENGTH: 42
<212> TYPE: DNA
<213> ORGANISM: Homo sapiens

<400> SEQUENCE: 55
gaggaataac atatgggtcc aactggtacc ggtgaatcca ag                        42

<210> SEQ ID NO 56
<211> LENGTH: 735
<212> TYPE: DNA
<213> ORGANISM: Homo sapiens

<400> SEQUENCE: 56
atgggtccaa ctggtaccgg tgaatccaag gctcctctga tggtcaaagt tctagatgct     60
gtccgaggca gtcctgccat caatgtggcc gtgcatgtgt tcagaaaggc tgctgatgac    120
acctgggagc catttgcctc tgggaaaaac agtgagtctg gagagctgca tgggctcaca    180
actgaggagg aatttgtaga agggatatac aaagtggaaa tagacaccaa atcttactgg    240
aaggcacttg gcatctcccc attccatgag catgcagagg tggtattcac agccaacgac    300
tccggccccc gccgctacac cattgccgcc ctgctgagcc cctactccta ttccaccacg    360
gctgtcgtca ccaatcccaa ggaaggttct ggctccggat caggggggacc gtcagttttc    420 ctcttccccc caaaacccaa ggacaccctc atgatctccc ggacccctga ggtcacatgc    480
gtggtggtgg acgtgagcca cgaagaccct gaggtcaagt tcaactggta cgtggacggc    540
gtggaggtgc ataatgccaa gacaaagccg cgggaggagc agtacaacag cacgtaccgt    600
gtggtcagcg tcctcaccgt cctgcaccag gactggctga atggcaagga gtacaagtgc    660
aaggtctcca acaaagccct cccagccccc atcgagaaaa ccatctccaa agccaagggg    720
ggttctggat cctaa                                                     735

<210> SEQ ID NO 57
<211> LENGTH: 843
<212> TYPE: DNA
<213> ORGANISM: Homo sapiens

<400> SEQUENCE: 57
atgatcgaag gtccgactct gcgtcagtgg ctggctgctc gtgctggcgg tggtggcgga     60
```

```
gggggtggca ttgagggccc aacccttcgc caatggcttg cagcacgcgc aggtccaact      120
ggtaccggtg aatccaaggc tcctctgatg gtcaaagttc tagatgctgt ccgaggcagt      180
cctgccatca atgtggccgt gcatgtgttc agaaaggctg ctgatgacac ctgggagcca      240
tttgcctctg ggaaaaccag tgagtctgga gagctgcatg gctcacaac tgaggaggaa       300 tttgtagaag ggatatacaa agtggaaata gacaccaaat cttactggaa ggcacttggc      360
atctccccat ccatgagca tgcagaggtg gtattcacag ccaacgactc cggcccccgc       420
cgctacacca ttgccgccct gctgagcccc tactcctatt ccaccacggc tgtcgtcacc      480
aatcccaagg aaggttctgg ctccggatca ggggaccgt cagttttcct cttccccca       540 aaacccaagg acaccctcat gatctcccgg acccctgagg tcacatgcgt ggtggtggac      600
gtgagccacg aagaccctga ggtcaagttc aactggtacg tggacggcgt ggaggtgcat      660
aatgccaaga caaagccgcg ggaggagcag tacaacagca cgtaccgtgt ggtcagcgtc      720
ctcaccgtcc tgcaccagga ctggctgaat ggcaaggagt acaagtgcaa ggtctccaac      780
aaagccctcc cagcccccat cgagaaaacc atctccaaag ccaaggggg ttctggatcc       840 taa                                                                   843

<210> SEQ ID NO 58
<211> LENGTH: 35
<212> TYPE: DNA
<213> ORGANISM: Homo sapiens

<400> SEQUENCE: 58
gaggaataag gatccatcga aggtccgact ctgcg                                 35

<210> SEQ ID NO 59
<211> LENGTH: 843
<212> TYPE: DNA
<213> ORGANISM: Homo sapiens

<400> SEQUENCE: 59
atgggtccaa ctggtaccgg tgaatccaag gctcctctga tggtcaaagt tctagatgct       60
gtccgaggca gtcctgccat caatgtggcc gtgcatgtgt cagaaaggc tgctgatgac       120 acctgggagc catttgcctc tgggaaaacc agtgagtctg agagctgca tgggctcaca       180 actgaggagg aatttgtaga agggatatac aaagtggaaa tagacaccaa atcttactgg      240
aaggcacttg gcatctcccc attccatgag catgcagagg tggtattcac agccaacgac      300
tccggccccc gccgctacac cattgccgcc ctgctgagcc cctactccta ttccaccacg      360
gctgtcgtca ccaatcccaa ggaaggttct ggctccggat caggggggacc gtcagttttc      420 ctcttccccc caaaacccaa ggacaccctc atgatctccc ggacccctga ggtcacatgc      480
gtggtggtgg acgtgagcca cgaagaccct gaggtcaagt tcaactggta cgtggacggc      540
gtggaggtgc ataatgccaa gacaaagccg cggaggagc agtacaacag cacgtaccgt      600
gtggtcagcg tcctcaccgt cctgcaccag gactggctga atggcaagga gtacaagtgc      660
aaggtctcca acaaagccct cccagccccc atcgagaaaa ccatctccaa agccaagggg      720
ggttctggat ccatcgaagg tccgactctg cgtcagtggc tggctgctcg tgctggcggt      780
ggtggcggag ggggtggcat tgagggccca accttcgcc aatggcttgc agcacgcgca       840
taa                                                                   843

<210> SEQ ID NO 60
<211> LENGTH: 48
<212> TYPE: DNA
```

<213> ORGANISM: Homo sapiens

<400> SEQUENCE: 60
ttcaccggta ccagttggac cagaaccccc tttggctttg gagatggt        48

<210> SEQ ID NO 61
<211> LENGTH: 48
<212> TYPE: DNA
<213> ORGANISM: Homo sapiens

<400> SEQUENCE: 61
gaggaataac atatgggatc cggttctggg ggaccgtcag ttttcctc        48

<210> SEQ ID NO 62
<211> LENGTH: 723
<212> TYPE: DNA
<213> ORGANISM: Homo sapiens

<400> SEQUENCE: 62
atgggatccg gttctggggg accgtcagtt ttcctcttcc ccccaaaacc caaggacacc     60
ctcatgatct cccggacccc tgaggtcaca tgcgtggtgg tggacgtgag ccacgaagac    120
cctgaggtca agttcaactg gtacgtggac ggcgtggagg tgcataatgc caagacaaag    180
ccgcgggagg agcagtacaa cagcacgtac cgtgtggtca gcgtcctcac cgtcctgcac    240
caggactggc tgaatggcaa ggagtacaag tgcaaggtct ccaacaaagc cctcccagcc    300
cccatcgaga aaaccatctc caaagccaaa ggggttctg gtccaactgg taccggtgaa    360
tccaaggctc ctctgatggt caaagttcta gatgctgtcc gaggcagtcc tgccatcaat    420
gtggccgtgc atgtgttcag aaaggctgct gatgacacct gggagccatt tgcctctggg    480
aaaaccagtg agtctggaga gctgcatggg ctcacaactg aggaggaatt tgtagaaggg    540
atatacaaag tggaaataga caccaaatct tactggaagg cacttggcat ctccccattc    600
catgagcatg cagaggtggt attcacagcc aacgactccg cccccgccg ctacaccatt    660
gccgccctgc tgagccccta ctcctattcc accacggctg tcgtcaccaa tcccaaggaa    720
taa                                                                  723

<210> SEQ ID NO 63
<211> LENGTH: 33
<212> TYPE: DNA
<213> ORGANISM: Homo sapiens

<400> SEQUENCE: 63
gaggaataac atatgatcga aggtccgact ctg                          33

<210> SEQ ID NO 64
<211> LENGTH: 36
<212> TYPE: DNA
<213> ORGANISM: Homo sapiens

<400> SEQUENCE: 64
taacatatgg atcctgcgc gtgctgcaag ccattg                        36

<210> SEQ ID NO 65
<211> LENGTH: 831
<212> TYPE: DNA
<213> ORGANISM: Homo sapiens

<400> SEQUENCE: 65
atgatcgaag gtccgactct gcgtcagtgg ctggctgctc gtgctggcgg tggtggcgga     60

-continued

| | |
|---|---|
| gggggtggca ttgagggccc aaccccttcgc caatggcttg cagcacgcgc aggatccggt | 120 |
| tctgggggac cgtcagtttt cctcttcccc ccaaaaccca aggacaccct catgatctcc | 180 |
| cggacccctg aggtcacatg cgtggtggtg gacgtgagcc acgaagaccc tgaggtcaag | 240 |
| ttcaactggt acgtggacgg cgtggaggtg cataatgcca agacaaagcc gcgggaggag | 300 |
| cagtacaaca gcacgtaccg tgtggtcagc gtcctcaccg tcctgcacca ggactggctg | 360 |
| aatggcaagg agtacaagtg caaggtctcc aacaaagccc tcccagcccc catcgagaaa | 420 |
| accatctcca aagccaaagg gggttctggt ccaactggta ccggtgaatc caaggctcct | 480 |
| ctgatggtca aagttctaga tgctgtccga ggcagtcctg ccatcaatgt ggccgtgcat | 540 |
| gtgttcagaa aggctgctga tgacacctgg gagccatttg cctctgggaa aaccagtgag | 600 |
| tctggagagc tgcatgggct cacaactgag gaggaatttg tagaagggat atacaaagtg | 660 |
| gaaatagaca ccaaatctta ctggaaggca cttggcatct ccccattcca tgagcatgca | 720 |
| gaggtggtat tcacagccaa cgactccggc cccgccgct acaccattgc cgccctgctg | 780 |
| agcccctact cctattccac cacggctgtc gtcaccaatc ccaaggaata a | 831 |

<210> SEQ ID NO 66
<211> LENGTH: 42
<212> TYPE: DNA
<213> ORGANISM: Homo sapiens

<400> SEQUENCE: 66

| | |
|---|---|
| gtcgtcacca atcccaagga aggttctggt tctggtatcg aa | 42 |

<210> SEQ ID NO 67
<211> LENGTH: 40
<212> TYPE: DNA
<213> ORGANISM: Homo sapiens

<400> SEQUENCE: 67

| | |
|---|---|
| ccgcggatcc tcgagattat gcgcgtgctg caagccattg | 40 |

<210> SEQ ID NO 68
<211> LENGTH: 510
<212> TYPE: DNA
<213> ORGANISM: Homo sapiens

<400> SEQUENCE: 68

| | |
|---|---|
| atgggtccaa ctggtaccgg tgaatccaag tgtcctctga tggtcaaagt tctagatgct | 60 |
| gtccgaggca gtcctgccat caatgtggcc gtgcatgtgt tcagaaaggc tgctgatgac | 120 |
| acctgggagc catttgcctc tgggaaaacc agtgagtctg agagctgca tgggctcaca | 180 |
| actgaggagg aatttgtaga aggatatac aaagtggaaa tagacaccaa atcttactgg | 240 |
| aaggcacttg gcatctcccc attccatgag catgcagagg tggtattcac agccaacgac | 300 |
| tccgcccccc gccgctacac cattgccgcc tgctgagcc ctactcccta ttccaccacg | 360 |
| gctgtcgtca ccaatcccaa ggaaggttct ggttctggta tcgaaggtcc gactctgcgt | 420 |
| cagtggctgg ctgctcgtgc tggcggtggt ggcggagggg gtggcattga gggcccaacc | 480 |
| cttcgccaat ggcttgcagc acgcgcataa | 510 |

<210> SEQ ID NO 69
<211> LENGTH: 510
<212> TYPE: DNA
<213> ORGANISM: Homo sapiens

<400> SEQUENCE: 69

```
atgggtccaa ctggtaccgg tgaatccaag gctcctctga tggtcgcagt tctagatgct        60
gtccgaggca gtcctgccat caatgtggcc gtgcatgtgt tcagaaaggc tgctgatgac       120
acctgggagc catttgcctc tgggaaaacc agtgagtctg gagagctgca tgggctcaca       180
actgaggagg aatttgtaga agggatatac aaagtggaaa tagacaccaa atcttactgg       240
aaggcacttg gcatctcccc attccatgag catgcagagg tggtattcac agccaacgac       300
tccggccccc gccgctacac cattgccgcc ctgctgagcc cctactccta ttccaccacg       360
gctgtcgtca ccaatcccaa ggaaggttct ggttctggta tcgaaggtcc gactctgcgt       420
cagtggctgg ctgctcgtgc tggcggtggt ggcggagggg gtggcattga gggcccaacc       480
cttcgccaat ggcttgcagc acgcgcataa                                        510

<210> SEQ ID NO 70
<211> LENGTH: 510
<212> TYPE: DNA
<213> ORGANISM: Homo sapiens

<400> SEQUENCE: 70
atgggtccaa ctggtaccgg tgaatccaag gctcctctga tggtcgcagt tctagatgct        60
gtccgaggca gtcctgccat caatgtggcc gtgcatgtgt tcagaaaggc ttgtgatgac       120
acctgggagc catttgcctc tgggaaaacc agtgagtctg gagagctgca tgggctcaca       180
actgaggagg aatttgtaga agggatatac aaagtggaaa tagacaccaa atcttactgg       240
aaggcacttg gcatctcccc attccatgag catgcagagg tggtattcac agccaacgac       300
tccggccccc gccgctacac cattgccgcc ctgctgagcc cctactccta ttccaccacg       360
gctgtcgtca ccaatcccaa ggaaggttct ggttctggta tcgaaggtcc gactctgcgt       420
cagtggctgg ctgctcgtgc tggcggtggt ggcggagggg gtggcattga gggcccaacc       480
cttcgccaat ggcttgcagc acgcgcataa                                        510

<210> SEQ ID NO 71
<211> LENGTH: 510
<212> TYPE: DNA
<213> ORGANISM: Homo sapiens

<400> SEQUENCE: 71
atgggtccaa ctggtaccgg tgaatccaag gctcctctga tggtcgcagt tctagatgct        60
gtccgaggca gtcctgccat caatgtggcc gtgcatgtgt tcagaaaggc tgctgatgac       120
acctgggagc catttgcctc tgggaaaacc agtgagtctg gagagctgca tgggctcaca       180
actgaggagg aatttgtaga agggatatac aaagtggaaa tagacaccaa atcttactgg       240
aagtgtcttg gcatctcccc attccatgag catgcagagg tggtattcac agccaacgac       300
tccggccccc gccgctacac cattgccgcc ctgctgagcc cctactccta ttccaccacg       360
gctgtcgtca ccaatcccaa ggaaggttct ggttctggta tcgaaggtcc gactctgcgt       420
cagtggctgg ctgctcgtgc tggcggtggt ggcggagggg gtggcattga gggcccaacc       480
cttcgccaat ggcttgcagc acgcgcataa                                        510

<210> SEQ ID NO 72
<211> LENGTH: 510
<212> TYPE: DNA
<213> ORGANISM: Homo sapiens

<400> SEQUENCE: 72
atgggtccaa ctggtaccgg tgaatccaag gctcctctga tggtcgcagt tctagatgct        60
```

```
gtccgaggca gtcctgccat caatgtggcc gtgcatgtgt tcagaaaggc tgctgatgac    120
acctgggagc catttgcctc tgggaaaacc agtgagtctg gagagctgca tgggctcaca    180
actgaggagg aatttgtaga agggatatac aaagtggaaa tagacaccaa atcttactgg    240
aaggcacttt gcatctcccc attccatgag catgcagagg tggtattcac agccaacgac    300
tccggccccc gccgctacac cattgccgcc ctgctgagcc cctactccta ttccaccacg    360
gctgtcgtca ccaatcccaa ggaaggttct ggttctggta tcgaaggtcc gactctgcgt    420
cagtggctgg ctgctcgtgc tggcggtggt ggcggagggg gtggcattga gggcccaacc    480
cttcgccagt ggcttgcagc acgcgcataa                                     510

<210> SEQ ID NO 73
<211> LENGTH: 495
<212> TYPE: DNA
<213> ORGANISM: Homo sapiens

<400> SEQUENCE: 73
atgatcgaag gtccgactct gcgtcagtgg ctggctgctc gtgctggcgg tggtggcgga    60
gggggtggca ttgagggccc aaccttcgc caatggcttg cagcacgcgc aggtccaact    120
ggtaccggtg aatccaaggc tcctctgatg gtcgcagttc tagatgctgt ccgaggcagt    180
cctgccatca atgtggccgt gcatgtgttc agaaaggctg ctgatgacac ctgggagcca    240
tttgcctctg ggaaaaccag tgagtctgga gagctgcatg gctcacaac tgaggaggaa    300 tttgtagaag ggatatacaa agtggaaata gacaccaaat cttactggaa ggcactttgc    360
atctccccat tccatgagca tgcagaggtg gtattcacag ccaacgactc cggccccgc    420 cgctacacca ttgccgccct gctgagcccc tactcctatt ccaccacggc tgtcgtcacc    480
aatcccaagg aataa                                                     495

<210> SEQ ID NO 74
<211> LENGTH: 495
<212> TYPE: DNA
<213> ORGANISM: Homo sapiens

<400> SEQUENCE: 74
atgatcgaag gtccgactct gcgtcagtgg ctggctgctc gtgctggcgg tggtggcgga    60
gggggtggca ttgagggccc aaccttcgc caatggcttg cagcacgcgc aggtccaact    120
ggtaccggtg aatccaaggc tcctctgatg gtcgcagttc tagatgctgt ccgaggcagt    180
cctgccatca atgtggccgt gcatgtgttc agaaaggctg ctgatgacac ctgggagcca    240
tttgcctctg ggaaaaccag tgagtctgga gagctgcatg gctcacaac tgaggaggaa    300 tttgtagaag ggatatacaa agtggaaata gacaccaaat cttactggaa gtgtcttggc    360
atctccccat tccatgagca tgcagaggtg gtattcacag ccaacgactc cggccccgc    420 cgctacacca ttgccgccct gctgagcccc tactcctatt ccaccacggc tgtcgtcacc    480
aatcccaagg aataa                                                     495

<210> SEQ ID NO 75
<211> LENGTH: 495
<212> TYPE: DNA
<213> ORGANISM: Homo sapiens

<400> SEQUENCE: 75
atgatcgaag gtccgactct gcgtcagtgg ctggctgctc gtgctggcgg tggtggcgga    60
gggggtggca ttgagggccc aaccttcgc caatggcttg cagcacgcgc aggtccaact    120
```

-continued

| | |
|---|---|
| ggtaccggtg aatccaaggc tcctctgatg gtcgcagttc tagatgctgt ccgaggcagt | 180 |
| cctgccatca atgtggccgt gcatgtgttc agaaaggctt gtgatgacac ctgggagcca | 240 |
| tttgcctctg ggaaaaccag tgagtctgga gagctgcatg ggctcacaac tgaggaggaa | 300 |
| tttgtagaag ggatatacaa agtggaaata gacaccaaat cttactggaa ggcacttggc | 360 |
| atctccccat tccatgagca tgcagaggtg gtattcacag ccaacgactc cggcccccgc | 420 |
| cgctacacca ttgccgccct gctgagcccc tactcctatt ccaccacggc tgtcgtcacc | 480 |
| aatcccaagg aataa | 495 |